United States Patent
Booth et al.

(10) Patent No.: US 7,053,070 B2
(45) Date of Patent: May 30, 2006

(54) PYRIDO[2,3-D]PYRIMIDINE-2,7-DIAMINE KINASE INHIBITORS

(75) Inventors: Richard John Booth, Ann Arbor, MI (US); Ellen Myra Dobrusin, Ann Arbor, MI (US); Vara Prasad Venkata Nagendra Josyula, Ann Arbor, MI (US); Dennis Joseph Mc Namara, Ann Arbor, MI (US); Peter Laurence Toogood, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 241 days.

(21) Appl. No.: 10/182,178

(22) PCT Filed: Jan. 23, 2001

(86) PCT No.: PCT/IB01/00069

§ 371 (c)(1),
(2), (4) Date: Jul. 24, 2002

(87) PCT Pub. No.: WO01/55147

PCT Pub. Date: Aug. 2, 2001

(65) Prior Publication Data

US 2003/0073668 A1 Apr. 17, 2003

Related U.S. Application Data

(60) Provisional application No. 60/178,261, filed on Jan. 25, 2000.

(51) Int. Cl.
| | |
|---|---|
| *C07D 471/04* | (2006.01) |
| *A61K 31/519* | (2006.01) |
| *A61P 35/00* | (2006.01) |
| *A61P 9/10* | (2006.01) |

(52) U.S. Cl. ............... 514/81; 544/279; 544/244; 544/117; 514/264.11; 514/234.2

(58) Field of Classification Search ............ 514/264.11, 514/81, 234.2; 544/279, 244, 117
See application file for complete search history.

(56) References Cited

U.S. PATENT DOCUMENTS

| | | | |
|---|---|---|---|
| 5,620,981 A | 4/1997 | Blankley et al. | |
| 5,733,913 A | 3/1998 | Blankley et al. | |
| 5,952,342 A | 9/1999 | Blankley et al. | |
| 2003/0149001 A1 * | 8/2003 | Barvian et al. | ............ 544/279 |
| 2003/0171584 A1 * | 9/2003 | Chen et al. | ................ 544/279 |
| 2004/0224958 A1 * | 11/2004 | Booth et al. | ........... 514/252.16 |

FOREIGN PATENT DOCUMENTS

| | | |
|---|---|---|
| WO | WO 99/61444 A2 | 12/1999 |
| WO | WO 200170741 A1 * | 9/2001 |

OTHER PUBLICATIONS

J. M. Hamby, et al., "Structure–Activity Relationships for a Novel Series of Pyrido[2,3–d]pyrimidine Tyrosine Kinase Inhibitors", J. Med. Chem., 1997, pp 2296–2303, vol. 40, No. 15.

S. Trumpp–Kallmeyer, et al., "Development of a Binding Model to Protein Tyrosine Kinases for Substituted Pyrido [2,3–d]pyrimidine Inhibitors", J. Med. Chem., 1998, pp1752–1763, vol. 41, No. 11.

C. J. Connolly, et al., "Discovery and Structure–Activity Studies of a Novel Series of Pyrido[2,3–d]pyrimidine Tyrosine Kinase Inhibitors", Bioorg. Med. Chem. Letters, 1997, pp 2415–2420, vol. 7, No. 18.

M. R. Barvian, et al., "Preparation of N,N'–Bis9aryl)guanidines from Electron Deficient Amines Via Masked Carbodiimides", Tetrahedron Letters, 1997, pp 6799–6802, vol. 38, No. 39.

* cited by examiner

*Primary Examiner*—Mark L. Berch
(74) *Attorney, Agent, or Firm*—Bryan C. Zielinski; Wendy L. Hsu

(57) ABSTRACT

Disclosed are compounds of the formula

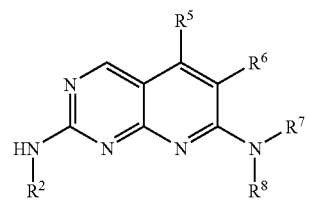

wherein $R^2$, $R^5$, $R^6$, $R^7$, and $R^8$ are as defined herein. These compounds and their pharmaceutical compositions are useful for treating cell proliferative disorders, such as cancer and restenosis. These compounds are potent inhibitors of cdks and growth factor-mediated kinases.

18 Claims, No Drawings

PYRIDO[2,3-D]PYRIMIDINE-2,7-DIAMINE KINASE INHIBITORS

This application is a 371 application of PCT/IB01/00069 filed Jan. 23, 2001, which claims the benefit of priority to U.S. provisional application Ser. No. 60/178,261 filed Jan. 25, 2000.

FIELD OF THE INVENTION

This invention relates to pyrido[2,3-d]pyrimidine-2,7-diamines that inhibit cyclin-dependent serine/threonine kinases and growth factor-mediated tyrosine kinase enzymes and as such are useful to treat cell proliferation diseases and disorders.

BACKGROUND OF THE INVENTION

Summary of the Related Art

Cell cycle kinases are naturally occurring enzymes involved in regulation of the cell cycle (Meijer L., "Chemical Inhibitors of Cyclin-Dependent Kinases," *Progress in Cell Cycle Research*, 1995; 1:351–363). Typical enzymes include serine/threonine kinases such as the cyclin-dependent kinases (cdks) cdk1, cdk2, cdk4, cdk5, cdk6, as well as tyrosine kinases involved in cell cycle regulation. Increased activity or temporally abnormal activation or regulation of these kinases has been shown to result in development of human tumors and other proliferative disorders. Compounds that inhibit cdks, either by blocking the interaction between a cyclin and its kinase partner, or by binding to and inactivating the kinase, cause inhibition of cell proliferation, and are thus useful for treating tumors or other abnormally proliferating cells.

Several compounds that inhibit cdks have demonstrated preclinical antitumor activity. For example, flavopiridol is a flavonoid that has been shown to be a potent inhibitor of several types of breast and lung cancer cells (Kaur et al., *J. Natl. Cancer Inst.*, 1992; 84:1736–1740; *Int. J. Oncol.*, 1996; 9:1143–1168). The compound has been shown to inhibit cdk2 and cdk4. Olomoucine [2-(hydroxyethylamino)-6-benzylamine-9-methylpurine] is a potent inhibitor of cdk2 and cdk5 (Vesely et al., *Eur. J. Biochem.*, 1994; 224:771–786), and has been shown to inhibit proliferation of approximately 60 different human tumor cell lines used by the National Cancer Institute (NCI) to screen for new cancer therapies (Abraham et al., *Biology of the Cell*, 1995; 83:105–120). More recently, the purvalanol class of cdk inhibitors has emerged as more potent derivatives of olomoucine (Gray N. S. et al., *Science*, 1998; 281:533–538).

Tyrosine kinases are essential for the propagation of growth factor signal transduction leading to cell cycle progression, cellular proliferation, differentiation, and migration. Tyrosine kinases include cell surface growth factor receptor tyrosine kinases such as FGFr and PDGFr, as well as nonreceptor tyrosine kinases, including c-Src and lck. Inhibition of these enzymes has been demonstrated to cause antitumor and antiangiogenesis activity (Hamby et al., *Pharmacol. Ther.*, 1999; 82(2–3):169–193).

Several pyrido[2,3-d]pyrimidines that inhibit cdks and growth factor-mediated kinase enzymes are known (WO 98/33798). U.S. Pat. Nos. 5,733,913 and 5,733,914 describe 6-aryl-pyrido[2,3-d]pyrimidines.

Despite the progress that has been made, the search continues for low molecular weight compounds that are orally bioavailable and useful for treating a wide variety of human tumors and other proliferative disorders, including restenosis, angiogenesis, diabetic retinopathy, psoriasis, surgical adhesions, macular degeneration, and atherosclerosis. The present invention provides such compounds, their pharmaceutical formulations, and their use in treating proliferative disorders.

SUMMARY OF THE INVENTION

This invention provides novel pyrido[2,3-d]pyrimidine-2,7-diamine compounds which function as inhibitors of cell cycle regulatory kinases such as the cyclin dependent kinases as well as the growth factor-mediated tyrosine kinases. Thus, these compounds are useful to treat cell proliferative disorders such as atherosclerosis and restenosis; cancer; angiogenesis; viral infections including DNA viruses such as herpes and RNA viruses such as HIV; fungal infections; type 1 diabetes, diabetic neuropathy and retinopathy; multiple sclerosis; glomerulonephritis; neurodegenerative diseases including Alzheimer's disease; autoimmune diseases such as psoriasis, rheumatoid arthritis, and lupus; organ transplant rejection and host versus graft disease; gout; polycystic kidney disease; and inflammation including inflammatory bowel disease.

Accordingly, the present invention provides pyrido[2,3-d]pyrimidine having the generic structure of Formula I

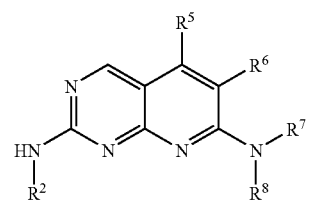

I wherein:
$R^2$, $R^7$, $R^{13}$, $R^{14}$ and $R^{15}$ are independently hydrogen, or
  lower alkyl, lower alkenyl, or lower alkynyl, each of which is optionally substituted with up to 5 groups independently selected from halogen, cyano, nitro, $-R^9$, $-NR^9R^{10}$, $-OR^9$, $-(CH_2)_nCO_2R^9$, $-(CH_2)_nSO_2R^{11}$, $-(CH_2)_nR^{11}$, $-COR^9$, $-CONR^9R^{10}$, $-SO_3R^9$, $-SO_2NR^9R^{10}$, $-SO_2R^9$, $-SR^9$, $-PO_3R^9R^{10}$, $-POR^9R^{10}$, $-PO(NR^9R^{10})_2$, $-NR^9COR^{10}$, $-NR^9CO_2R^{10}$, $-NR^9CONR^9R^{10}$, $-NR^9SO_2R^{10}$, or
  a heterocycle optionally substituted with up to 3 groups independently selected from $-R^9$, $-NR^9R^{10}$, $-OR^9$, $-NR^9COR^{10}$, $-COR^{10}$, $-(CH_2)_nSO_2R^{11}$, $-(CH_2)_nR^{11}$, or
$-(CH_2)_nR^{12}$ optionally substituted with up to 5 groups independently selected from halogen, cyano, nitro, $-R^9$, $-NR^9R^{10}$, $-OR^9$, $-(CH_2)_nCO_2R^9$, $-(CH_2)_nSO_2R^{11}$, $-(CH_2)_nR^{11}$, $-COR^9$, $-CONR^9R^{10}$, $-SO_3R^9$, $-SO_2NR^9R^{10}$, $-SO_2R^9$, $-SR^9$, $-PO_3R^9R^{10}$, $-POR^9R^{10}$, $-PO(NR^9R^{10})_2$, $-NR^9COR^{10}$, $-NR^9CO_2R^{10}$, $-NR^9CONR^9R^{10}$, $-NR^9SO_2R^{10}$, or
  a heterocycle optionally substituted with up to 3 groups independently selected from $-R^9$, $-NR^9R^{10}$, $-OR^9$, $-NR^9COR^{10}$, $-COR^{10}$, $-(CH_2)_nSO_2R^{11}$, $-(CH_2)_nR^{11}$;
$R^5$ is halogen, cyano, nitro, $-R^9$, $-NR^9R^{10}$, or $-OR^9$;
$R^6$ is halogen, cyano, nitro, $-R^9$, $-NR^9R^{10}$, $-OR^9$, $-CO_2R^9$, $-COR^9$, $-CONR^9R^{10}$, $-NR^9COR^{10}$, $-SO_2NR^9R^{10}$, $-SO_2R^9$, $-SO_3R^9$, $-SR^9$, $-PO_3R^9R^{10}$, $-POR^9R^{10}$, $-PO(NR^9R^{10})_2$, or
  lower alkenyl or lower alkynyl optionally substituted with $-R^9$;

$R^8$ is H, $-CO_2R^{13}$, $-COR^{13}$, $-CONR^{13}R^{14}$, $-CSNR^{13}R^{14}$, $-C(NR^{13})NR^{14}R^{15}$, $-SO_3R^{13}$, $-SO_2R^{13}$, $-SO_2NR^{13}R^{14}$, $-PO_3{}^{13}R^{14}$, $-POR^{13}R^{14}$, $-PO(NR^{13}R^{14})_2$;

$R^9$ and $R^{10}$ are independently hydrogen, or lower alkyl, optionally substituted with up to 3 groups selected from the group consisting of halogen, amino, mono- or dialkylamino, hydroxy, lower alkoxy, phenyl or substituted phenyl, or when taken together with the nitrogen to which they are attached, $R^9$ and $R^{10}$ form a ring having from 3–7 members, up to four of which may be selected from

O, S, and $NR^{20}$, where $R^{20}$ is hydrogen, lower alkyl, or —CO lower alkyl;

$R^{11}$ is a heteroaryl or a heterocyclic group;

$R^{12}$ is a cycloalkyl, a heterocyclic, an aryl, or a heteroaryl group;

n is 0, 1, 2, or 3;

and the pharmaceutically acceptable salts, esters, amides, and prodrugs thereof.

The present invention also provides a composition that comprises a compound of Formula I together with a pharmaceutically acceptable carrier, diluent, or excipient.

The present invention also provides methods for inhibiting cyclin-dependent kinase and growth factor-mediated kinase enzymes.

The present invention also provides a method of treating subjects suffering from diseases caused by cellular proliferation. The method comprises inhibiting proliferation of tumorigenic cells of epithelial origin and vascular smooth muscle proliferation and/or cellular migration by administering a therapeutically effective amount of a compound of Formula I to a subject in need of treatment.

The present invention also provides a method of treating subjects suffering from diseases caused by DNA tumor viruses, such as herpes viruses comprising administering a compound of Formula I.

DETAILED DESCRIPTION OF THE INVENTION

The compounds encompassed by the instant invention are those described by the general Formula I set forth above, and the pharmaceutically acceptable salts, esters, amides, and prodrugs thereof.

In addition to the compounds of Formula I, the invention provides preferred compounds of Formula II:

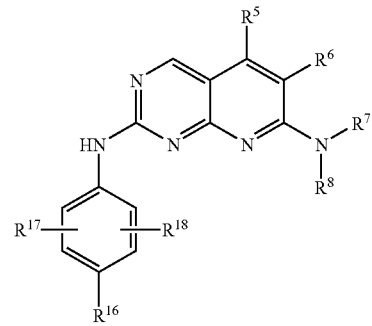

wherein $R^5$, $R^6$, $R^7$, and $R^8$ are as defined above for Formula I;

$R^{16}$, $R^{17}$, and $R^{18}$ are as defined above for the $(CH_2)_nR^{12}$ substituents, and preferably are independently hydrogen, halogen, amino, mono- or dialkylamino, hydroxy, lower alkyl, lower alkoxy, cyano, nitro, carboxy, carboxyalkyl, aminocarbonyl, mono- or dialkylaminocarbonyl, alkylcarbonyl, $-SO_3R^9$, $-SO_2NR^9R^{10}$, $-SO_2R^9$, $-SR^9$, $-PO_3R^9R^{10}$, $-POR^9R^{10}$, $-PO(NR^9R^{10})_2$, $-NR^9COR^{10}$, $-NR^9CO_2R^{10}$, $-NR^9CONR^9R^{10}$, $-NR^9SO_2R^{10}$; or $R^{16}$ is a carbocyclic group containing from 3–7 members, up to 2 of which members are heteroatoms selected from oxygen and nitrogen, wherein the carbocyclic group is unsubstituted or substituted with 1, 2, or 3 groups as defined above, but preferably are independently selected from the group consisting of halogen, hydroxy, lower alkyl, trifluoromethyl, lower alkoxy, amino, mono- or dialkylamino, aryl, heteroaryl, arylalkyl, heteroarylalkyl, heteroarylsulfonyl, heteroarylsulfonylalkly, heterocyclylalkyl, heterocyclylsulfonyl, or heterocyclylsulfonylalkyl.

Preferred compounds of Formula II are where $R^5$ is hydrogen or lower alkyl; $R^6$ is hydrogen, lower alkyl, cyano or halogen; $R^{17}$ and $R^{18}$ are independently hydrogen, halogen, amino, mono- or dialkylamino, hydroxy, lower alkyl, lower alkoxy, aminocarbonyl, mono- or dialkylaminocarbonyl, $-SO_2NR^9R^{10}$ or $-NR^9COR^{10}$; and $R^{16}$ is optionally substituted N-piperidine, N-piperazine, or N-pyrrolidine, for instance where the ring substituents are selected from $-R^9$, $-NR^9R^{10}$, $-OR^9$, $NR^9COR^{10}$, and $COR^{10}$.

In addition, the present invention also provides preferred compounds of Formula III:

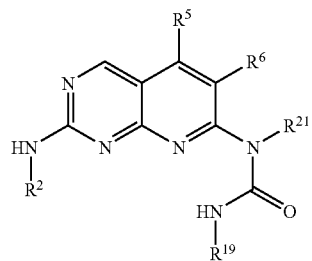

wherein $R^2$, $R^5$, and $R^6$ are as defined above for Formula I; and $R^{19}$ is hydrogen, or lower alkyl, lower alkenyl, or lower alkynyl, each of which is optionally substituted with up to 5 groups independently selected from halogen, amino, mono- or dialkylamino, hydroxy, lower alkoxy, cyano, nitro, carboxy, carboxyalkyl, aminocarbonyl, mono- or dialkylaminocarbonyl, lower alkylcarbonyl, —SO$_3$R$^9$, —SO$_2$NR$^9$R$^{10}$, —SO$_2$R$^9$, —SR$^9$, —PO$_3$R$^9$R$^{10}$, —POR$^9$R$^{10}$, —PO(NR$^9$R$^{10}$)$_2$, —NR$^9$COR$^{10}$, —NR$^9$CO$_2$R$^{10}$, —NR$^9$CONR$^9$R$^{10}$, —NR$^9$SO$_2$R$^{10}$, where R$^9$ and R$^{10}$ are as defined above, or aryl, heteroaryl, arylalkyl, heteroarylalkyl, cycloalkyl or cycloalkyl-alkyl, where each aryl, heteroaryl or cycloalkyl group is optionally substituted with up to 5 groups independently selected from halogen, amino, mono- or dialkylamino, hydroxy, lower alkoxy, cyano, nitro, carboxy, carboxyalkyl, aminocarbonyl, mono- or dialkylaminocarbonyl, alkylcarbonyl, —SO$_3$R$^9$, —SO$_2$NR$^9$R$^{10}$, —SO$_2$R$^9$, —SR$^9$, —PO$_3$R$^9$R$^{10}$, —POR$^9$R$^{10}$, —PO(NR$^9$R$^{10}$)$_2$, —NR$^9$COR$^{10}$, —NR$^9$CO$_2$R$^{10}$, —NR$^9$CONR$^9$R$^{10}$, —NR$^9$SO$_2$R$^{10}$, or a (CH$_2$)$_n$-carbocyclic group containing from 3–7 members, up to 2 of which members are heteroatoms selected from oxygen and nitrogen, wherein the carbocyclic group is unsubstituted or substituted with 1, 2, or 3 groups independently selected from the group consisting of halogen, hydroxy, lower alkyl, trifluoromethyl, lower alkoxy, amino, mono- or dialkylamino, aryl, heteroaryl, arylalkyl, heteroarylalkyl, heteroarylsulfonyl, heteroarylsulfonylalkyl, heterocyclylalkyl, heterocyclylsulfonyl, or heterocyclylsulfonylalkyl; and R$^{21}$ is hydrogen, lower alkyl, or lower alkyl substituted with phenyl or substituted phenyl.

Preferred compounds of Formula III are where R$^5$ is hydrogen or lower alkyl, R$^6$ is hydrogen or halogen, R$^2$ is optionally substituted phenyl; R$^{21}$ is hydrogen or methyl; and R$^{19}$ is optionally substituted lower alkyl, cycloalkyl, or (CH$_2$)$_n$-carbocyclic.

An especially preferred group of pyrido[2,3-d] pyrimidines have Formula IV:

IV

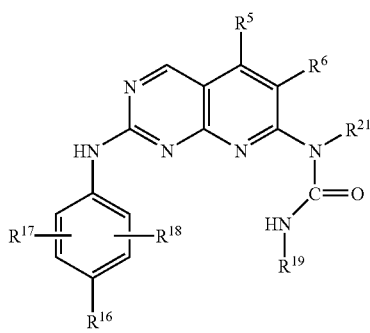

wherein R$^5$, R$^6$, R$^{16}$, R$^{17}$, R$^{18}$, R$^{19}$, and R$^{21}$ are as defined above. Preferred compounds of Formula IV are those wherein R$^{21}$ is hydrogen or methyl.

Another especially preferred group of invention compounds have Formula V:

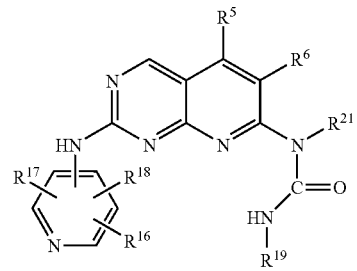

wherein R$^5$, R$^6$, R$^{16}$, R$^{17}$, R$^{18}$, R$^{19}$, and R$^{21}$ are as defined above. Preferred compounds of Formula V are those wherein R$^{21}$ is hydrogen or methyl.

The most preferred invention compounds have Formula VI

VI

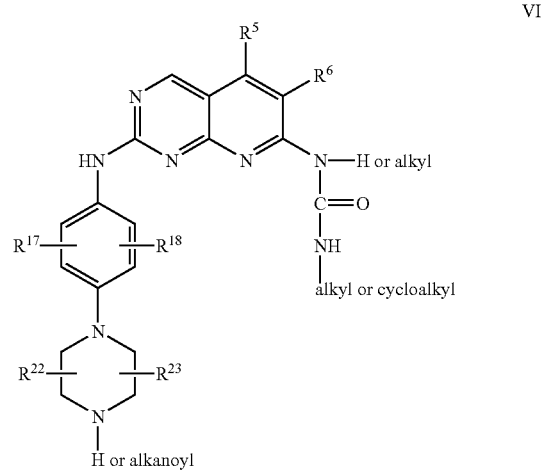

wherein R$^5$, R$^6$, R$^{17}$, and R$^{18}$ are as defined above, and R$^{22}$ and R$^{23}$ independently are hydrogen or alkyl.

By "alkyl," "lower alkyl," and "(C$_1$–C$_{10}$)-alkyl" in the present invention is meant straight or branched chain alkyl groups having 1 to 10 carbon atoms, preferably C$_1$–C$_6$ alkyl. Typically alkyl groups include methyl, ethyl, n-propyl, isopropyl, n-butyl, sec-butyl, tert-butyl, pentyl, 2-pentyl, isopentyl, neopentyl, hexyl, 2-hexyl, 3-hexyl, decyl, octyl, and 3-methylpentyl. These groups may be substituted, for instance with halo, C$_1$–C$_3$ alkyl, amino, alkylamino, dialkylamino, hydroxy, alkoxy, and the like. Examples include chloromethyl, 2-amino-ethyl, and 3-dimethylaminopropyl.

By "alkenyl," "lower alkenyl," and (C$_2$–C$_{10}$)-alkenyl is meant straight or branched chain alkyl groups having 1 to 10 carbon atoms and having 1 or 2 nonadjacent double bonds. Examples of alkenyls include, but are not limited to, 3-butenyl and 1-methyl-3-pentenyl.

By "alkynyl," "lower alkynyl," and (C$_2$–C$_{10}$)-alkynyl is meant straight or branched chain alkyl groups having 1 to 10 carbon atoms and having a triple bond. Typical alkynyl groups include 2-propynyl and 1,1-dimethyl-3-butynyl. Substituted alkenyl and alkynyl groups include 4,4-dibromo-2-pentenyl and 3-amino-5-hexynyl.

By "alkoxy," "lower alkoxy," or "(C$_1$–C$_{10}$)-alkoxy" in the present invention is meant straight or branched chain alkoxy groups having 1 to 10 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

The term "alkanoyl" means an alkyl group bonded through a carbonyl moiety. Examples include acetyl and pentanoyl. "Aminoalkanoyl" means the alkyl group is substituted with an amino group. Examples include aminoacetyl and 3-aminohexanoyl. "Alkylaminoalkanoyl" means an aminoalkanoyl group wherein the amine is substituted with a $C_1$–$C_{10}$ alkyl group, and includes methylaminoacetyl and 4-(isobutylamino)-octanoyl. "Dialkylaminoalkanoyl" means an N,N-di-substituted aminoalkanoyl group such as diisopropylaminoacetyl.

By halogen in the present invention is meant fluorine, bromine, chlorine, and iodine.

The term "aryl" means an unsubstituted aromatic carbocyclic group having a single ring (e.g., phenyl), multiple rings (e.g., biphenyl), or multiple condensed rings in which at least one is aromatic (e.g., 1,2,3,4-tetrahydronaphthyl, naphthyl, anthryl, or phenanthryl). The term "substituted aryl" means an aryl substituted by 1 to 4 substituents selected from alkyl, O-alkyl and S-alkyl, —OH, —SH, —CN, halo, 1,3-dioxolanyl, —$CF_3$, —$NO_2$, —$NH_2$, —$NHCH_3$, —$N(CH_3)_2$, —NHCO-alkyl, —$(CH_2)_mCO_2H$, —$(CH_2)_mCO_2$-alkyl, —$(CH_2)_mSO_3H$, —NH alkyl, —$N(alkyl)_2$, —$(CH_2)_mPO_3H_2$, —$(CH_2)_mPO_3(alkyl)_2$, —$(CH_2)_mSO_2NH_2$, and —$(CH_2)_mSO_2NH$-alkyl, wherein alkyl is defined as above and m is 0, 1, 2, or 3. Some examples of substituted aryl groups are methylphenyl, isopropoxyphenyl, chlorophenyl, 2-bromo-3-trifluoromethyl-4-nitro-5-aminophenyl, 4-bromobiphenyl, 3-acetamidonaphthyl, 3-dimethylaminoanthryl, 3,4-dimethoxyphenanthryl, and 2,8-dibromobiphenylen-1-yl.

By "heteroaryl" is meant one or more aromatic ring systems of 5-, 6-, or 7-members containing at least 1 and up to 4 heteroatoms selected from nitrogen, oxygen, or sulfur. Such heteroaryl groups include, for example, thienyl, furanyl, thiazolyl, imidazolyl, (is)oxazolyl, tetrazolyl, pyridyl, pyrazinyl, pyrimidinyl, pyrazolyl, (iso)quinolinyl, napthyridinyl, phthalimidyl, benzimidazolyl, benzoxazolyl. A "substituted heteroaryl" group can be substituted with 1, 2, 3, or 4 of the groups mentioned above for "substituted aryl," such as 2,3,4,6-tetrachloropyridyl and 2-methoxy-3-trifluoromethylthien-4-yl.

The term "heterocyclic group" means a non-aromatic ring having 5-, 6-, or 7-ring atoms, from 1 to 4 of which are selected from nitrogen, oxygen, or sulfur. Examples of heterocyclic groups include morpholino, piperidino, piperazino, pyrrolidinyl, and tetrahydrothienyl. Such groups can be substituted with the same groups described above for substituted heteroaryl.

A "carbocyclic group" or "cycloalkyl" is a nonaromatic cyclic ring or fused rings having from 3- to 7-ring carbon members. Examples include cyclopropyl, cyclobutyl, and cycloheptyl. These rings may be substituted with one or more of the substituent groups mentioned above for aryl, for example alkyl, halo, amino, hydroxy, and alkoxy. Typical substituted carbocyclic groups include 2-chlorocyclopropyl, 2,3-diethoxycyclopentyl, and 2,2,4,4-tetrafluorocyclohexyl. The carbocyclic group may contain 1 or 2 heteroatoms selected from oxygen, sulfur, and nitrogen, and such ring systems are referred to as "heterocyclyl" or "heterocyclic". Examples include piperidyl, piperazinyl, pyrrolidinyl, pyranyl, tetrahydrofuranyl, and dioxanyl. These heterocyclyl groups may be substituted with up to 4 of the substituent groups mentioned for aryl to give groups such as 3,5-dimethylpiperazin-1-yl, 3,3-diethylpiperazin-1-yl, 3,3,4,4-tetramethylpyrrolidinyl, 3-chloro-2-dioxanyl, and 3,5-dihydroxymorpholino. These can also bear a keto group, for instance, 3-ketopiperidyl.

The term "cancer" includes, but is not limited to, the following tumor types: breast, ovary, cervix, prostate, testis, esophagus, glioblastoma, neuroblastoma, stomach, skin, keratoacanthoma, lung, epidermoid carcinoma, large cell carcinoma, adenocarcinoma, bone, colon, adenoma, pancreas, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cell carcinoma, cancer of the buccal cavity and pharynx (oral), lip, tongue, mouth, pharynx, small intestine, colon, rectum, large intestine, brain and central nervous system; and leukemia.

The compounds of Formulas I to VI can exist as pharmaceutically acceptable salts, esters, amides, and prodrugs. The term "pharmaceutically acceptable salts, esters, amides, and products" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic, and organic acid addition salts and base salts of compounds of the above formulas. These salts can be prepared in situ during the final isolation and purification of the compounds, or by separately reacting the purified compound in its free base form, for example, with a suitable organic or inorganic acid, and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, and laurylsulphonate salts, and the like. When the compound of the above formulas has one or more acidic groups, it can form a salt by reaction with a base. These salts may include cations based on the alkali and alkaline earth metals, such as sodium, lithium, potassium, calcium, magnesium, and the like, as well as inorganic bases such as ammonium, quaternary ammonium, and other amine cations including, tetramethylammonium, tetraethylammonium, methylamine, dimethylamine, trimethylamine, triethylamine, ethylamine, and the like. Pharmaceutically acceptable salts are well-known to those skilled in the art of medicinal chemistry. (See, for example, Berge S. M. et al., "Pharmaceutical Salts," *J. Pharm. Sci.*, 1977; 66:1–19 which is incorporated herein by reference.)

Examples of pharmaceutically acceptable, nontoxic esters of the compounds of this invention include $C_1$–$C_6$ alkyl esters, wherein the alkyl group is a straight or branched hydrocarbon, substituted or unsubstituted. Esters also include $C_5$–$C_7$ cycloalkyl esters, as well as arylalkyl esters such as benzyl and triphenylmethyl, $C_1$–$C_4$ Alkyl esters are preferred, such as methyl, ethyl, 2,2,2-trichloroethyl, and tert-butyl. Esters of the compounds of the present invention may be prepared according to conventional methods, for example by reaction of an acid with an alcohol.

Examples of pharmaceutically acceptable amides of the compounds of this invention include amides derived from ammonia, primary $C_1$–$C_6$ alkyl amines and secondary $C_1$–$C_6$ dialkyl amines, wherein the alkyl groups are straight or branched. In the case of secondary amines, the amine may also be in the form of a 5- or 6-membered heterocycle containing 1 nitrogen atom. Amides derived from ammonia, $C_1$–$C_3$ alkyl primary amines, and $C_1$–$C_2$ dialkyl secondary amines are preferred. Amides of the compounds of the invention may be prepared according to conventional methods well-known to the medicinal chemists.

The term "prodrug" refers to compounds that are rapidly transformed in vivo to yield the parent compound of the above formulae, for example, by hydrolysis in blood or stomach fluids. A thorough discussion of prodrugs is provided by Higuchi T. and Stella V., "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference.

Representative compounds of the invention are shown below in Table 1.

Table 1

1

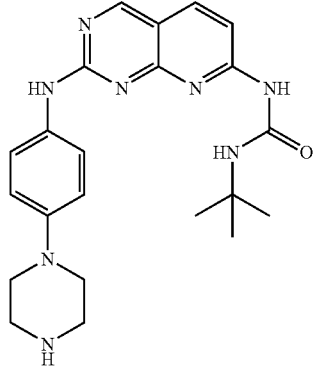

2

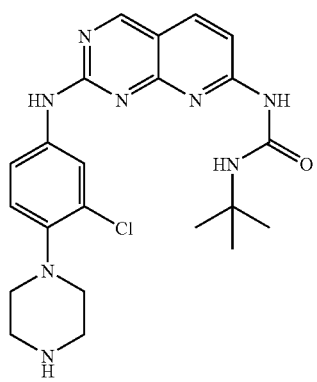

3

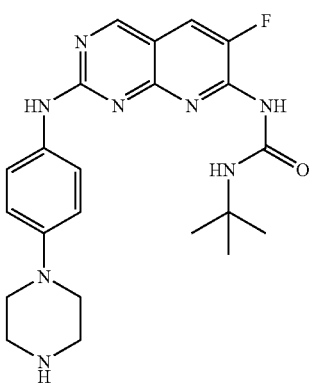

4

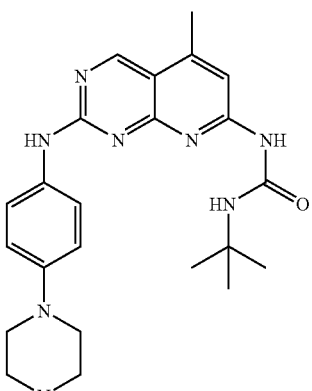

5

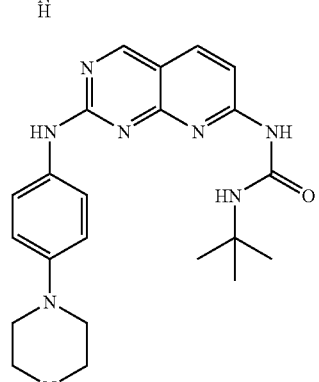

6

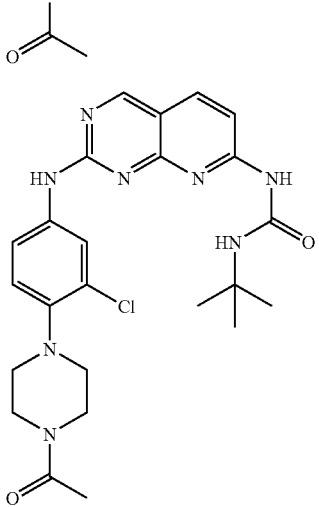

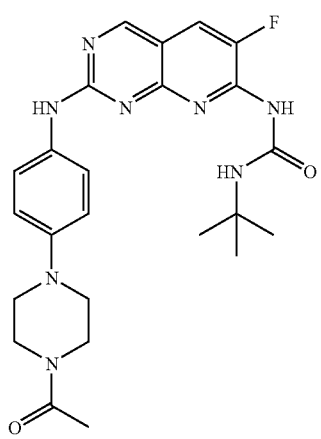
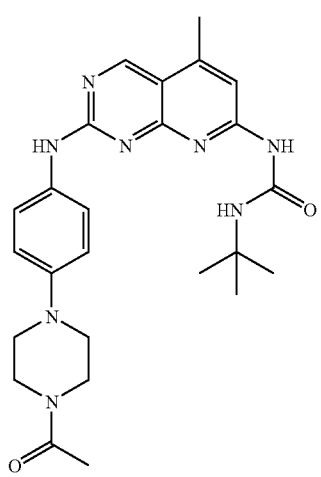
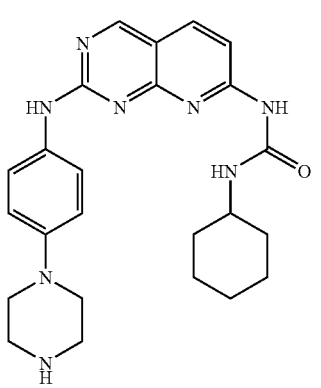
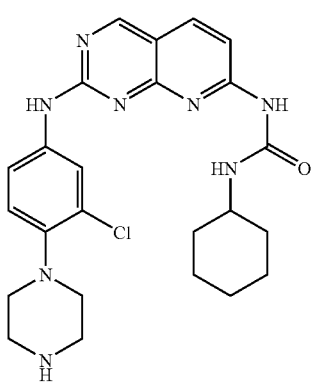
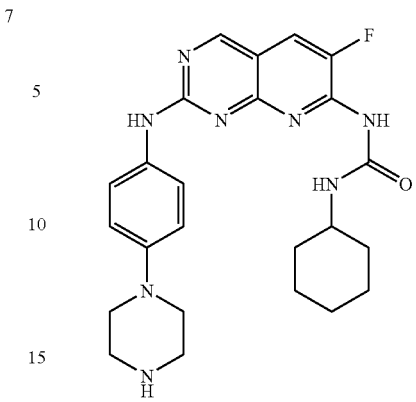
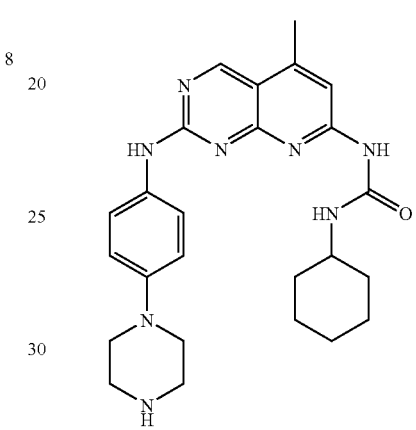
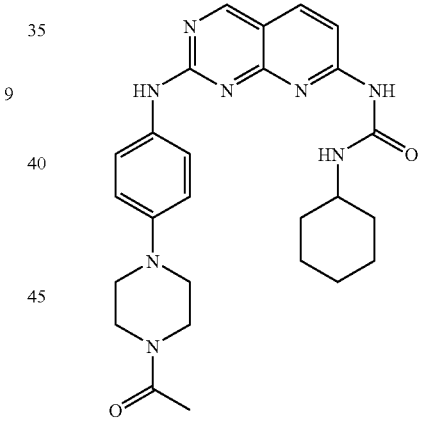
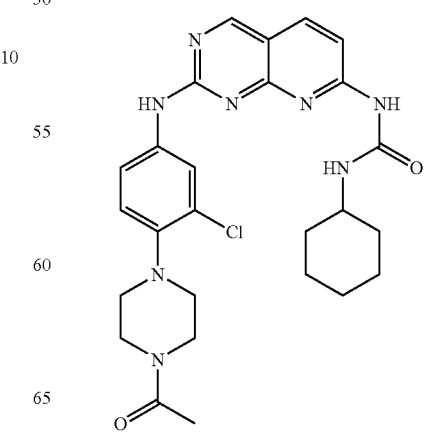

13
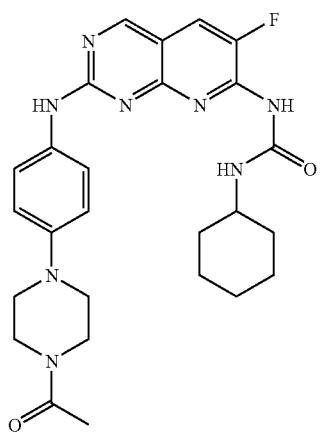
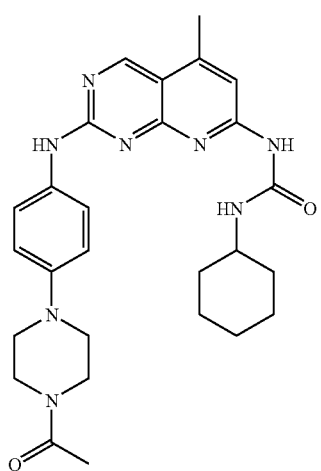
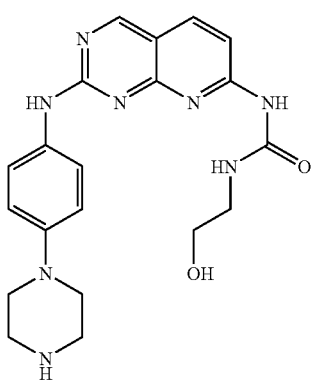
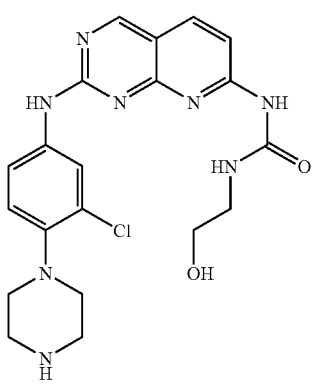
14
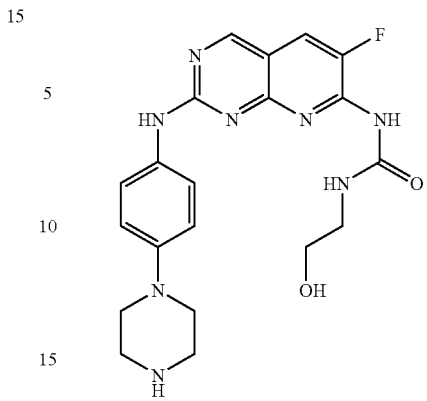
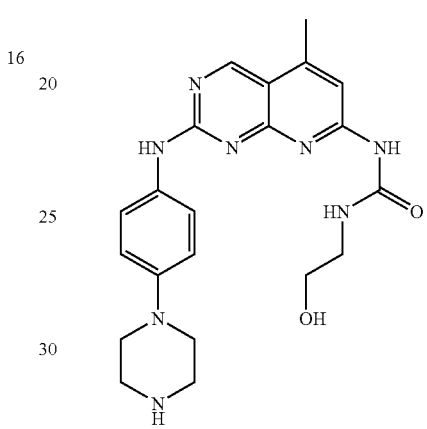
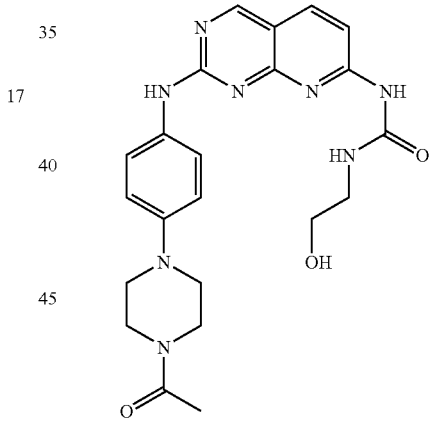
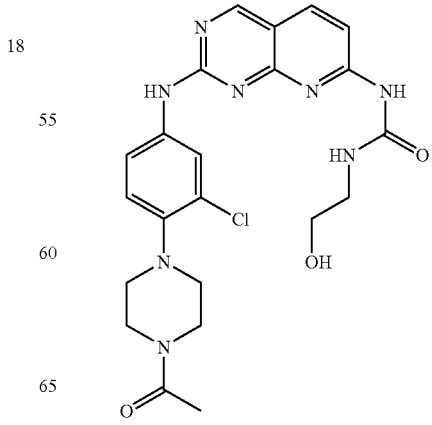

23
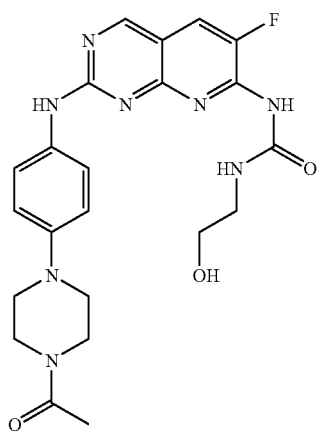
24
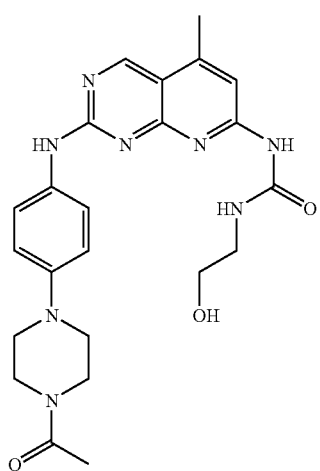
25
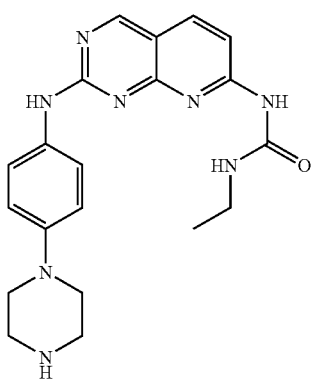
26
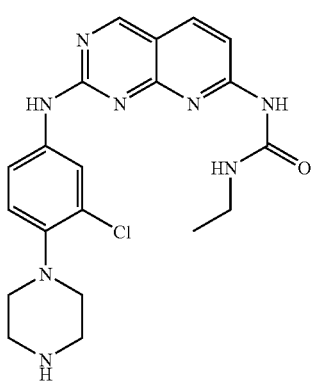
27
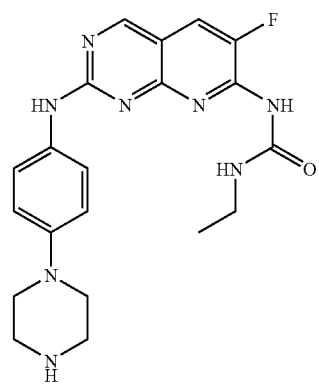
28
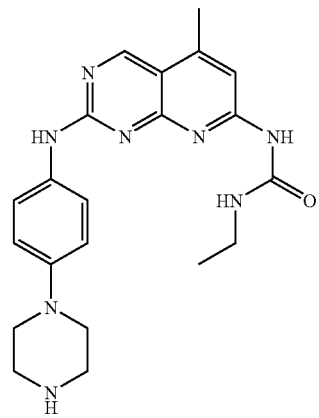
29
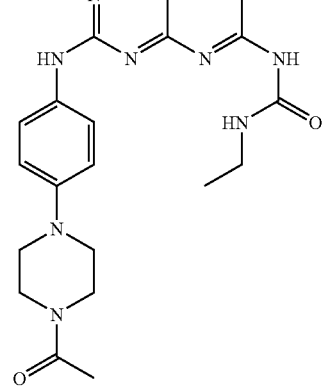
30
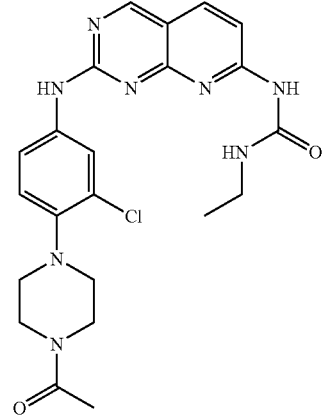

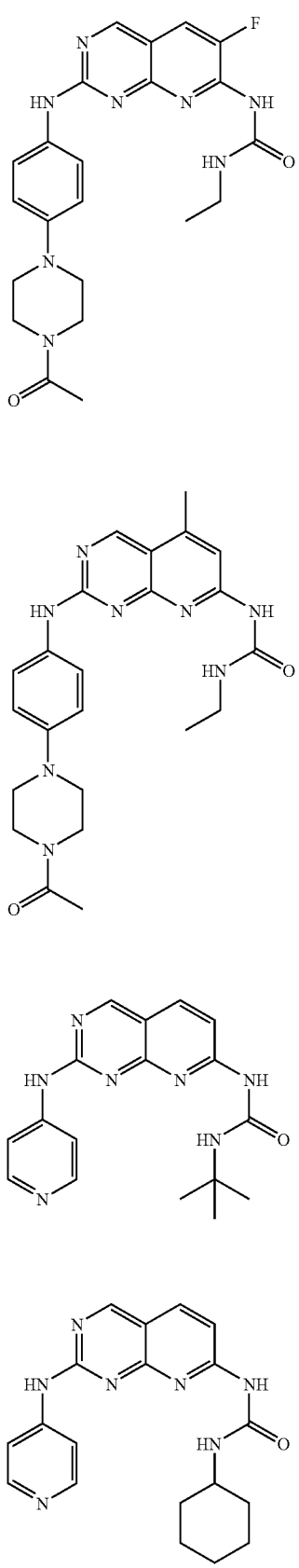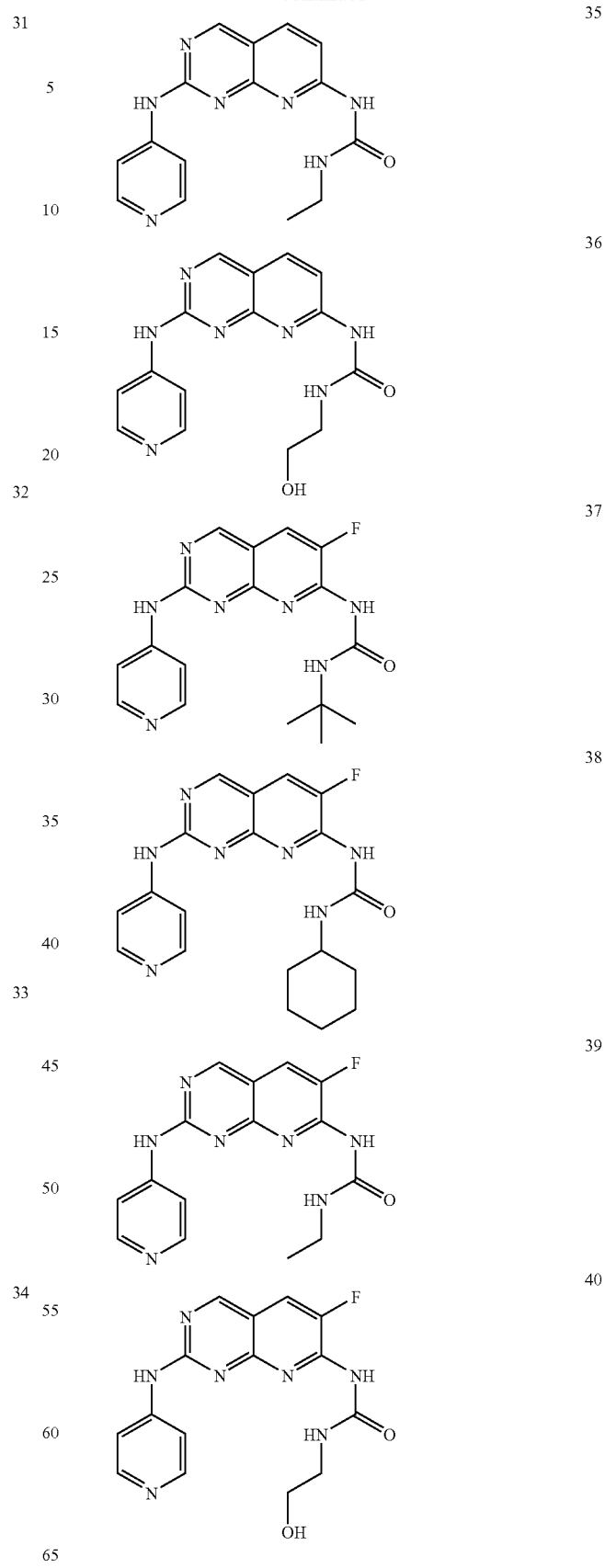

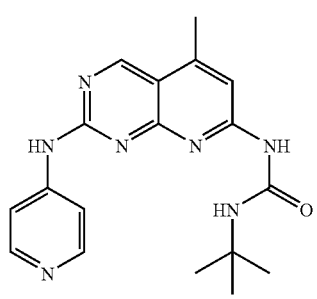
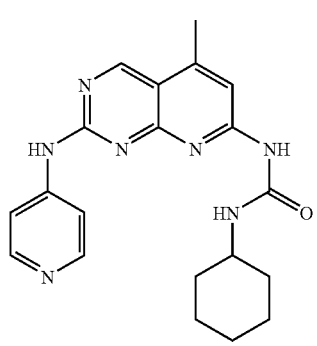
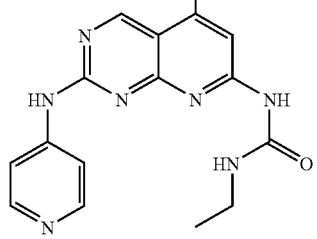
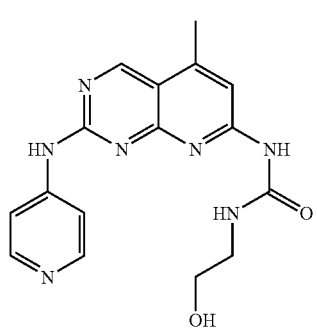
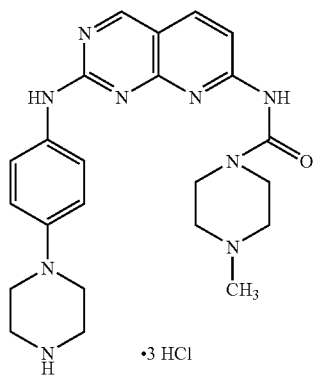
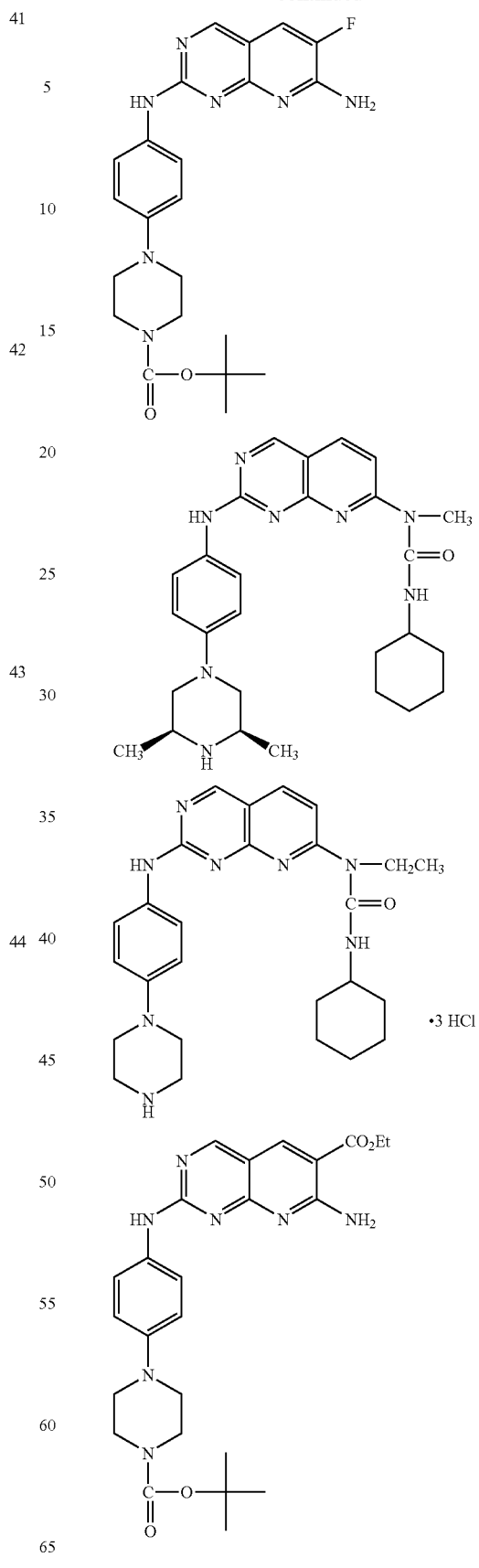

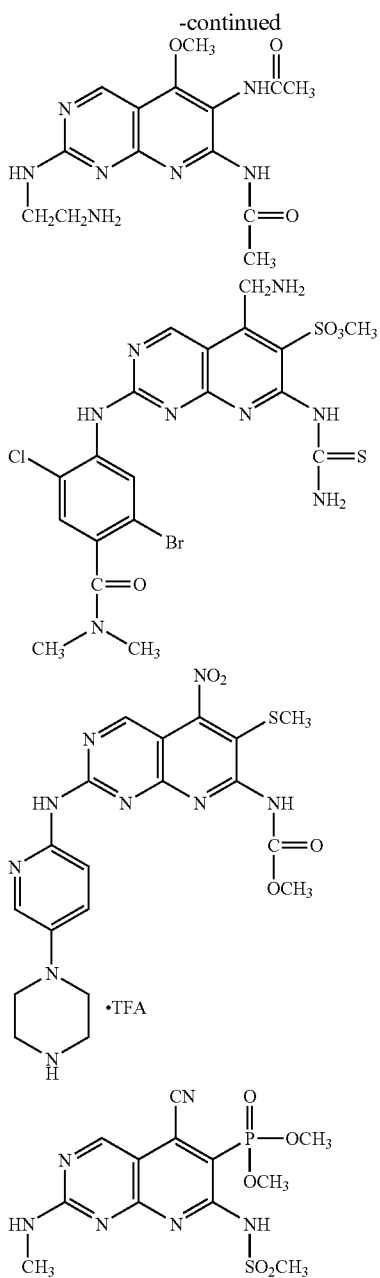

Representative compounds of the present invention, which are encompassed by Formula I, include, but are not limited to, the compounds in Table 1 and their pharmaceutically acceptable acid or base addition salts, ester or amide analogs, and prodrugs thereof.

The compounds of the present invention can exist in unsolvated forms as well as solvated forms, including hydrated forms. In general, the solvated forms, including hydrated forms, are equivalent to unsolvated forms and are intended to be encompassed within the scope of the present invention.

Some of the compounds of Formula I have one or more chiral centers, and can thus exist as individual stereoisomers and mixtures thereof. Other compounds can exist in more than one geometric form. This invention includes all optical and geometric isomers and forms, and mixtures thereof. Racemic mixtures of invention compounds are readily resolved into individual isomers by routine methods such as chromatography, fractional crystallization, and classical resolution using optically active acids and salts. The individual isomers can also be prepared by chiral synthesis, including chiral hydrogenations and the like using commercially available chiral catalysts.

The compounds of the present invention are useful for treating cancer (for example, leukemia, and cancer of the lung, breast, prostate, and skin such as melanoma) and other proliferative diseases, including, but not limited to, psoriasis, HSV, HIV, restenosis, and atherosclerosis. To utilize a compound of the present invention to treat cancer, a patient having cancer is administered a therapeutically effective amount of a pharmaceutically acceptable composition comprising an invention compound.

A further embodiment of this invention is a method of treating patients suffering from diseases caused by vascular smooth muscle cell proliferation. Compounds within the scope of the present invention effectively inhibit vascular smooth muscle cell proliferation and migration. The method entails inhibiting vascular smooth muscle proliferation, and/or migration by administering an effective amount of a compound of Formulas I to VI to a subject in need of treatment. "Subject" and "patient", as used herein, is a mammal such as a human, but also includes horses, cattle, sheep, and companion animals such as dogs and cats.

The compounds of the present invention can be formulated and administered in a wide variety of oral and parenteral dosage forms, including transdermal and rectal administration. It will be recognized to those skilled in the art that the following dosage forms may comprise as the active component, either a compound of Formula I or a corresponding pharmaceutically acceptable salt or solvate of a compound of Formula I.

A further embodiment of this invention is a pharmaceutical composition comprising a compound of Formulas I to VI together with a pharmaceutically acceptable carrier, diluent, or excipient therefor. For preparing pharmaceutical compositions with the compounds of the present invention, pharmaceutically acceptable carriers can be either a solid or liquid. Solid form preparations include powders, tablets, pills, capsules, cachets, suppositories, and dispensable granules. A solid carrier can be one or more substances which may also act as diluents, flavoring agents, binders, preservatives, tablet disintegrating agents, or an encapsulating material.

In powders the carrier is a finely divided solid such as talc or starch which is in a mixture with the finely divided active component. In tablets, the active component is mixed with the carrier having the necessary binding properties in suitable proportions and compacted in the shape and size desired.

The formulations of this invention preferably contain from about 5% to about 70% or more of the active compound. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. A preferred form for oral use are capsules, which include the formulation of the active compound with encapsulating material as a carrier providing a capsule in which the active component with or without other carriers, is surrounded by a carrier, which is thus in association with it. Similarly, cachets and lozenges are included. Tablets, powders capsules, pills, cachets, and lozenges can be used as solid dosage forms suitable for oral administration.

For preparing suppositories, a low melting wax, such as a mixture of fatty acid glycerides or cocoa butter, is first melted, and the active component is dispersed homogeneously therein, as by stirring. The molten homogenous mixture is then poured into convenient size molds, allowed to cool, and thereby to solidify.

Liquid form preparations include solutions, suspensions, and emulsions such as water or water/propylene glycol solutions. For parenteral injection, liquid preparations can be formulated in solution in aqueous polyethylene glycol solution, isotonic saline, 5% aqueous glucose, and the like. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water and mixing with a viscous material, such as natural or synthetic gums, resins, methylcellulose, sodium carboxymethylcellulose, or other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like. Waxes, polymers, microparticles, and the like can be utilized to prepare sustained-release dosage forms. Also, osmotic pumps can be employed to deliver the active compound uniformly over a prolonged period.

The pharmaceutical preparations of the invention are preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form.

The therapeutically effective dose of a compound of Formula I will generally be from about 1 to about 100 mg/kg of body weight per day. Typical adult doses will be about 50 to about 800 mg per day. The quantity of active component in a unit dose preparation may be varied or adjusted from about 0.1 to about 500 mg, preferably about 0.5 to 100 mg according to the particular application and the potency of the active component. The composition can, if desired, also contain other compatible therapeutic agents. A subject in need of treatment with a compound of Formula I is administered a dosage of about 1 to about 500 mg per day, either singly or in multiple doses over a 24-hour period.

The compounds of the present invention are capable of binding to and inhibiting the activity of proteins having the ability to phosphorylate other proteins, such as cdks, PDGFr, FGFr, c-Src, and EGFr. Cdks form complexes with cyclins, and these complexes phosphorylate key proteins allowing cells to proceed through the cell cycle (Meijer L., *Progress in Cell Cycle Research*, 1995; 1:351–363). The compounds of this invention inhibit this phosphorylation and therefore can be used as anti-proliferative agents for the treatment of cancer and/or restenosis and other proliferative diseases.

Because of their inhibitor activity against cdks and other kinases, the compounds of the present invention are also useful research tools for studying the mechanism of action of those kinases, both in vitro and in vivo.

The preparation and use of the compounds of this invention are further described in the following detailed example. The examples are intended to illustrate particular embodiments of the invention, and are not intended to limit the scope of the specification or the claims in any way. The invention compounds are prepared by synthetic methodologies well-known to those skilled in the art of organic chemistry, and utilize commercially available starting materials and reagents.

It may be desirable during the synthesis of an invention compound to derivatize reactive functional groups in the molecule undergoing reaction so as to avoid unwanted side reactions. Functional groups such as hydroxy, amino, and acid groups typically are protected with suitable groups that can be readily removed when desired. Use of common protecting groups is described fully by Green and Wuts in *Protective Groups in Organic Synthesis*, John Wiley and Sons, New York, N.Y. (2$^{nd}$ Edition, 1991). Typical hydroxy protecting groups include ether forming groups such as benzyl, and aryl groups such as tert-butoxycarbonyl (Boc), formyl, and acetyl. Amino protecting groups include benzyl, aryl such as acetyl, and trialkylsilyl groups. Carboxylic acid groups typically are protected by conversion to an ester that can be easily hydrolyzed, for example, trichloroethyl, tert-butyl, benzyl, and the like.

As noted above, some of the invention compounds have one or more chiral centers, and thus can exist as individual optical isomers and geometric isomers, and mixtures thereof. Compound 106, for example, has two asymmetric centers, and has the cis configuration. This invention includes all such geometric isomers, enantiomers and RS racemates, as well as the individual R or S isomers of chiral compounds. All individual isomers and mixtures thereof are included in this invention. Individual isomers are readily prepared by a chiral synthesis or by conventional resolution techniques well-known to those skilled in the art.

An illustration of the preparation of compounds of the present invention is shown in Schemes 1–4. The synthesis of Compound 1 (Example 15) is depicted in Scheme 1; however, it should be recognized that the general scheme is applicable to all of the invention compounds. Each step shown in the Schemes is further illustrated in the detailed examples that follow.

In Scheme 1, a 2-methylthio-4-halo-5-alkoxycarbonylpyrimidine is reacted with ammonium hydroxide to give the corresponding 4-amino derivative. The ester is reduced by reaction by reaction with LiAlH$_4$ to give the 5-hydroxymethyl analog, which in turn is oxidized to a 5-formyl derivative. The 5-formyl group is converted to an unsaturated (acrylate) group, which is cyclized to form a pyrido[2,3-d]pyrimidine. The pyridopyrimidine is converted to a key intermediate, namely 2-methylsulfanyl-pyrido[2,3-d]pyrimidine-7-ylamine, which is readily oxidized to give a 2-methylsulfinyl analog. The 2-methylsulfinyl group is easily displaced by reaction with an amine R$_2$NH$_2$ to provide the invention compounds of Formula I. The 7-amino group on the pyridopyrimidine ring is readily converted to a urea by reaction with an isocyanate such as R$^{19}$N=C=O.

Scheme 1

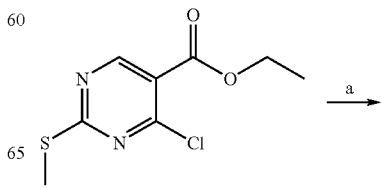

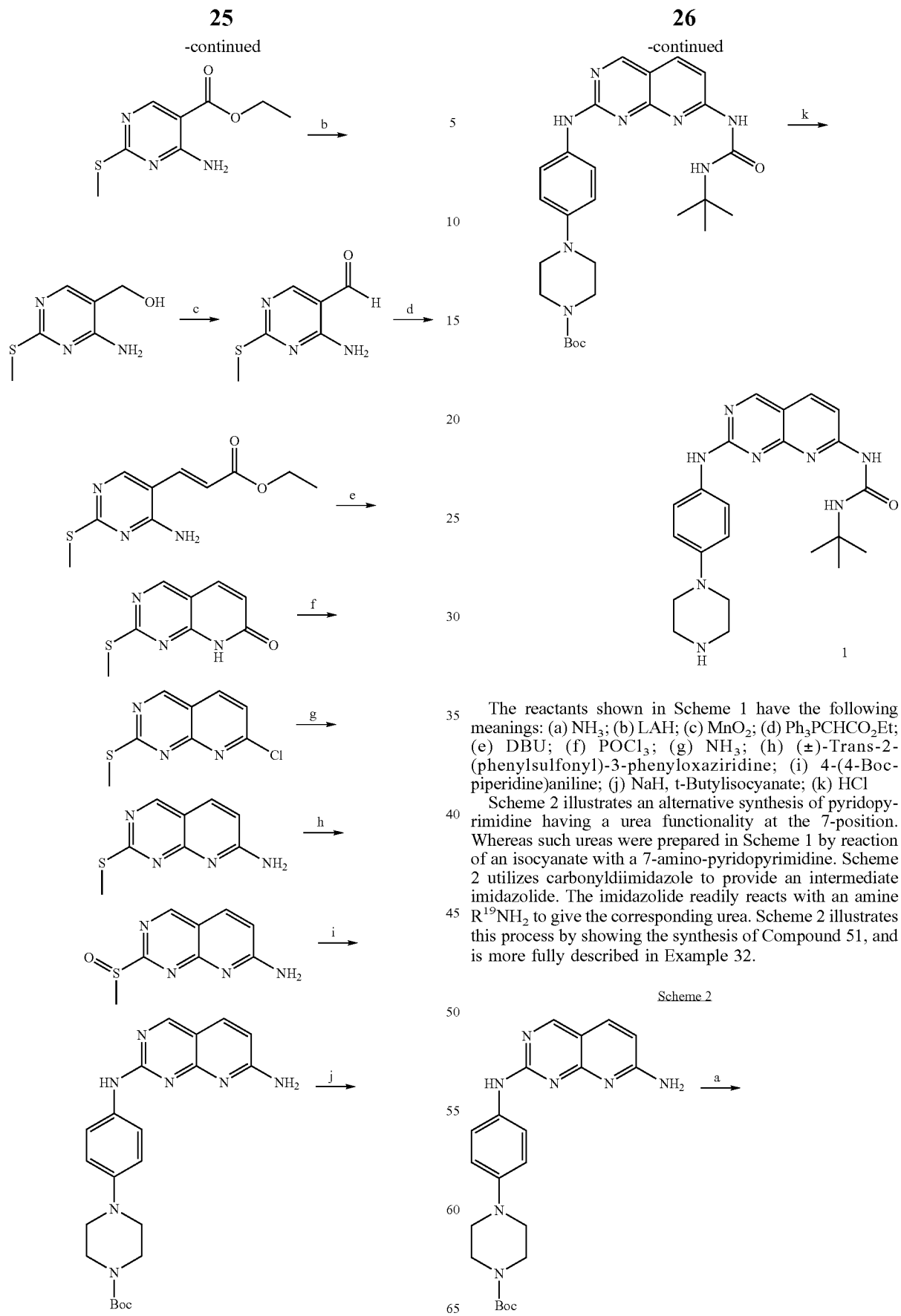

The reactants shown in Scheme 1 have the following meanings: (a) NH₃; (b) LAH; (c) MnO₂; (d) Ph₃PCHCO₂Et; (e) DBU; (f) POCl₃; (g) NH₃; (h) (±)-Trans-2-(phenylsulfonyl)-3-phenyloxaziridine; (i) 4-(4-Boc-piperidine)aniline; (j) NaH, t-Butylisocyanate; (k) HCl Scheme 2 illustrates an alternative synthesis of pyridopyrimidine having a urea functionality at the 7-position. Whereas such ureas were prepared in Scheme 1 by reaction of an isocyanate with a 7-amino-pyridopyrimidine. Scheme 2 utilizes carbonyldiimidazole to provide an intermediate imidazolide. The imidazolide readily reacts with an amine R¹⁹NH₂ to give the corresponding urea. Scheme 2 illustrates this process by showing the synthesis of Compound 51, and is more fully described in Example 32.

Scheme 2

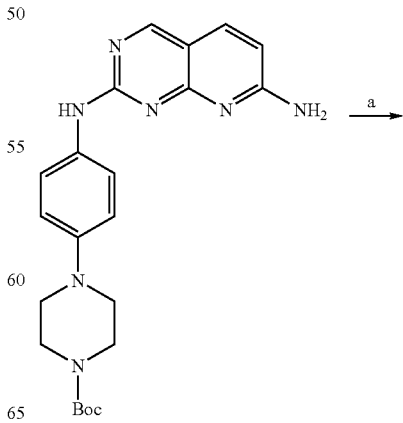

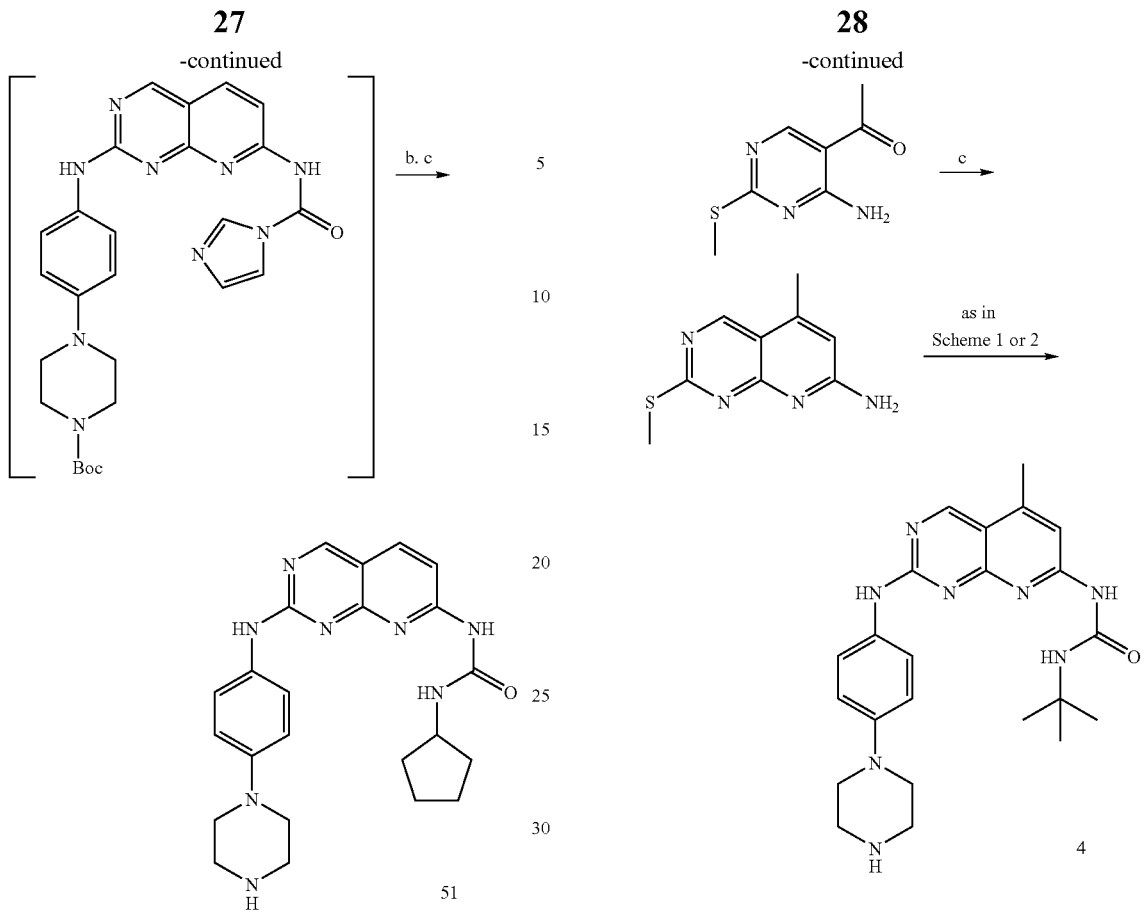

Conditions: (a) NaH, Carbonyldiimidazole; (b) Cyclopentylamine; (c) HCl

Compounds of Formula I may also be prepared according to Scheme 3, wherein the synthesis of compound 4 (Example 45) is depicted. 4-Amino-2-methanesulfanyl-pyrimidine-5-carboxaldehyde is reacted with methyl magnesium bromide to give the corresponding 5-(2-hydroxyethyl)-pyrimidine. The alcohol is oxidized to give the methyl ketone analog. The methyl ketone is reacted with diethyl cyanomethyl phosphonate and cyclized to a 5-methyl-7-amino-pyridopyrimidine. Further reaction as in Schemes 1 or 2 gives invention compounds such as compound 4.

Conditions: (a) MeMgBr; (b) MnO$_2$; (c) (EtO)$_2$P(O)CH$_2$CN

Compounds of Formula I may also be prepared according to Scheme 4, wherein the synthesis of compound 12 (Example 40) is depicted. In this scheme, the 2-methylthio group of a pyrimidine is first oxidized to the corresponding methylsulfinyl analog. The methylsulfinyl group is displaced by reaction with an amine R$^2$NH$_2$. The 5-carboxaldehyde is then derivatized as in Scheme 1 and cyclized to give the corresponding 2-(R$^2$NH) substituted 7-amino pyridopyrimidine. The 7-amino group is arylated or otherwise derivatized as illustrated in Schemes 1–3.

Scheme 3

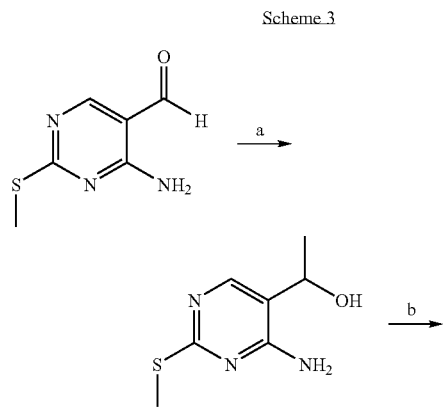

Scheme 4

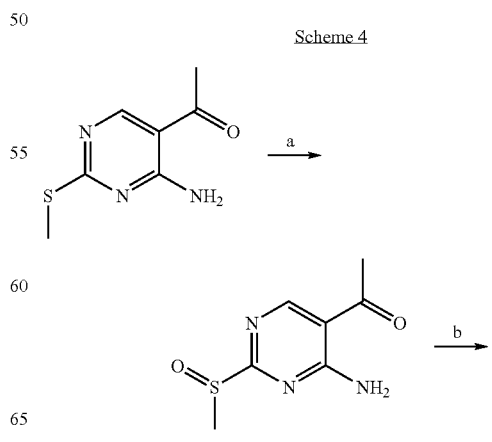

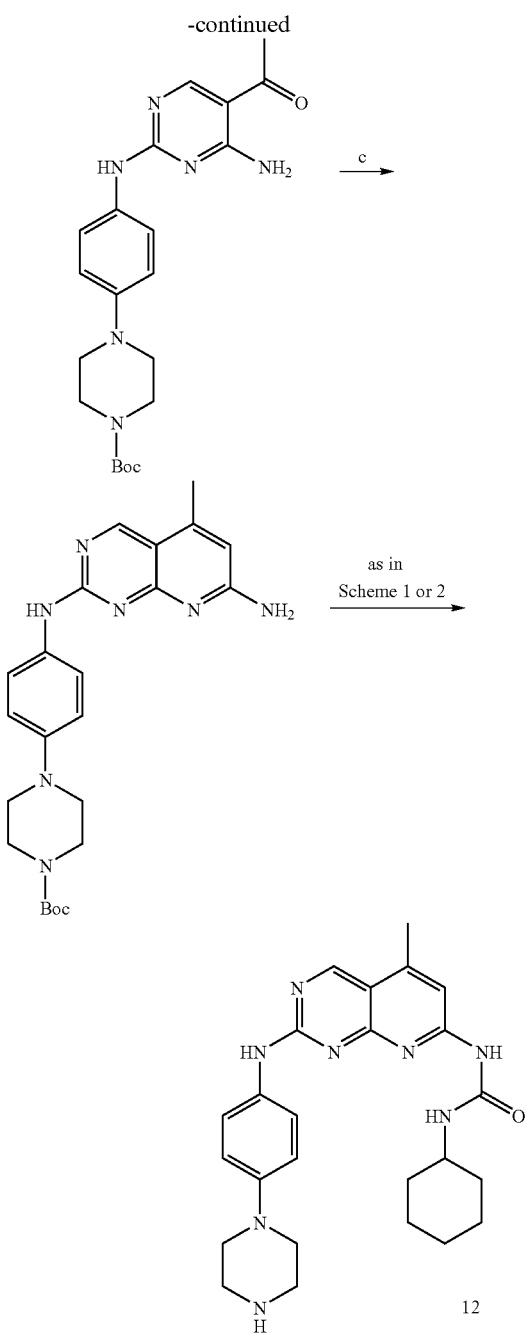

Conditions: (a) (±)-Trans-2-(phenylsulfonyl)-3-phenyloxaziridine; (b) 4-(4-Boc-piperidine)-aniline; (c) (EtO)₂P(O)CH₂CN Any of the invention compounds of Formulas I–VI may be prepared according to Schemes 1–4, wherein the synthesis of compounds 1, 51, 4, and 12, respectively, are illustrated. Those having skill in the art of organic chemistry will recognize that the starting materials may be varied, and additional steps may be employed to produce compounds encompassed by the present invention, as demonstrated by the following specific examples.

The disclosures in this application of all articles and references, including patents, are incorporated herein by reference.

The invention is illustrated further by the following detailed examples which are not to be construed as limiting the invention in scope or spirit to the specific procedures described in them. The starting materials and various intermediates may be obtained from commercial sources, prepared from commercially available organic compounds, or prepared using well-known synthetic methods.

EXAMPLE 1

4-Amino-2-methanesulfanyl-pyrimidine-5-carboxylic acid ethyl ester

To a room temperature solution of 4-chloro-2-methanesulfanyl-pyrimidine-5-carboxylic acid ethyl ester (15.0 g, 65 mmol) in 200 mL of tetrahydrofuran is added 25 mL of triethylamine followed by 35 mL of aqueous ammonium hydroxide. After stirring at room temperature for 1.5 hours, an additional 30 mL of aqueous ammonium hydroxide is added, and stirring is continued for 1 hour. The reaction mixture is concentrated in vacuo and partitioned between ethyl acetate and saturated aqueous sodium bicarbonate. The organic layer is washed with brine, dried over magnesium sulfate, filtered, and concentrated in vacuo. Ethyl acetate and hexane are added, and the resultant solid is collected by filtration to provide 10.84 g (79%) of 4-amino-2-methanesulfanyl-pyrimidine-5-carboxylic acid ethyl ester.

EXAMPLE 2

(4-Amino-2-methanesulfanyl-pyrimidin-5-yl)-methanol

A solution of 4-amino-2-methanesulfanyl-pyrimidine-5-carboxylic acid ethyl ester (13.36 g, 63 mmol) in 250 mL of tetrahydrofuran is added dropwise to a room temperature suspension of lithium aluminum hydride (3.82 g, 100 mmol) in 250 mL of tetrahydrofuran. After 30 minutes, the reaction is cooled to 0° C., and isopropyl alcohol is added until bubbling diminishes. The reaction is quenched with 15 mL of water, 15 mL of 15% NaOH, and 50 mL of water, and the mixture is stirred for 1 hour. The white precipitate is removed by filtration and washed with ethyl acetate. The filtrate is concentrated in vacuo and 3:1 hexane:ethyl acetate is added. The solids are collected, washed with 3:1 hexane:ethyl acetate, followed by hexane. The solid is dissolved in ethyl acetate, and the solution is dried over magnesium sulfate. Filtration followed by concentration in vacuo gives 8.14 g (76%) of (4-amino-2-methanesulfanyl-pyrimidin-5-yl)-methanol.

Analysis calculated for $C_6H_9N_3OS$: C, 42.09; H, 5.30; N, 24.54. Found: C, 42.31; H, 5.24; N, 24.27.

EXAMPLE 3

4-Amino-2-methanesulfanyl-pyrimidine-5-carboxaldehyde

To (4-amino-2-methanesulfanyl-pyrimidin-5-yl)-methanol (8.14 g, 48 mmol) in 1 L of chloroform is added manganese oxide (33.13 g, 381 mmol). The suspension is stirred at room temperature overnight then filtered through celite and washed with 300 mL of chloroform. The filtrate is concentrated in vacuo to give 8.14 g (quantitative yield) of 4-amino-2-methanesulfanyl-pyrimidine-5-carboxaldehyde, mp 185–187° C. Literature mp=183–184° C., JOC, 1958; 23:1738.

Analysis calculated for $C_6H_7N_3OS$: C, 42.59; H, 4.17; N, 24.83. Found: C, 42.84; H 4.21; N, 24.73.

EXAMPLE 4

Ethyl 3-(4-Amino-2-methanesulfanyl-pyrimidin-5-yl)acrylate

To a room temperature solution of 4-amino-2-methanesulfanyl-pyrimidine-5-carboxaldehyde (4.08 g, 24.14 mmol) in 100 mL of tetrahydrofuran is added (carbethoxymethylene) triphenylphosphorane (10.80 g, 31 mmol). The reaction mixture is heated at reflux for 3 hours then stirred at room temperature overnight. The reaction mixture is concentrated in vacuo, and the residue is purified by flash chromatography, eluting with 1:1 ethyl acetate:hexane, to provide 4.30 g (75%) of ethyl 3-(4-amino-2-methanesulfanyl-pyrimidin-5-yl)acrylate; mp softens at 108° C.

Analysis calculated for $C_{10}H_{13}N_3O_2S$: C, 50.19; H, 5.48; N, 17.56. Found: C, 50.22; H, 5.45; N, 17.24.

EXAMPLE 5

2-Methanesulfanyl-8H-pyrido[2,3-d]pyrimidin-7-one

To a room temperature solution of ethyl 3-(4-amino-2-methanesulfanyl pyrimidin-5-yl)acrylate (368 mg, 1.53 mmol) in 3 mL of N,N-diisopropylethylamine is added 380 µL of 1,8-diazabicyclo[5.4.0]undec-7-ene. The reaction mixture is heated at reflux for 3 hours then cooled to room temperature and concentrated. The residue is purified by flash chromatography eluting with ethyl acetate. The fractions containing the product are partially concentrated in vacuo, and the solids are removed by filtration to provide 134 mg (45%) of 2-methanesulfanyl-8H-pyrido[2,3-d]pyrimidin-7-one, mp 269–27° C.

Analysis calculated for $C_8H_7N_3OS$: C, 49.73; H, 3.65; N, 21.75. Found: C, 49.67; H, 3.46; N, 21.49.

EXAMPLE 6

7-Chloro-2-methylsulfanyl-pyrido[2,3-d]pyrimidine

A suspension of 1.0 g (5.2 mmol) of 2-methylsulfanyl-8H-pyrido[2,3-d]pyrimidin-7-one (Example 5) in 10 mL of phosphorus oxychloride is heated under reflux for 1 hour. The resulting solution is cooled and concentrated to give a solid, which is triturated with cold water and filtered to give 1.05 g of crude product. Recrystallization from acetonitrile lives 0.76 g (69%) of the product, mp 201–203° C.

MS (APCI) M+1: Calcd 212.0; Found 212.0.

Anal. Calcd for $C_8H_6Cl_1S_1N_3$: C, 45.39; H, 2.86; N, 19.85. Found: C, 45.53; H, 2.90; N, 19.74.

EXAMPLE 7

2-Methylsulfanyl-pyrido[2,3-d]pyrimidin-7-ylamine

A suspension of 2.95 g (13.9 mmol) of 7-chloro-2-methylsulfanyl-pyrido[2,3-d]pyrimidine (Example 6) in 200 mL of isopropanol saturated with ammonia is sealed and heated at 40° C. for 65 hours. The suspension is resaturated with ammonia and heated for another 18 hours at 40° C. The solid is collected by filtration and triturated with water to give 1.98 g (74.2%) of the product, mp>250° C.

MS (APCI) M+1: Calcd 193.1; Found 193.0.

Anal. Calcd for $C_8H_8N_4S_1$: C, 49.98; H, 4.19; N, 29.14. Found: C, 50.14; H, 4.22; N, 29.04.

EXAMPLE 8

2-Methanesulfinyl-pyrido[2,3-d]pyrimidin-7-ylamine

A suspension of 10.63 g (55.3 mmol) of 2-methylsulfanyl-pyrido[2,3-d]pyrimidin-7-ylamine (Example 7) in 300 mL of dichloromethane and 300 mL of methanol is treated with 18.06 g (69.1 mmol) of (±)-trans-2-(phenylsulfonyl)-3-phenyloxaziridine and stirred overnight. The suspension is filtered to remove a small amount of solid, concentrated to approximately 25 mL, and diluted with ethyl acetate. The solid is collected by filtration to give 9.27 g (80.5%) of the product, mp 180° C. (dec).

MS (APCI) M+1: Calcd 209.0; Found 209.1.

EXAMPLE 9

$N^2$-Phenyl-pyrido[2,3-d]pyrimidine-2,7-diamine

A suspension of 0.44 g (2.1 mmol) of 2-methanesulfinyl-pyrido[2,3-d]pyrimidin-7-ylamine (Example 8) and 0.39 mL (4.2 mmol) of aniline in 2 mL of dimethylsulfoxide is heated at 100° C. overnight. The resulting solution is cooled and poured into water. Ethyl acetate is added to the suspension, and the solid is collected by filtration. The solid is purified by flash chromatography, eluting with gradient of 0% to 20% methanol/dichloromethane during 30 minutes to give 0.14 g (29%) of the product, mp 255–260° C.

MS (APCI) M+1: Calcd 238.1; Found 238.1.

Anal. Calcd for $C_{13}H_{11}N_5 \cdot 0.18\ H_2O$: C, 64.92; H, 4.76; N, 29.12. Found: C, 65.26; H, 4.75; N, 28.76.

EXAMPLE 10

1-tert-Butyl-3-(2-phenylamino-pyrido[2,3-d]pyrimidin-7-yl)-urea

To a solution of 0.1022 g (0.431 mmol) of $N^2$-phenyl-pyrido[2,3-d]pyrimidine-2,7-diamine (Example 9) in 2 mL of dimethylformamide, cooled in an ice bath, is added 0.019 g (0.47 mmol) of 60% sodium hydride. The resulting solution cooled in an ice bath, is then treated with 0.054 mL (0.47 mmol) of tert-butyl isocyanate. The solution is stirred cold for 15 minutes, then at room temperature for 1 hour. The solution is poured into ice-water to give a solid which is collected by filtration and washed with hexane to give 0.0849 g (57.8%) of the product (compound 45), mp 227° C. (dec).

MS (APCI) M+1: Calcd 337.2; Found 337.1.

Anal. Calcd for $C_{18}H_{20}N_6O_1 \cdot 0.27\ H_2O$: C, 63.35; H, 6.07; N, 24.63. Found: C, 63.73; H, 5.82; N, 24.20.

EXAMPLE 11

4-(4-Nitrophenyl)-piperazine-1-carboxylic acid tert-butyl ester

A suspension of 7.5 g (36 mmol) of 1-(4-nitrophenyl)-piperazine and 6.94 mL (40 mmol) of ethyl-diisopropyl-amine in 75 mL of dichloromethane is treated with 8.69 g (40 mmol) of di-tert-butyl dicarbonate and stirred at room temperature overnight. The resulting solution is washed with saturated aqueous sodium bicarbonate, then with water, dried (magnesium sulfate), and concentrated. The resulting material is purified by flash chromatography eluting with a gradient of 10% to 30% ethyl acetate/hexane during 10 minutes to give 8.62 g (77.5%) of the product, mp 136–140° C.

MS (APCI) M+1: Calcd 308.2; Found 308.2.

EXAMPLE 12

4-(4-Amino-phenyl)-piperazine-1-carboxylic acid tert-butyl ester

To a suspension of 1.46 g (4.8 mmol) of 4-(4-nitrophenyl)-piperazine-1-carboxylic acid tert-butyl ester (Example 11) and 1 g of Raney Nickel in 50 mL of tetrahydrofuran is added hydrogen to an initial pressure of 54.5 psi. The reaction is shaken for 14 hours and then filtered. The filtrate is concentrated to give 1.29 g (97%) of the product as a solid.

MS (APCI) M+1: Calcd 278.2; Found 278.2.

Anal. Calcd for $C_{15}H_{23}N_3O_2$: C, 64.96; H, 8.36; N, 15.15. Found: C, 65.22; H, 8.58; N, 14.58.

EXAMPLE 13

4-[4-(7-Amino-pyrido[2,3-d]pyrimidin-2-ylamino)-phenyl]-piperazine-1-carboxylic acid tert-butyl ester By substituting 4-(4-amino-phenyl)-piperazine-1-carboxylic acid tert-butyl ester (Example 12) for aniline in Example 9, 0.0744 g (36.0%) of the product is obtained, mp 219–220° C.

MS (APCI) M+1: Calcd 422.2; Found 422.2.

Anal. Calcd for $C_{22}H_{27}N_7O_2 \cdot 0.5\ H_2O$: C, 61.38; H, 6.56; N, 22.77. Found: C, 61.34; H, 6.30; N, 22.47.

EXAMPLE 14

4-{4-[7-(3-tert-Butyl-ureido)-pyrido[2,3-d]pyrimidin-2-ylamino]-phenyl}-piperazine-1-carboxylic acid tert-butyl ester By substituting 4-[4-(7-amino-pyrido[2,3-d]pyrimidin-2-ylamino)-phenyl]-piperazine-1-carboxylic acid tert-butyl ester (Example 13) for $N^2$-phenyl-pyrido[2,3-d]pyrimidine-2,7-diamine in Example 10, 0.3354 g (67.9%) of the product (compound 79) is obtained, mp 225° C. (dec).

MS (APCI) M+1: Calcd 521.3; Found 521.2.

Anal. Calcd for $C_{27}H_{36}N_8O_3$: C, 62.29; H, 6.97; N, 21.52. Found: C, 62.33; H, 6.81; N, 21.43.

EXAMPLE 15

1-tert-Butyl-3-[2-(4-piperazin-1-yl-phenylamino)-pyrido[2,3-d]pyrimidin-7-yl]-urea To a suspension of 0.100 g (0.192 mmol) of 4-{4-[7-(3-tert-butyl-ureido)-pyrido[2,3-d]pyrimidin-2-ylamino]-phenyl}-piperazine-1-carboxylic acid tert-butyl ester (Example 14) in 2 mL of methanol is added 2 mL of 4 M hydrogen chloride/dioxane to give a solution. The suspension is stirred at room temperature overnight, then diluted with diethyl ether. The material is collected by filtration to give 0.0941 g (93.4%) of the product (compound 1), mp 215° C. (dec).

MS (APCI) M+1: Calcd 421.2; Found 421.1.

Anal. Calcd for $C_{22}H_{28}N_8O_1 \cdot 2.10\ HCl \cdot 1.51\ H_2O$: C, 50.40; H, 6.37; N, 21.37; Cl (total), 14.20. Found: C, 50.40; H, 6.18; N, 21.03; Cl (total), 14.33.

EXAMPLE 16

4-{4-[7-3-Cyclohexyl-ureido)-pyrido[2,3-d]pyrimidin-2-ylamino]-phenyl}-piperazine-1-carboxylic acid tert-butyl ester By substituting cyclohexyl isocyanate for tert-butyl isocyanate in Example 14, 0.1463 g (70.4%) of the product (compound 80) is obtained, mp 241° C. (dec).

MS (APCI) M+1: Calcd 547.3; Found 547.4.

Anal. Calcd for $C_{29}H_{38}N_8O_3 \cdot 0.28\ H_2O$: C, 63.13; H, 7.04; N, 20.31. Found: C, 63.14; H, 6.81; N, 20.25.

EXAMPLE 17

1-Cyclohexyl-3-[2-(4-piperazin-1-yl-phenylamino)-pyrido[2,3-d]pyrimidin-7-yl]-urea By substituting 4-{4-[7-(3-cyclohexyl-ureido)-pyrido[2,3-d]pyrimidin-2-ylamino]-phenyl}-piperazine-1-carboxylic acid tert-butyl ester (Example 16) for 4-{4-[7-(3-tert-butyl-ureido)-pyrido[2,3-d]pyrimidin-2-ylamino]-phenyl}-piperazine-1-carboxylic acid tert-butyl ester in Example 15, 0.0871 g (81.4%) of the product (compound 9) is obtained, mp 200° C. (dec).

MS (APCI) M+1: Calcd 447.3; Found 447.3.

Anal. Calcd for $C_{24}H_{30}N_8O_1 \cdot 2.55\ HCl \cdot 2.82\ H_2O$: C, 48.83; H, 6.52; N, 18.98; Cl (total), 15.31. Found: C, 48.83; H, 6.18; N, 18.89; Cl (total), 15.37.

EXAMPLE 18

$N^2$-(4-Fluoro-3-methyl-phenyl)-pyrido[2,3-d]pyrimidine-2,7-diamine

By substituting 4-fluoro-3-methylaniline for aniline in Example 9, 0.2025 g (39.2%) of the product is obtained as a solid.

MS (APCI) M+1: Calcd 270.1; Found 270.0.

EXAMPLE 19

1-tert-Butyl-3-[2-(4-fluoro-3-methyl-phenylamino)-pyrido[2,3-d]pyrimidin-7-yl]-urea By substituting $N^2$-(4-fluoro-3-methyl-phenyl)-pyrido[2,3-d]pyrimidine-2,7-diamine (Example 18) for $N^2$-phenyl-pyrido[2,3-d]pyrimidine-2,7-diamine in Example 10, 0.0656 g (47.9%) of the product (compound 46) is obtained, mp 230° C. (dec).

MS (APCI) M+1: Calcd 369.2; Found 369.1.

Anal. Calcd for $C_{19}H_{21}F_1N_6O_1$: C, 61.94; H, 5.75; N, 22.81. Found: C, 61.82; H, 5.73; N, 22.75.

EXAMPLE 20

1-(4-Chloro-phenyl)-3-[2-(4-fluoro-3-methyl-phenylamino)-pyrido[2,3-d]pyrimidin-7-yl]-urea By substituting 4-chlorophenyl isocyanate for tertiary-butyl isocyanate in Example 19, 0.050 g (37%) of the product (compound 47) is obtained, mp>250° C.

MS (APCI) M+1: Calcd 423.1; Found 423.1.

Anal. Calcd for $C_{21}H_{16}F_1Cl_1N_6O_1 \cdot 0.23\ H_2O$: C, 59.07; H, 3.89; N, 19.68. Found: C, 59.09; H, 3.97; N, 19.65.

EXAMPLE 21

1-{2-[4-(4-Acetyl-piperazin-1-yl)-phenylamino]-pyrido[2,3-d]pyrimidin-7-yl}-3-tert-butyl-urea To a suspension of 0.145 g (0.277 mmol) of 1-tert-butyl-3-[2-(4-piperazin-1-yl-phenylamino)-pyrido[2,3-d]pyrimidin-7-yl]-urea (Example 15) in 5 mL of dichloromethane is added 0.19 mL (1.11 mmol) of ethyl-diisopropyl-amine. The suspension is cooled in an ice bath and treated with 0.024 mL (0.33 mmol) of acetyl chloride. The suspension is stirred at room temperature overnight, then filtered. The solid is washed with dichloromethane. The filtrate and washings are combined, washed with water, dried (magnesium sulfate), and concentrated. The material is purified by flash chromatography eluting with a gradient of 0% to 5% methanol/dichloromethane during 30 minutes to give 0.0674 g (51.8%) of the product (compound 5), mp 206–208° C. (dec).

MS (APCI) M+1: Calcd 463.3; Found 463.3.

Anal. Calcd for $C_{24}H_{30}N_8O_2 \cdot 0.40\ H_2O$: C, 61.36; H, 6.61; N, 3.85. Found: C, 61.38; H, 6.37; N, 23.98.

EXAMPLE 22

4-{4-[7-(3-Isopropyl-ureido)-pyrido[2,3-d]pyrimidin-2-ylamino]-phenyl}-piperazine-1-carboxylic acid tert-butyl ester By substituting isopropyl isocyanate for tert-butyl isocyanate in Example 14, 0.909 g (69.9%) of the product is obtained as a solid.

MS (APCI) M+1: Calcd 507.3; Found 507.4.

EXAMPLE 23

1-Isopropyl-3-[2-(4-piperazin-1-yl-phenylamino)-pyrido[2,3-d]pyrimidin-7-yl]-urea By substituting 4-{4-[7-(3-isopropyl-ureido)-pyrido[2,3-d]pyrimidin-2-ylamino]-phenyl}-piperazine-1-carboxylic acid tert-butyl ester (Example 22) for 4-{4-[7-(3-tert-butyl-ureido)-pyrido[2,3-d]pyrimidin-2-ylamino]-phenyl}-piperazine-1-carboxylic acid tert-butyl ester in Example 15, 0.0287 g (27.9%) of the product (compound 48) is obtained, mp 190° C. (dec).

MS (APCI) M+1: Calcd 407.2; Found 407.1.

Anal. Calcd for $C_{21}H_{26}N_8O_1 \cdot 2.05\ TFA \cdot 0.84\ H_2O$: C, 46.00; H, 4.57; N, 17.10. Found: C, 46.00; H, 4.65; N, 17.09.

EXAMPLE 24

Cis-3,5-dimethyl-1-(4-nitro-phenyl)-piperazine

A suspension of 6.74 g (47.8 mmol) of 4-fluoro-nitrobenzene and 10.91 g (95.5 mmol) of cis-2,6-dimethyl-piperazine is heated at 45° C. for 1 hour. The reaction mixture is cooled and shaken with dichloromethane and water. The organic layer is dried (magnesium sulfate) and concentrated to give 11.62 g (>100%) of the product as a solid.

EXAMPLE 25

Cis-2,6-dimethyl-4-(4-nitro-phenyl)-piperazine-1-carboxylic acid tert-butyl ester By substituting cis-3,5-dimethyl-1-(4-nitro-phenyl)-piperazine (Example 24) for 1-(4-nitrophenyl)-piperazine in Example 11, 14.87 g (92.8%) of the product as a solid is obtained.

EXAMPLE 26

4-(4-Amino-phenyl)-cis-2,6-dimethyl-piperazine-1-carboxylic acid tert-butyl ester By substituting cis-2,6-dimethyl-4-(4-nitro-phenyl)-piperazine-1-carboxylic acid tert-butyl ester (Example 25) for 4-(4-nitro-phenyl)-piperazine-1-carboxylic acid tert-butyl ester in Example 12, 5.03 g (64.7%) of the product as a solid is obtained.

EXAMPLE 27

4-[4-(7-Amino-pyrido[2,3-d]pyrimidin-2-ylamino)-phenyl]-cis-2,6-dimethyl-piperazine-1-carboxylic acid tert-butyl ester By substituting 4-(4-amino-phenyl)-cis-2,6-dimethyl-piperazine-1-carboxylic acid tert-butyl ester (Example 26) for aniline in Example 9, 0.6463 g (59.8%) of the product is obtained, mp 245° C. (dec).

MS (APCI) M+1: Calcd 450.3; Found 450.3.

EXAMPLE 28

4-{4-[7-(3-tert-Butyl-ureido)-pyrido[2,3-d]pyrimidin-2-ylamino]-phenyl}-cis-2,6-dimethyl-piperazine-1-carboxylic acid tert-butyl ester By substituting 4-[4-(7-amino-pyrido[2,3-d]pyrimidin-2-ylamino)-phenyl]-cis-2,6-dimethyl-piperazine-1-carboxylic acid tert-butyl ester (Example 27) for $N^2$-phenyl-pyrido[2,3-d]pyrimidine-2,7-diamine in Example 10, 0.1828 g (74.9%) of the product is obtained as a solid.

MS (APCI) M+1: Calcd 549.3; Found 549.4.

EXAMPLE 29

1-tert-Butyl-3-{2-[4-(cis-3,5-dimethyl-piperazin-1-yl)-phenylamino]-pyrido[2,3-d]pyrimidin-7-yl}-urea By substituting 4-{4-[7-(3-tert-butyl-ureido)-pyrido[2,3-d]pyrimidin-2-ylamino]-phenyl}-cis-2,6-dimethyl-piperazine-1-carboxylic acid tert-butyl ester (Example 28) for 4-{4-[7-(3-tert-butyl-ureido)-pyrido[2,3-d]pyrimidin-2-ylamino]-phenyl}-piperazine-1-carboxylic acid tert-butyl ester in Example 15 is obtained 0.0910 g (92.9%) of the product (compound 49), mp 245° C. (dec).

MS (APCI) M+1: Calcd 449.3; Found 449.2.

EXAMPLE 30

4-{4-[7-(3-Cyclohexyl-ureido)-pyrido[2,3-d]pyrimidin-2-ylamino]-phenyl}-cis-2,6-dimethyl-piperazine-1-carboxylic acid tert-butyl ester By substituting cyclohexyl isocyanate for tert-butyl isocyanate in Example 28, 0.1156 g (60.8%) of the product is obtained as a solid.

MS (APCI) M+1: Calcd 575.3; Found 575.3.

EXAMPLE 31

1-Cyclohexyl-3-{2-[4-(cis-3,5-dimethyl-piperazin-1-yl)-phenylamino]-pyrido[2,3-d]pyrimidin-7-yl}-urea By substituting 4-{4-[7-(3-cyclohexyl-ureido)-pyrido[2,3-d]pyrimidin-2-ylamino]-phenyl}-cis-2,6-dimethyl-piperazine-1-carboxylic acid tert-butyl ester (Example 30) for 4-{4-[7-(3-tert-butyl-ureido)-pyrido[2,3-d]pyrimidin-2-ylamino]-phenyl}-piperazine-1-carboxylic acid tert-butyl ester in Example 15, 0.1022 g of the product is obtained (compound 50), mp 228° C. (dec).

MS (APCI) M+1: Calcd 475.2; Found 475.2.

EXAMPLE 32

4-{4-[7-(3-Cyclopentyl-ureido)-pyrido[2,3-d]pyrimidin-2-ylamino]-phenyl}-piperazine-1-carboxylic acid tert-butyl ester To a solution of 0.150 g (0.36 mmol) of 4-[4-(7-amino-pyrido[2,3-d]pyrimidin-2-ylamino)-phenyl]-piperazine-1-carboxylic acid tert-butyl ester (Example 13) in 2 mL of dimethylformamide, cooled in an ice bath, is added 0.022 g (0.54 mmol) of 60% sodium hydride. The cooled solution is stirred for 15 minutes, then treated with 0.088 g (0.54 mmol) of carbonyldiimidazole. The cooled solution is stirred for another 30 minutes, then treated with 0.071 mL (0.72 mmol) of cyclopentylamine. The resulting solution is stirred at room temperature for 1 hour, then added to cold water. The solid is collected by filtration to give a first crop of material. The aqueous filtrate is then extracted with dichloromethane, and the extracts are dried (magnesium sulfate) and concentrated to give a second crop of material. The 2 crops are combined and purified by flash chromatography, eluting with a gradient of 0% to 5% methanol/dichloromethane during 30 minutes to give 0.1159 g (60.4%) of the product as a solid.

MS (APCI) M+1: Calcd 533.3; Found 533.4.

EXAMPLE 33

1-Cyclopentyl-3-[2-(4-piperazin-1-yl-phenylamino)-pyrido[2,3-d]pyrimidin-7-yl]-urea By substituting 4-{4-[7-(3-cyclopentyl-ureido)-pyrido[2,3-d]pyrimidin-2-ylamino]-phenyl}-piperazine-1-carboxylic acid tert-butyl ester (Example 32) for 4-{4-[7-(3-tert-butyl-ureido)-pyrido[2,3-d]pyrimidin-2-ylamino]-phenyl}-piperazine-1-carboxylic acid tert-butyl ester in Example 15, 0.0937 g (80.8%) of the product (compound 51) is obtained, mp 210–213° C. (dec).

MS (APCI) M+1: Calcd 433.2; Found 433.2.

Anal. Calc for $C_{23}H_{28}N_8O_1$.2.49 HCl.1.65 $H_2O$.0.1 dioxane: C, 50.02; H, 6.21; N, 19.94; Cl (total), 15.71. Found: C, 49.89; H, 5.81; N, 19.74; Cl (total), 14.74.

EXAMPLE 34

1-(4-Amino-2-methylsulfanyl-pyrimidin-5-yl)-ethanol

To a suspension of 5.0 g (29 mmol) 4-amino-2-methylsulfanyl-pyrimidine-5-carboxaldehyde (Example 3) in 150 mL of tetrahydrofuran, cooled by an ice bath, is added during 20 minutes. 23.2 mL of a 3.0 M methylmagnesium bromide solution in diethyl ether (69.4 mmol). After 1 hour at 0° C. another 23.2 mL of the 3.0 M methylmagnesium bromide solution is added, and the suspension is allowed to come to room temperature and stirred overnight. The reaction is quenched with 100 mL of saturated aqueous ammonium chloride, and partitioned between water and ethyl acetate. The organic layer is dried (magnesium sulfate) and concentrated to give 5.24 g (96%) of the product, mp 140–142° C.

MS (APCI) M+1: Calcd 186.1; Found 185.9.

EXAMPLE 35

1-(4-Amino-2-methylsulfanyl-pyrimidin-5-yl)-ethanone

By substituting 1-(4-amino-2-methylsulfanyl-pyrimidin-5-yl)-ethanol (Example 34) for (4-amino-2-methylsulfanyl-pyrimidin-5-yl)-methanol in Example 3 and conducting the reaction at 80° C. in toluene, 3.74 g (72%) of the product as a solid is obtained.

MS (APCI) M+1: Calcd 184.0; Found 183.9.

EXAMPLE 36

1-(4-Amino-2-methanesulfinyl-pyrimidin-5-yl)-ethanone

By substituting 1-(4-amino-2-methylsulfanyl-pyrimidin-5-yl)-ethanone (Example 35) for 2-methylsulfanyl-pyrido[2,3-d]pyrimidin-7-ylamine in Example 8, 9.57 g (88%) of the product as a solid is obtained.

MS (APCI) M+1: Calcd 200; Found 200.

EXAMPLE 37

4-[4-(5-Acetyl-4-amino-pyrimidin-2-ylamino)-phenyl]-piperazine-1-carboxylic acid tert-butyl ester By substituting 1-(4-amino-2-methanesulfinyl-pyrimidin-5-yl)-ethanone (Example 36) for 2-methanesulfinyl-pyrido[2,3-d]pyrimidin-7-ylamine in Example 13, 4.04 g (65%) of the product as a solid is obtained.

MS (APCI) M+1: Calcd 413; Found 413.

EXAMPLE 38

4-[4-(7-Amino-5-methyl-pyrido[2,3-d]pyrimidin-2-ylamino)-phenyl]-piperazine-1-carboxylic acid tert-butyl ester To a suspension of 0.58 g (14.6 mmol) of 60% sodium hydride in 10 mL of tetrahydrofuran, at 0° C. is added dropwise 2.58 g (14.56 mmol) of diethyl (cyanomethyl) phosphonate. The reaction mixture is stirred at 0° C. for 5 minutes, then at room temperature for 20 minutes. The mixture is then cooled to 0° C. and treated with 2 g (4.85 mmol) of 4-[4-(5-acetyl-4-amino-pyrimidin-2-ylamino)-phenyl]-piperazine-1-carboxylic acid tert-butyl ester (Example 37). The mixture is stirred at room temperature overnight, and then treated with water and saturated aqueous ammonium chloride. The resulting solid is collected by filtration and washed with ether to give 1.069 g (80%) of the product.

MS (APCI) M+1: Calcd 436; Found 436.

EXAMPLE 39

4-{4-[7-(3-Cyclohexyl-ureido)-5-methyl-pyrido[2,3-d]pyrimidin-2-ylamino]-phenyl}-piperazine-1-carboxylic acid tert-butyl ester By substituting 4-[4-(7-amino-5-methyl-pyrido[2,3-d]pyrimidin-2-ylamino)-phenyl]-piperazine-1-carboxylic acid tert-butyl ester (Example 38) for 4-[4-(7-amino-pyrido[2,3-d]pyrimidin-2-ylamino)-phenyl]-piperazine-1-carboxylic acid tert-butyl ester in Example 16, 0.199 g (420%) of the product as a solid is obtained.

MS (APCI) M+1: Calcd 561; Found 561.

EXAMPLE 40

1-Cyclohexyl-3-[5-methyl-2-(4-piperazin-1-yl-phenylamino)-pyrido[2,3-d]pyrimidin-7-yl]-urea By substituting 4-{4-[7-(3-cyclohexyl-ureido)-5-methyl-pyrido[2,3-d]pyrimidine-2-ylamino]-phenyl}-piperazine-1-carboxylic acid tert-butyl ester (Example 39) for 4-{4-[7-(3-tert-butyl-ureido)-pyrido[2,3-d]pyrimidin-2-ylamino]-phenyl}-piperazine-1-carboxylic acid tert-butyl ester in Example 15, the product (compound 12) as a solid is obtained, mp 238° C. (dec).

MS (APCI) M+1: Calcd 461; Found 461.

EXAMPLE 41

5-Methyl-2-methylsulfanyl-pyrido[2,3-d]pyrimidin-7-ylamine

By substituting 1-(4-amino-2-methylsulfanyl-pyrimidin-5-yl)-ethanone (Example 35) for 4-[4-(5-acetyl-4-aminopyrimidin-2-ylamino)-phenyl]-piperazine-1-carboxylic acid tert-butyl ester in Example 38, 0.97 g (85%) of the product as a solid is obtained.

MS (APCI) M+1: Calcd 207; Found 207.

EXAMPLE 42

2-Methanesulfinyl-5-methyl-pyrido[2,3-d]pyrimidin-7-ylamine

By substituting 5-methyl-2-methylsulfanyl-pyrido[2,3-d]pyrimidin-7-ylamine (Example 41) for 2-methylsulfanyl-pyrido[2,3-d]pyrimidine-7-ylamine in Example 8, 0.85 g (83%) of the product as a solid is obtained.

MS (APCI) M+1: Calcd 223; Found 223.

EXAMPLE 43

4-[4-(7-Amino-5-methyl-pyrido[2,3-d]pyrimidin-2-ylamino)-phenyl]-piperazine-1-carboxylic acid tert-butyl ester By substituting 2-methanesulfinyl-5-methyl-pyrido[2,3-d]pyrimidin-7-ylamine (Example 42) for 2-methanesulfinyl-pyrido[2,3-d]pyrimidin-7-ylamine in Example 13, 0.33 g (20%) of the product as a solid is obtained.

MS (APCI) M+1: Calcd 436; Found 436.

EXAMPLE 44

4-{4-[7-(3-tert-Butyl-ureido)-5-methyl-pyrido[2,3-d]pyrimidin-2-ylamino]-phenyl}-piperazine-1-carboxylic acid tert-butyl ester By substituting 4-[4-(7-amino-5-methyl-pyrido[2,3-d]pyrimidin-2-ylamino)-phenyl]-piperazine-1-carboxylic acid tert-butyl ester (Example 43) for $N^2$-phenyl-pyrido[2,3-d]pyrimidine-2,7-diamine in Example 10, 0.17 g (45%) of the product as a solid is obtained.

MS (APCI) M+1: Calcd 535; Found 535.

EXAMPLE 45

1-tert-Butyl-3-[5-methyl-2-(4-piperazin-1-yl-phenylamino)-pyrido[2,3-d]pyrimidin-7-yl]-urea By substituting 4-{4-[7-(3-tert-butyl-ureido)-5-methyl-pyrido[2,3-d]pyrimidin-2-ylamino]-phenyl}-piperazine-1-carboxylic acid tert-butyl ester (Example 44) for 4-{4-[7-(3-tert-butyl-ureido)-pyrido[2,3-d]pyrimidin-2-ylamino]-phenyl}-piperazine-1-carboxylic acid tert-butyl ester in Example 15, 0.070 g (72%) of the product (compound 4) as a solid is obtained, mp 230–232° C. (dec).

MS (APCI) M+1: Calcd 435; Found 435.

EXAMPLE 46

6-Fluoro-2-methylsulfanyl-8H-pyrido[2,3-d]pyrimidin-7-one

A solution of 1.74 g (10.33 mmol) of (diethoxyphosphoryl)-fluoro-acetic acid ethyl ester in 20 mL of tetrahydrofuran is cooled to −78° C. and treated dropwise with 12.9 mL (20.65 mmol) of a 1.6 M solution of n-butyl lithium in hexanes. After stirring for 30 minutes at −78° C. the solution is treated with 1.74 g (10.33 mmol) of 4-amino-2-methylsulfanyl-pyrimidine-5-carboxaldehyde (Example 3), allowed to warm to room temperature, and stirred overnight. The reaction is treated with saturated aqueous ammonium chloride, then water. The solid is collected by filtration and washed with diethyl ether to give 2.01 g (92%) of the product.

MS (APCI) M+1: Calcd 212; Found 212.

EXAMPLE 47

7-Chloro-6-fluoro-2-methylsulfanyl-pyrido[2,3-d]pyrimidine

By substituting 6-fluoro-2-methylsulfanyl-8H-pyrido[2,3-d]pyrimidin-7-one (Example 46) for 2-methylsulfanyl-8H-pyrido[2,3-d]pyrimidin-7-one in Example 6 is obtained 1.86 g (85%) the product as a solid.

MS (APCI) M+1: Calcd 230, 232; Found 230, 232.

EXAMPLE 48

6-Fluoro-2-methylsulfanyl-pyrido[2,3-d]pyrimidine-7-ylamine

By substituting 7-chloro-6-fluoro-2-methylsulfanyl-pyrido[2,3-d]pyrimidine (Example 47) for 7-chloro-2-methylsulfanyl-pyrido[2,3-d]pyrimidine in Example 7 is obtained 0.29 g (90%) of the product as a solid.

MS (APCI) M+1: Calcd 211; Found 211.

EXAMPLE 49

6-Fluoro-2-methanesulfinyl-pyrido[2,3-d]pyrimidin-7-ylamine

By substituting 6-fluoro-2-methylsulfanyl-pyrido[2,3-d]pyrimidin-7-ylamine (Example 48) for 2-methylsulfanyl-pyrido[2,3-d]pyrimidin-7-ylamine in Example 8, 0.26 g (95%) of the product as a solid is obtained.

MS (APCI) M+1: Calcd 227; Found 227.

EXAMPLE 50

4-[4-(7-Amino-6-fluoro-pyrido[2,3-d]pyrimidin-2-ylamino)-phenyl]-cis-2,6-dimethyl-piperazine-1-carboxylic acid tert-butyl ester By substituting 6-fluoro-2-methanesulfinyl-pyrido[2,3-d]pyrimidin-7-ylamine (Example 49) for 2-methanesulfinyl-pyrido[2,3-d]pyrimidin-7-ylamine in Example 27, 0.040 g (63%) of the product as a solid is obtained.

MS (APCI) M+1: Calcd 468; Found 468.

EXAMPLE 51

4-{4-[7-(3-Cyclohexyl-ureido)-6-fluoro-pyrido[2,3-d]pyrimidin-2-ylamino]-phenyl}-cis-2,6-dimethyl-piperazine-1-carboxylic acid tert-butyl ester By substituting 4-[4-(7-amino-6-fluoro-pyrido[2,3-d]pyrimidin-2-ylamino)-phenyl]-cis-2,6-dimethyl-piperazine-1-carboxylic acid tert-butyl ester (Example 50) for 4-[4-(7-amino-pyrido[2,3-d]pyrimidin-2-ylamino)-phenyl]-piperazine-1-carboxylic acid tert-butyl ester in Example 16, 0.10 g (74%) of the product as a solid is obtained.

MS (APCI) M+1: Calcd 593; Found 593.

EXAMPLE 52

1-Cyclohexyl-3-{2-[4-(cis-3,5-dimethyl-piperazin-1-yl)-phenylamino]-6-fluoro-pyrido[2,3-d]pyrimidin-7-yl}-urea By substituting 4-{4-[7-(3-cyclohexyl-ureido)-6-fluoro-pyrido[2,3-d]pyrimidin-2-ylamino]-phenyl}-cis-2,6- dimethyl-piperazine-1-carboxylic acid tert-butyl ester (Example 51) for 4-{4-[7-(3-tert-butyl-ureido)-pyrido[2,3-d]pyrimidin-2-ylamino]-phenyl}-piperazine-1-carboxylic acid tert-butyl ester in Example 15, 0.060 g (75%) of the product (compound 52) as a solid is obtained, mp 227–229° C.

MS (APCI) M+1: Calcd 493; Found 493.

EXAMPLE 53

4-{4-[7-(3-Cyclopentyl-ureido)-5-methyl-pyrido[2,3-d]pyrimidin-2-ylamino]-phenyl}-piperazine-1-carboxylic acid tert-butyl ester By substituting 4-[4-(7-amino-5-methyl-pyrido[2,3-d]pyrimidin-2-ylamino)-phenyl]-piperazine-1-carboxylic acid tert-butyl ester (Example 43) for 4-[4-(7-amino-pyrido[2,3-d]pyrimidin-2-ylamino)-phenyl]-piperazine-1-carboxylic acid tert-butyl ester in Example 32, 0.18 g (55%) of the product as a solid is obtained.

MS (APCI) M+1: Calcd 547; Found 547.

EXAMPLE 54

1-Cyclopentyl-3-[5-methyl-2-(4-piperazin-1-yl-phenylamino)-pyrido[2,3-d]pyrimidin-7-yl]-urea By substituting 4-{4-[7-(3-cyclopentyl-ureido)-5-methyl-pyrido[2,3-d]pyrimidin-2-ylamino]-phenyl}-piperazine-1-carboxylic acid tert-butyl ester (Example 53) for 4-{4-[7-(3-tert-butyl-ureido)-pyrido[2,3-d]pyrimidin-2-ylamino]-phenyl}-piperazine-1-carboxylic acid tert-butyl ester in Example 15, 0.08 g (70%) of the product (compound 53) is obtained, mp 234° C. (dec).

MS (APCI) M+1: Calcd 447; Found 447.

EXAMPLE 55

4(4-{7-[3-(3-Hydroxy-propyl)-ureido]-pyrido[2,3-d]pyrimidin-2-ylamino}-phenyl)-piperazine-1-carboxylic acid tert-butyl ester By substituting 3-amino-1-propanol for cyclopentylamine, and sodium tertiary butoxide for sodium hydride in Example 32, 0.1295 g (52.2%) of the product as a solid is obtained.

MS (APCI) M+1: Calcd 523.3; Found 523.2.

EXAMPLE 56

1-(3-Hydroxy-propyl)-3-[2-(4-piperazin-1-yl-phenylamino)-pyrido[2,3-d]pyrimidin-7-yl]-urea By substituting the product of Example 55 in Example 15, 0.1077 g of the product (compound 81) as a solid is obtained, mp 183° C. (dec).

MS (APCI) M+1: Calcd 423; Found 423.1.

EXAMPLE 57

4-{4-[7-(3-Cyclohexyl-3-methyl-ureido)-pyrido[2,3-d]pyrimidin-2-ylamino]-phenyl}-piperazine-1-carboxylic acid tert-butyl ester By substituting N-methylcyclohexylamine for 3-amino-1-propanol in Example 55, 0.1939 g (72.7%) of the product as a solid is obtained.

MS (APCI) M+1: Calcd 561.3; Found 561.2.

EXAMPLE 58

1-Cyclohexyl-1-methyl-3-[2-(4-piperazin-1-yl-phenylamino)-pyrido[2,3-d]pyrimidin-7-yl]-urea By substituting the product of Example 57 in Example 15, 0.1645 g of the product (compound 65) as a solid is obtained, mp 177° C. (dec).

MS (APCI) M+1: Calcd 461.3; Found 461.2.

EXAMPLE 59

4-(4-{7-[3-((S)-1-Hydroxymethyl-3-methyl-butyl)-ureido]-pyrido[2,3-d]pyrimidin-2-ylamino}-phenyl)-piperazine-1-carboxylic acid tert-butyl ester By substituting (S)-(+)-leucinol for 3-amino-1-propanol in Example 55, 0.1048 g (39.1%) of the product as a solid is obtained.

MS (APCI) M+1: Calcd 565.3; Found 565.3.

EXAMPLE 60

1-((S)-1-Hydroxymethyl-3-methyl-butyl)-3-[2-(4-piperazin-1-yl-phenylamino)-pyrido[2,3-d]pyrimidin-7-yl]-urea By substituting the product of Example 59 in Example 15, 0.0802 g of the product (compound 83) as a solid is obtained, mp 185° C. (dec).

MS (APCI) M+1: Calcd 465.3; Found 465.2.

EXAMPLE 61

4-[4-(7-{[1-(4-Methyl-piperazin-1-yl)-methanoyl]-amino}-pyrido[2,3-d]pyrimidin-2-ylamino)-phenyl]-piperazine-1-carboxylic acid tert-butyl ester By substituting N-methylpiperazine for 3-amino-1-propanol in Example 55, the product as a solid is obtained.

MS (APCI) M+1: Calcd 548.3; Found 548.3.

EXAMPLE 62

4-Methyl-piperazine-1-carboxylic acid [2-(4-piperazin-1-yl-phenylamino)-pyrido[2,3-d]pyrimidin-7-yl]-amide By substituting the product of Example 61 in Example 15, 0.1194 g of the product (compound 84) as a solid is obtained, mp 200° C. (dec).

MS (APCI) M+1: Calcd 448.3; Found 448.2.

EXAMPLE 63

4-(4-{7-[(1-Morpholin-4-yl-methanoyl)-amino]-pyrido[2,3-d]pyrimidin-2-ylamino}-phenyl)-piperazine-1-carboxylic acid tert-butyl ester By substituting morpholine for 3-amino-1-propanol in Example 55, the product as a solid is obtained.

MS (APCI) M+1: Calcd 535.3; Found 535.2.

EXAMPLE 64

Morpholine-4-carboxylic acid [2-(4-piperazin-1-yl-phenylamino)-pyrido[2,3-d]pyrimidin-7-yl]-amide By substituting the product of Example 63 in Example 15, 0.1132 g of the product (compound 85) as a solid is obtained, mp 190° C. (dec).

MS (APCI) M+1: Calcd 435.2; Found 435.2.

EXAMPLE 65

4-{4-[7-(3,3-Dipropyl-ureido)-pyrido[2,3-d]pyrimidin-2-ylamino]-phenyl}-piperazine-1-carboxylic acid tert-butyl ester By substituting dipropylamine for 3-amino-1-propanol in Example 55, the product as a solid is obtained.

MS (APCI) M+1: Calcd 549.3; Found 549.3.

EXAMPLE 66

3-[2-(4-Piperazin-1-yl-phenylamino)-pyrido[2,3-d]
pyrimidin-7-yl]-1,1-dipropyl urea By substituting the product of Example 65 in Example 15, 0.1278 g of the product (compound 86) as a solid is obtained, mp 190° C. (dec).
MS (APCI) M+1: Calcd 449.3; Found 449.2.

EXAMPLE 67

4-[4-(7-{[1-(4-Boc-piperazin-1-yl)-methanoyl]-
amino}-pyrido[2,3-d]pyrimidin-2-ylamino)-phenyl]-
piperazine-1-carboxylic acid tert-butyl ester By substituting Boc-piperazine for 3-amino-1-propanol in Example 55, the product as a solid is obtained.
MS (APCI) M+1: Calcd 634.3; Found 634.3.

EXAMPLE 68

Piperazine-1-carboxylic acid [2-(4-piperazin-1-yl-
phenylamino)-pyrido[2,3-d]pyrimidin-7-yl]-amide By substituting the product of Example 67 in Example 15, 0.0342 g of the product (compound 87) as a solid is obtained, mp 220° C. (dec).
MS (APCI) M+1: Calcd 434.2; Found 434.2.

EXAMPLE 69

4-(4-{7-[3-((R)-1-Hydroxymethyl-2-methyl-propyl)-
ureido]-pyrido[2,3-d]pyrimidin-2-ylamino}-phenyl)-
piperazine-1-carboxylic acid tert-butyl ester By substituting (R)-valinol for 3-amino-1-propanol in Example 55, the product as a solid is obtained.
MS (APCI) M+1: Calcd 551.3; Found 551.3.

EXAMPLE 70

1-((R)-1-Hydroxymethyl-2-methyl-propyl)-3-[2-(4-
piperazin-1-yl-phenylamino)-pyrido[2,3-d]
pyrimidin-7-yl]-urea By substituting the product of Example 69 in Example 15, 0.0639 g of the product (compound 88) as a solid is obtained, mp 200° C. (dec).
MS (APCI) M+1: Calcd 451.3; Found 451.2.

EXAMPLE 71

4-(4-{7-[3,3-Bis-(2-Hydroxy-ethyl)-ureido]-pyrido
[2,3-d]pyrimidin-2-ylamino}-phenyl)-piperazine-1-
carboxylic acid tert-butyl ester By substituting diethanolamine for 3-amino-1-propanol in Example 55, the product as a solid is obtained.
MS (APCI) M+1: Calcd 553.3; Found 553.2.

EXAMPLE 72

1,1-Bis-(2-hydroxy-ethyl)-3-[2-(4-piperazin-1-yl-
phenylamino)-pyrido[2,3-d]pyrimidin-7-yl]-urea By substituting the product of Example 71 in Example 15, 0.0916 g of the product (compound 89) as a solid is obtained, mp 185° C. (dec).
MS (APCI) M+1: Calcd 453.2; Found 453.2.

EXAMPLE 73

6-Bromo-2-methylsulfanyl-8H-pyrido[2,3-d]
pyrimidin-7-one

To 5.00 g (25.9 mmol) of 2-methanesulfanyl-8H-pyrido[2,3-d]pyrimidin-7-one (Example 5) in 130 mL of DMF is added 5.00 g (28.1 mmol) of N-bromosuccinimide. The resulting suspension is stirred at room temperature overnight and concentrated. The solid is triturated with hot water, then washed with isopropanol to give 5.59 g (79.4%) of the product as a solid, mp 266–270° C.

EXAMPLE 74

6-Bromo-7-chloro-2-methylsulfanyl-pyrido[2,3-d]
pyrimidine

By substituting the product of Example 73 in Example 6, 2.73 g (97.2%) of the product is obtained as a solid.
MS (APCI) M+1: Calcd 289.9; Found 289.8.

EXAMPLE 75

6-Bromo-2-methylsulfanyl-pyrido[2,3-d]pyrimidin-
7-ylamine

By substituting the product of Example 74 in Example 7, 2.09 g (82.9%) of the product is obtained as a solid.
MS (APCI) M+1: Calcd 271.0; Found 270.8.

EXAMPLE 76

6-Bromo-2-methanesulfinyl-pyrido[2,3-d]pyrimidin-
7-ylamine

By substituting the product of Example 75 in Example 8, 1.81 g (81.9%) of the product is obtained as a solid, mp 245° C. (dec).
MS (APCI) M+1: Calcd 287.0; Found 286.8.

EXAMPLE 77

4-[4-7-Amino-6-bromo-pyrido[2,3-d]pyrimidin-2-
ylamino)-phenyl]-piperazine-1-carboxylic acid tert-
butyl ester By substituting the product of Example 76 in Example 13, 1.40 g (44.4%) of the product is obtained as a solid.
MS (APCI) M+1: Calcd 500.1; Found 500.0.

EXAMPLE 78

4-{4-[6-Bromo-7-(3-cyclohexyl-ureido)-pyrido[2,3-
d]pyrimidin-2-ylamino]-phenyl}-piperazine-1-
carboxylic acid tert-butyl ester By substituting the product of Example 77 in Example 16, 0.1160 g (46.4%) of the product is obtained as a solid.
MS (APCI) M+1: Calcd 625.2; Found 625.1.

EXAMPLE 79

1-[6-Bromo-2-(4-piperazin-1-yl-phenylamino)-
pyrido[2,3-d]pyrimidin-7-yl]-3-cyclohexyl-urea By substituting the product of Example 78 in Example 15, 0.0886 g (77.0%) of the product (compound 55) is obtained as a solid, mp 195° C. (dec).
MS (APCI) M+1: Calcd 525.2; Found 525.1.

Anal. Calcd for $C_{24}H_{29}Br_1N_8O_1 \cdot 1.64\ H_2O \cdot 1.83\ HCl$: C, 46.37; H, 5.53; N, 18.02; Cl, 10.44. Found: C, 46.53; H, 5.34; N, 17.73; Cl, 10.15.

EXAMPLE 80

4-{4-[6-Bromo-7-(3-tert-butyl-ureido)-pyrido[2,3-d]pyrimidin-2-ylamino]-phenyl}-piperazine-1-carboxylic acid tert-butyl ester By substituting the product of Example 77 in Example 10, 0.2571 g (42.9%) of the product is obtained as a solid.

MS (APCI) M+1: Calcd 599.2; Found 599.2.

EXAMPLE 81

1-[6-Bromo-2-(4-piperazin-1-yl-phenylamino)-pyrido[2,3-d]pyrimidin-7-yl]-3-tert-butyl-urea By substituting the product of Example 80 in Example 15, 0.0481 g of the product (compound 91) is obtained as a solid.

MS (APCI) M+1: Calcd 499.2; Found 499.0.

EXAMPLE 82

4-{4-[6-Bromo-7-(3-methyl-ureido)-pyrido[2,3-d]pyrimidin-2-ylamino]-phenyl}-piperazine-1-carboxylic acid tert-butyl ester By substituting the product of Example 77 and methylamine in Example 32, 0.170 g (29.9%) of the product is obtained as a solid.

MS (APCI) M+1: Calcd 557.2; Found 557.1.

EXAMPLE 83

1-[6-Bromo-2-(4-piperazin-1-yl-phenylamino)-pyrido[2,3-d]pyrimidin-7-yl]-3-methyl-urea By substituting the product of Example 82 in Example 15, 0.0963 g (69%) of the product (compound 93) is obtained as a solid.

MS (APCI) M+1: Calcd 457.1; Found 457.1.

Anal. Calcd for $C_{19}H_{21}Br_1N_8O_1 \cdot 3\ HCl \cdot 3\ H_2O$: C, 36.76; H, 4.87; N, 18.05; Cl, 17.13; $H_2O$, 8.71. Found: C, 36.49; H, 4.35; N, 17.52; Cl, 15.79; $H_2O$, 8.12.

EXAMPLE 84

4-[4-(7-Amino-6-bromo-pyrido[2,3-d]pyrimidin-2-ylamino)-phenyl]-cis-2,6-dimethyl-piperazine-1-carboxylic acid tert-butyl ester By substituting the product of Example 76 in Example 27, 2.10 g (63.1%) of the product is obtained as a solid.

MS (APCI) M+1: Calcd 528.2; Found 528.2.

EXAMPLE 85

4-{4-[6-Bromo-7-(3-tert-butyl-ureido)-pyrido[2,3-d]pyrimidin-2-ylamino]-phenyl}-cis-2,6-dimethyl-piperazine-1-carboxylic acid tert-butyl ester By substituting the product of Example 84 in Example 10, 0.1725 (72.6%) of the product is obtained as a solid.

MS (APCI) M+1: Calcd 627.2; Found 627.2.

EXAMPLE 86

1-{6-Bromo-2-[4-(cis-3,5-dimethyl-piperazin-1-yl)-phenylamino]-pyrido[2,3-d]pyrimidin-7-yl}-3-tert-butyl-urea By substituting the product of Example 85 in Example 15, 0.1593 g (96.0%) of the product (compound 94) is obtained as a solid, mp 20° C. (dec).

MS (APCI) M+1: Calcd 527.2; Found 527.2.

Anal. Calcd for $C_{24}H_{31}Br_1N_8O_1 \cdot 2.55\ HCl \cdot 1.70\ H_2O$: C, 44.28; H, 5.72; N, 17.21; Cl, 13.89. Found: C, 44.28; H, 5.72; N, 17.09; Cl, 12.49.

EXAMPLE 87

4-{4-[6-Bromo-7-(3-cyclohexyl-ureido)-pyrido[2,3-d]pyrimidin-2-ylamino]-phenyl}-cis-2,6-dimethyl-piperazine-1-carboxylic acid tert-butyl ester By substituting the product of Example 84 in Example 16, 0.1750 g (70.7%) of the product is obtained as a solid.

MS (APCI) M+1: Calcd 653.3; Found 653.3.

EXAMPLE 88

1-{6-Bromo-2-[4-(cis-3,5-dimethyl-piperazin-1-yl)-phenylamino]-pyrido[2,3-d]pyrimidin-7-yl}-3-cyclohexyl-urea By substituting the product of Example 87 in Example 15, 0.1614 g (95.4%) of the product (compound 95) is obtained as a solid, mp 198° C. (dec).

MS (APCI) M+1: Calcd 553.2; Found 553.2.

Anal. Calcd for $C_{26}H_{33}N_8O_1Br_1 \cdot 2.76\ HCl \cdot 2.02\ H_2O$: C, 45.22; H, 5.81; N, 16.23; Cl, 14.17. Found: C, 45.23; H, 5.82; N, 16.08; Cl, 13.53.

EXAMPLE 89

$N^2$-(4-Fluoro-phenyl)-pyrido[2,3-d]pyrimidine-2,7-diamine

By substituting 4-fluoroaniline in Example 9, 1.1529 g (45.2%) of the product is obtained as a solid, mp 245–248° C.

MS (APCI) M+1: Calcd 256.1; Found 255.9.

EXAMPLE 90

1-[2-(4-Fluoro-phenylamino)-pyrido[2,3-d]pyrimidin-7-yl]-3-(3-morpholin-4-yl-propyl)-urea By substituting the product of Example 89 and 3-morpholin-4-yl-propylamine in Example 32, 0.1465 g (58.6%) of the product (compound 96) is obtained as a solid, mp 253–256° C.

MS (APCI) M+1: Calcd 426.2; Found 426.1.

Anal. Calcd for $C_{21}H_{24}F_1N_7O_2$: C, 59.28; H, 5.69; N, 23.04. Found: C, 59.18; H, 5.66; N, 23.04.

EXAMPLE 91

1-[2-(4-Fluoro-phenylamino)-pyrido[2,3-d]pyrimidin-7-yl]-3-(2-hydroxy-ethyl)-urea By substituting the product of Example 89 and 2-hydroxy-ethylamine in Example 32, 0.0811 g (40.3%) of the product (compound 97) is obtained as a solid, mp 238–240° C.

MS (APCI) M+1: Calcd 343.1; Found 343.1.

Anal. Calcd for $C_{16}H_{15}F_1N_6O_2$: C, 56.14; H, 4.42; N, 24.55. Found: C, 55.82; H, 4.52; N, 24.15.

EXAMPLE 92

1-(2-Amino-ethyl)-3-[2-(4-fluoro-phenylamino)-pyrido[2,3-d]pyrimidin-7-yl]-urea

By substituting the product of Example 89 and ethylenediamine in Example 32, 0.1000 g (49.3%) of the product (compound 98) is obtained as a solid, mp 217–220° C.

MS (APCI) M+1: Calcd 342.1; Found 342.0.

Anal. Calcd for $C_{16}H_{16}F_1N_7O_1 \cdot 0.2\ H_2O$: C, 55.71; H, 4.79; N, 28.42. Found: C, 55.72; H, 4.57; N, 28.07.

EXAMPLE 93

1-(2-Dimethylamino-ethyl)-3-[2-(4-fluoro-phenylamino)-pyrido[2,3-d]pyrimidin-7-yl]-urea By substituting the product of Example 89 and 2-dimethylamino-ethylamine in Example 32, 0.0778 g (35.8%) of the product (compound 99) is obtained as a solid, mp 251–255° C.

MS (APCI) M+1: Calcd 370.2; Found 370.0.

Anal. Calcd for $C_{18}H_{20}F_1N_7O_1$: C, 58.53; Hz 5.46; N, 26.54. Found: C, 58.39; H, 5.51; N, 26.26.

EXAMPLE 94

3,3-Dimethyl-1-(4-nitro-phenyl)-piperazine

By substituting 2,2-dimethyl-piperazine in Example 24, 29.43 g (88.4%) of the product is obtained as a solid.

MS (APCI) M+1: Calcd 236; Found 236.

EXAMPLE 95

2-2-Dimethyl-4-(4-nitro-phenyl)-piperazine-1-carboxylic acid tert-butyl ester

By substituting the product of Example 94 in Example 11, 38 g (93%) of the product is obtained as a solid.

MS (APCI) M+1: Calcd 336; Found 336.

EXAMPLE 96

4-(4-Amino-phenyl)-2,2-dimethyl-piperazine-1-carboxylic acid tert-butyl ester

By substituting the product of Example 95 in Example 12, 27 g (78%) of the product is obtained as a solid.

MS (APCI) M+1: Calcd 306; Found 306.

EXAMPLE 97

4-[4-(7-Amino-6-fluoro-pyrido[2,3-d]pyrimidin-2-ylamino)-phenyl]-2,2-dimethyl-piperazine-1-carboxylic acid tert-butyl ester By substituting the product of Example 96 in Example 50, 0.4346 g (59.0%) of the product is obtained as a solid.

MS (APCI) M+1: Calcd 468.2; Found 468.3.

EXAMPLE 98

4-{4-[7-(3-Cyclohexyl-ureido)-6-fluoro-pyrido[2,3-d]pyrimidin-2-ylamino]-phenyl}-2,2-dimethyl-piperazine-1-carboxylic acid tert-butyl ester By substituting the product of Example 97 in Example 16, 0.170 g (31.2%) of the product is obtained as a solid.

MS (APCI) M+1: Calcd 593.2; Found 593.4.

EXAMPLE 99

1-Cyclohexyl-3-{2-[4-(3,3-dimethyl-piperazin-1-yl)-phenylamino]-6-fluoro-pyrido[2,3-d]pyrimidin-7-yl}-urea By substituting the product of Example 98 in Example 15, 0.040 g of the product (compound 100) is obtained as a solid.

MS (APCI) M+1: Calcd 493.3; Found 493.2.

EXAMPLE 100

4-[4-(7-Amino-6-fluoro-pyrido[2,3-d]pyrimidin-2-ylamino)-phenyl]-piperazine-1-carboxylic acid tert-butyl ester By substituting the product of Example 12 in Example 50, 0.2017 g (29.7%) of the product is obtained as a solid.

MS (APCI) M+1: Calcd 440.2; Found 440.2.

EXAMPLE 101

4-{4-[7-(3-Cyclohexyl-ureido)-6-fluoro-pyrido[2,3-d]pyrimidin-2-ylamino]-phenyl}-piperazine-1-carboxylic acid tert-butyl ester By substituting the product of Example 100 in Example 16, 0.2036 g (78.6%) of the product is obtained as a solid.

MS (APCI) M+1: Calcd 565.3; Found 565.3.

EXAMPLE 102

1-Cyclohexyl-3-[6-fluoro-2-(4-piperazin-1-yl-phenylamino)-pyrido[2,3-d]pyrimidin-7-yl]-urea By substituting the product of Example 101 in Example 15, 0.1084 g (96.0%) of the product (compound 11) is obtained as a solid.

MS (APCI) M+1: Calcd 465.2; Found 465.2.

Anal. Calcd for $C_{24}H_{29}F_1N_8O_1 \cdot 2.75\ HCl \cdot 3.5\ H_2O$: C, 45.91; H, 5.10; N, 17.85; Cl, 15.53; $H_2O$, 10.04. Found: C, 46.20; H, 5.86; N, 17.45; Cl, 15.22; $H_2O$, 8.97.

EXAMPLE 103

4-{4-[7-(3-tert-Butyl-ureido)-6-fluoro-pyrido[2,3-d]pyrimidin-2-ylamino]-phenyl}-cis-2,6-dimethyl piperazine-1-carboxylic acid tert-butyl ester By substituting the product of Example 50 in Example 10, 0.070 g (17.9%) of the product is obtained as a solid.

MS (APCI) M+1: Calcd 567.3; Found 567.3.

EXAMPLE 104

1-tert-Butyl-3-{2-[4(cis-3,5-dimethyl-piperazin-1-yl)-phenylamino]-6-fluoro-pyrido[2,3-d]pyrimidin-7-yl}-urea By substituting the product of Example 103 in Example 15, 0.0585 g of the product (compound 102) is obtained as a solid.

MS (APCI) M+1: Calcd 467.3; Found 467.3.

EXAMPLE 105

1-[4-(4-Nitro-phenyl)-piperazinyl]-ethanone

To a solution of 5.0 g (24.1 mmol) of 1-(4-nitro-phenyl)-piperazine in 100 mL of dichloromethane was added 5.04 mL (28.9 mmol) of diisopropyl-ethylamine. The solution is cooled in an ice-bath, treated with 1.89 mL (26.5 mmol) of acetyl chloride, and stirred at room temperature overnight. The reaction is washed successively with water, 0.5 M HCl, saturated sodium hydrogen carbonate, and brine, and dried over magnesium sulfate, and concentrated to give 5.91 g (98.5%) of the product as a solid.

MS (APCI) M+1: Calcd 250.1; Found 250.0.

EXAMPLE 106

1-[4-(4-Amino-phenyl)-piperazin-1-yl]-ethanone

By substituting the product of Example 105 in Example 12, 4.35 g (84.1%) of the product is obtained as a solid.
MS (APCI) M+1: Calcd 220.1; Found 220.1.

EXAMPLE 107

1-{4-[4-(7-Amino-pyrido[2,3-d]pyrimidin-2-ylamino)-phenyl]-piperazin-1-yl}-ethanone By substituting the product of Example 106 in Example 9, 0.1829 g (50.1%) of the product is obtained as a solid.
MS (APCI) M+1: Calcd 364.2; Found 364.2.
Anal. Calcd for $C_{19}H_{21}N_7O_1 \cdot 1.0\ H_2O$: C, 59.46; H, 6.11; N, 25.55. Found: C, 59.51; H, 6.03; N, 25.28.

EXAMPLE 108

1-{2-[4-(4-Acetyl-piperazin-1-yl)-phenylamino]-pyrido[2,3-d]pyrimidin-7-yl}-3-(3-morpholin-4-yl-propyl)-urea By substituting the product of Example 107 and 3-morpholin-4-yl-propylamine in Example 32, 0.0338 g (22.6%) of the product (compound 103) is obtained as a solid, mp 221–225° C. (dec).
MS (APCI) M+1: Calcd 534.3; Found 534.2.
Anal. Calcd for $C_{27}H_{35}N_9O_3 \cdot 0.5\ H_2O$: C, 59.76; H, 6.69; N, 23.25. Found: C, 59.74; H, 6.53; N, 23.35.

EXAMPLE 109

6-Chloro-2-methylsulfanyl-8H-pyrido[2,3-d]pyrimidin-7-one

By substituting N-chlorosuccinimide in Example 74, 0.3700 g (31.4%) of the product is obtained as a solid, mp 264–266° C. (dec).
MS (APCI) M+1: Calcd 228.0; Found 227.9.

EXAMPLE 110

6,7-Dichloro-2-methylsulfanyl-pyrido[2,3-d]pyrimidine

By substituting the product of Example 109 in Example 6, 0.6534 g (86.5%) of the product is obtained as a solid.
MS (APCI) M+1: Calcd 246.0; Found 245.8.

EXAMPLE 111

6-Chloro-2-methylsulfanyl-pyrido[2,3-d]pyrimidin-7-ylamine

By substituting the product of Example 110 in Example 7, 0.38 g (63%) of the product is obtained as a solid.
MS (APCI) M+1: Calcd 227.0; Found 226.9.

EXAMPLE 112

6-Chloro-2-methanesulfinyl-pyrido[2,3-d]pyrimidin-7-ylamine

By substituting the product of Example 111 in Example 8, 0.2328 g (57.1%) of the product is obtained as a solid, mp 260–262° C.
MS (APCI) M+1: Calcd 243.0; Found 242.9.

EXAMPLE 113

4-[4-(7-Amino-6-chloro-pyrido[2,3-d]pyrimidin-2-ylamino)-phenyl]-cis-2,6-dimethyl-piperazine-1-carboxylic acid tert-butyl ester By substituting the product of Example 112 in Example 27, 0.22 g (49%) of the product is obtained as a solid.
MS (APCI) M+1: Calcd 484.2; Found 484.2.

EXAMPLE 114

4-{4-[7-(3-tert-Butyl-ureido)-6-chloro-pyrido[2,3-d]pyrimidin-2-ylamino]-phenyl}-cis-2,6-dimethyl-piperazine-1-carboxylic acid tert-butyl ester By substituting the product of Example 113 in Example 10, 0.0995 g (39.2%) of the product is obtained as a solid.

EXAMPLE 115

1-tert-Butyl-3-{6-chloro-2-[4-(cis-3,5-dimethyl-piperazin-1-yl)-phenylamino]-pyrido[2,3-d]pyrimidin-7-yl}-urea By substituting the product of Example 114 in Example 15, 0.0995 g of the product (compound 104) is obtained as a solid, mp 205° C. (dec).
MS (APCI) M+1: Calcd 483.2; Found 483.2.

EXAMPLE 116

Methyl-(2-methylsulfanyl-pyrido[2,3-d]pyrimidin-7-yl)-amine

By substituting methylamine in Example 7, 1.46 g (30.0%) of the product is obtained as a solid.
MS (APCI) M+1: Calcd 207.1; Found 206.9.

EXAMPLE 117

(2-Methanesulfinyl-pyrido[2,3-d]pyrimidin-7-yl)-methyl-amine

By substituting the product of Example 116 in Example 8, 1.31 g (83.4%) of the product is obtained as a solid, mp 185° C.
MS (APCI) M+1: Calcd 223.1; Found 223.0.

EXAMPLE 118

4-[4-(7-Methylamino-pyrido[2,3-d]pyrimidin-2-ylamino)-phenyl]-piperazine-1-carboxylic acid tert-butyl ester By substituting the product of Example 117 in Example 13, 0.4934 g (62.9%) of the product is obtained as a solid.
MS (APCI) M+1: Calcd 436.2; Found 436.2.

EXAMPLE 119

4-{4-[7-(3-Cyclohexyl-1-methyl-ureido)-pyrido[2,3-d]pyrimidin-2-yl]-phenyl}-piperazine-1-carboxylic acid tert-butyl ester By substituting the product of Example 118 in Example 16, and using acetonitrile as solvent and no base, 0.8535 g (78.8%) of the product is obtained as a solid.
MS (APCI) M+1: Calcd 561.3; Found 561.3.

EXAMPLE 120

3-Cyclohexyl-1-methyl-1-[2-(4-piperazin-1-yl-phenylamino)-pyrido[2,3-d]pyrimidin-7-yl]-urea By substituting the product of Example 119 in Example 15, 0.2548 g (36.0%) of the product (compound 70) is obtained as a solid, mp 169–175° C.
MS (APCI) M+1: Calcd 461.3; Found 461.2.

EXAMPLE 121

3-Cyclohexyl-1-{2-[4-(cis-3,5-dimethyl-piperazin-1-yl)-phenylamino]-pyrido[2,3-d]pyrimidin-7-}-1-methyl-urea Using the general procedure by which Example 120 is synthesized, 0.1366 g (95.6%) of the product (compound 106) is obtained as a solid, mp 170° C. (dec).

MS (APCI) M+1: Calcd 489.3; Found 489.3.

Anal. Calcd for $C_{25}H_{32}N_8O_1 \cdot 0.25$ $H_2O$: C, 64.56; H, 7.04; N, 24.09. Found: C, 64.57; H, 7.01; N, 23.98.

Anal. Calcd for $C_{27}H_{36}N_8O_1 \cdot 3.32$ $H_2O \cdot 2.69$ HCl: C, 50.16; H, 7.07; N, 17.33; Cl, 14.75. Found: C, 50.36; H, 6.98; N, 16.97; Cl, 15.07.

EXAMPLE 122

3-Cyclohexyl-1-ethyl-1-[2-(4-piperazin-1-yl-phenylamino)-pyrido[2,3-d]pyrimidin-7-yl]-urea Using the general procedure by which Example 120 is synthesized, 0.118 g (94%) of the product (compound 107) is obtained as a solid.

MS (APCI) M+1: Calcd 475.3; Found 475.3.

Anal. Calcd for $C_{26}H_{34}N_8O_1 \cdot 3.0$ HCl$\cdot 0.3$ diethylether: C, 53.89; H, 6.65; N, 18.48. Found: C, 53.75; H, 6.96; N, 18.57.

EXAMPLE 123

3-tert-Butyl-1-{2-[4(cis-3,5-dimethyl-piperazin-1-yl)-phenylamino]-pyrido[2,3-d]pyrimidin-7-yl}-1-ethyl-urea Using the general procedure by which Example 15 is synthesized, 0.022 g (56%) of the product (compound 108) is obtained as a solid.

MS (APCI) M+1: Calcd 477.3; Found 477.3.

EXAMPLE 124

1-Methyl-3-[5-methyl-2-(4-piperazin-1-yl-phenylamino)-pyrido[2,3-d]pyrimidin-7-yl]-urea Using the general procedure by which Example 40 is synthesized, the product (compound 64) is obtained as a solid, mp 204–206° C. (dec).

MS (APCI) M+1: Calcd 393; Found 393.

EXAMPLE 125

1-Ethyl-3-[5-methyl-2-(4-piperazin-1-yl-phenylamino)-pyrido[2,3-d]pyrimidin-7-yl]-urea Using the general procedure by which Example 40 is synthesized the product (compound 28) is obtained as a solid, mp 220–222° C.

MS (APCI) M+1: Calcd 407; Found 407.

EXAMPLE 126

1-[5-Methyl-2-(4-piperazin-1-yl-phenylamino)-pyrido[2,3-d]pyrimidin-7-yl]-3-propyl-urea Using the general procedure by which Example 40 is synthesized, the product (compound 111) is obtained as a solid, mp 223–225° C.

MS (APCI) M+1: Calcd 421; Found 421.

EXAMPLE 127

N,N-Dimethyl-N'-[5-methyl-2-[[4-(1-piperazinyl)phenyl]-amino]-pyrido[2,3-d]pyrimidin-7-yl-sulfamide Using the general procedure by which Example 40 is synthesized, but using dimethyl sulfamyl chloride rather than cyclohexylisocyanate, the product (compound 71) is obtained as a solid, mp 228–230° C. (dec).

MS (APCI) M+1: Calcd 443; Found 443.

EXAMPLE 128

7-Amino-2-methylsulfanyl-pyrido[2,3-d]pyrimidine-6-carboxylic acid ethyl ester

To a solution of 4-amino-2-methanesulfanyl-pyrimidine-5-carboxaldehyde (Example 3) in 10 mL of tetrahydrofuran is added 0.126 mL (1.18 mmol) of ethyl cyanoacetate. The solution is cooled to −10° C., and treated with 2.36 mL (2.36 mmol) of titanium tetrachloride. To the solution is slowly added 0.52 mL (4.72 mmol) of N-methyl morpholine. The reaction is warmed to room temperature over 2 hours, and partitioned between ethyl acetate and saturated aqueous ammonium chloride. The organic layer is concentrated to give a solid, which is triturated with ether to give 0.30 g (96%) of the product as a solid.

MS (APCI) M+1: Calcd 265.1; Found 264.9.

EXAMPLE 129

7-Amino-2-chloro-pyrido[2,3-d]pyrimidine-6-carboxylic acid ethyl ester

To a suspension of the product of Example 128 in 50 mL of chloroform is slowly added sulfuryl chloride, followed by 2 drops of ethanol. The reaction is stirred at room temperature for 16 hours, poured into ether, and the solid collected to give 0.50 g (98%) of the product.

MS (APCI) M+1: Calcd 253.1; Found 253.1.

EXAMPLE 130

7-Amino-2-[4-(4-tert-butoxycarbonyl-piperazin-1-yl)-phenylamino]-pyrido[2,3-d]pyrimidine-6-carboxylic acid ethyl ester A solution of the product of Example 12 and the product of Example 129 in dioxane is heated under reflux for 1.5 hours. The reaction is poured into hexane/ethyl acetate (1:1), and the solid is collected. Flash chromatography using dichloromethane as eluant gave 0.08 g (16%) of the product as a solid.

MS (APCI) M+1: Calcd 494.2; Found 494.1.

EXAMPLE 131

2-[4-(4-tert-Butoxycarbonyl-piperazin-1-yl)-phenylamino]-7-(3-tert-butyl-ureido)-pyrido[2,3-d]pyrimidine-6-carboxylic acid ethyl ester By substituting the product of Example 130 in Example 10, 0.05 g (48%) of the product as a solid is obtained.

EXAMPLE 132

7-(3-tert-Butyl-ureido)-2-(4-piperazin-1-yl-phenylamino)-pyrido[2,3-d]pyrimidine-6-carboxylic acid ethyl ester By substituting the product of Example 131 in Example 15, 0.036 g of the product (compound 113) as a solid is obtained, mp>300° C.

EXAMPLE 133

1-[6-Fluoro-5-methyl-2-(4-piperazin-1-yl-phenylamino)-pyrido[2,3-d]pyrimidin-7-yl]-3-isopropyl-urea Using the general procedure by which Example 52 is synthesized, but using 1-(4-amino-2-methylsulfanyl-pyrimidin-5-yl)-ethanone (Example 35), 4-(4-amino-phenyl)-piperazine-1-carboxylic acid tert-butyl ester (Example 12), and isopropyl isocyanate as reagents, the product (compound 114) is obtained as a solid, mp 208° C. (dec).

MS (APCI) M+1: Calcd 439.2; Found 439.3.

EXAMPLE 134

1-Cyclohexyl-3-{2-[4-(3,3-dimethyl-piperazin-1-yl)-phenylamino]-pyrido[2,3-d]pyrimidin-7-yl}-urea Using the general procedure by which Example 17 is synthesized, but using 4-(4-amino-phenyl)-2,2-dimethyl-piperazine-1-carboxylic acid tert-butyl ester (Example 96), 0.95 g (100%) of the product (compound 115) is obtained as a solid.

MS (APCI) M+1: Calcd 475.6; Found 475.3.

Anal. Calcd for $C_{26}H_{34}N_8O_1.3$ HCl.1 $H_2O$: C, 51.96; H, 6.37; N, 18.64; Cl, 17.69; $H_2O$, 2.99. Found: C, 52.00; H, 6.41; N, 18.53; Cl, 16.51; $H_2O$, 3.06.

EXAMPLE 135

6-Methyl-2-methylsulfanyl-pyrido[2,3-d]pyrimidin-7-ylamine

To a suspension of 2.18 g (54 mmol) of 60% oil dispersed sodium hydride in 300 mL of tetrahydrofuran, cooled to 10° C. is added 10.2 g (53.4 mmol) of (1-cyano-1-methyl-methyl)-phosphonic acid diethyl ester (*Synthesis*, 1975:516). To the cooled suspension is added 4.30 g (25.4 mmol) of 4-amino-2-methanesulfanyl-pyrimidine-5-carboxaldehyde (Example 3), and the reaction is stirred at room temperature for 22 hours. The resulting solution is concentrated and filtered to give a solid, which is washed with tetrahydrofuran, dissolved in 1N citric acid, and re-precipitated by adjusting the pH to 8 with 50% sodium hydroxide. The solid is collected by filtration to give 1.1 g (21%) of the product, mp 268–270° C.

MS (APCI) M+1: Calcd 207.3; Found 207.0.

EXAMPLE 136

1-Cyclohexyl-3-{2-[4-(cis-3,5-dimethyl-piperazin-1-yl)-phenylamino]-6-methyl-pyrido[2,3-d]pyrimidin-7-yl}-urea Using the general procedure by which Example 31 is synthesized, but using the product of Example 135 as the starting material, 0.14 g (420%) of the product (compound 116) is obtained as a solid.

MS (APCI) M+1: Calcd 589.6; Found 589.3.

Anal. Calcd for $C_{27}H_{36}N_8O_1.2.5$ HCl.1.5 $H_2O$: C, 53.80; H, 6.73; N, 18.01; Cl, 14.11; $H_2O$, 4.06. Found: C, 53.44; H, 6.89; N, 18.46; Cl, 14.60; $H_2O$, 4.48.

EXAMPLE 137

1-tert-Butyl-3-{2-[4(cis-3,5-dimethyl-piperazin-1-yl)-phenylamino]-6-methyl-pyrido[2,3-d]pyrimidin-7-yl}-urea Using the general procedure by which Example 29 is synthesized, but using the product of Example 135 as the starting material, 0.26 g (89%) of the product (compound 117) is obtained as a solid.

MS (APCI) M+1: Calcd 463.6; Found 463.3.

Anal. Calcd for $C_{25}H_{36}N_8O_1.2.4$ HCl.1.75 $H_2O$: C, 51.62; H, 6.91; N, 19.26; Cl, 14.63; $H_2O$, 5.42. Found: C, 51.23; H, 6.55; N, 18.92; Cl, 14.73; $H_2O$, 5.10.

EXAMPLE 138

1-tert-Butyl-3-[6-methyl-2-(4-piperazin-1-yl)-phenylamino)-pyrido[2,3-d]pyrimidin-7-yl]-urea Using the general procedure by which Example 15 is synthesized, but using the product of Example 135 as the starting material, 1.02 g (100%) of the product (compound 118) is obtained as a solid.

MS (APCI) M+1: Calcd 435.3; Found 435.3.

Anal. Calcd for $C_{23}H_{30}N_8O_1.5$ HCl.1.75 $H_2O$: C, 42.60; H, 5.98; N, 17.28; Cl, 27.34; $H_2O$, 4.86. Found: C, 42.03; H, 6.04; N, 16.81; Cl, 22.95; $H_2O$, 4.72.

EXAMPLE 139

1-{2-[4-(cis-3,5-Dimethyl-piperazin-1-yl)-phenylamino]-6-methyl-pyrido[2,3-d]pyrimidin-7-yl}-3-isopropyl-urea Using the general procedure by which Example 33 is synthesized, but using the product of Example 135 as the starting material, along with 4-(4-amino-phenyl)-cis-2,6-dimethyl-piperazine-1-carboxylic acid tert-butyl ester and isopropylamine as reagents, 0.130 g (100%) of the product (compound 119) is obtained as a solid.

MS (APCI) M+1: Calcd 449.3; Found 449.3.

Anal. Calcd for $C_{24}H_{32}N_8O_1.3$ HCl.1.75 $H_2O$: C, 48.90; H, 6.58; N, 19.01; Cl, 16.04; $H_2O$, 5.35. Found: C, 49.03; H, 6.63; N, 18.70; Cl, 16.03; $H_2O$, 5.19.

EXAMPLE 140

1-Cyclopropyl-3-{2-[4-(cis-3,5-dimethyl-piperazin-1-yl)-phenylamino]-6-methyl-pyrido[2,3-d]pyrimidin-7-yl}-urea Using the general procedure by which Example 33 is synthesized, but using the product of Example 135 as the starting material, along with 4-(4-amino-phenyl)-cis-2,6-dimethyl-piperazine-1-carboxylic acid tert-butyl ester and cyclopropylamine as reagents, 0.099 g (100%) of the product (compound 120) is obtained as a solid.

MS (APCI) M+1: Calcd 447.3; Found 447.3.

Anal. Calcd for $C_{24}H_{30}N_8O_1$: C, 49.83; H, 6.19; N, 19.37; Cl, 18.39; $H_2O$, 3.89. Found: C, 49.76; H, 6.23; N, 18.92; Cl, 15.66; $H_2O$, 3.06.

EXAMPLE 141

1-tert-Butyl-3-{2-[4-(cis-3,5-dimethyl-piperazin-1-yl)-phenylamino]-6-ethyl-pyrido[2,3-d]pyrimidin-7-yl}-urea Using the general procedure by which Example 137 is synthesized, but using (1-cyano-propyl)-phosphonic acid diethyl ester as starting material, 0.34 g (95%) of the product (compound 121) is obtained as a solid.

MS (APCI) M+1: Calcd 477.3; Found 477.3.

Anal. Calcd for $C_{26}H_{26}N_8O_1.2.5$ HCl.1 $H_2O$: C, 53.26; H, 7.05; N, 19.11; Cl, 15.18; $H_2O$, 3.07. Found: C, 53.63; H, 7.31; N, 18.46; Cl, 15.32; $H_2O$, 3.48.

EXAMPLE 142

The following compounds are prepared essentially according to the procedures described in Examples 1–141 and shown in Schemes 1–4:

(a) 1-tert-Butyl-3-[2-(3-chloro-4-piperazin-1-yl-phenylamino)-pyrido[2,3-d]pyrimidin-7-yl]-urea (compound 2);

(b) 1-tert-Butyl-3-[6-fluoro-2-(4-piperazin-1-yl-phenylamino)-pyrido[2,3-d]pyrimidin-7-yl]-urea (compound 3);

(c) 1-{2-[4-(4-Acetyl-piperazin-1-yl)-3-chloro-phenylamino]-pyrido[2,3-d]pyrimidin-7-yl}-3-tert-butyl-urea (compound 6);

(d) 1-{2-[4-(4-Acetyl-piperazin-1-yl)-phenylamino]-6-fluoro-pyrido[2,3-d]pyrimidin-7-yl}-3-tert-butyl-urea (compound 7);

(e) 1-{2-[4-(4-Acetyl-piperazin-1-yl)-phenylamino]-5-methyl-pyrido[2,3-d]pyrimidin-7-yl}-3-tert-butyl-urea (compound 8);

(f) 1-[2-(3-Chloro-4-piperazin-1-yl-phenylamino)-pyrido[2,3-d]pyrimidin-7-yl]-3-cyclohexyl-urea (compound 10);

(g) 1-{2-[4-(4-Acetyl-piperazin-1-yl)-phenylamino]-pyrido[2,3-d]pyrimidin-7-yl}-3-cyclohexyl-urea (compound 13);

(h) 1-{2-[4-(4-Acetyl-piperazin-1-yl)-3-chloro-phenylamino]-pyrido[2,3-d]pyrimidin-7-yl}-3-cyclohexyl-urea (compound 14);

(i) 1-{2-[4-(4-Acetyl-piperazin-1-yl)-phenylamino]-6-fluoro-pyrido[2,3-d]pyrimidin-7-yl}-3-cyclohexyl-urea (compound 15);

(j) 1-{2-[4-(4-Acetyl-piperazin-1-yl)-phenylamino]-5-methyl-pyrido[2,3-d]pyrimidin-7-yl}-3-cyclohexyl-urea (compound 16);

(k) 1-(2-Hydroxy-ethyl)-3-[2-(4-piperazin-1-yl-phenylamino)-pyrido[2,3-d]pyrimidin-7-yl]-urea (compound 17);

(l) 1-[2-(3-Chloro-4-piperazin-1-yl-phenylamino)-pyrido[2,3-d]pyrimidin-7-yl]-3-(2-hydroxy-ethyl)-urea (compound 18);

(m) 1-[6-Fluoro-2-(4-piperazin-1-yl)-phenylamino)-pyrido[2,3-d]pyrimidin-7-yl]-3-(2-hydroxy-ethyl)-urea (compound 19);

(n) 1-(2-Hydroxy-ethyl)-3-[5-methyl-2-(4-piperazin-1-yl-phenylamino)-pyrido[2,3-d]pyrimidin-7-yl]-urea (compound 20);

(o) 1-{2-[4-(4-Acetyl-piperazin-1-yl)-phenylamino]-pyrido[2,3-d]pyrimidin-7-yl}-3-(2-hydroxy-ethyl)-urea (compound 21);

(p) 1-{2-[4-(4-Acetyl-piperazin-1-yl)-3-chloro-phenylamino]-pyrido[2,3-d]pyrimidin-7-yl}-3-(2-hydroxy-ethyl)-urea (compound 22);

(q) 1-{2-[4-(4-Acetyl-piperazin-1-yl)-phenylamino]-6-fluoro-pyrido[2,3-d]pyrimidin-7-yl}-3-(2-hydroxy-ethyl)-urea (compound 23);

(r) 1-{2-[4-(4-Acetyl-piperazin-1-yl)-phenylamino]-5-methyl-pyrido[2,3-d]pyrimidin-7-yl}-3-(2-hydroxy-ethyl)-urea (compound 24);

(s) 1-Ethyl-3-[2-(4-piperazin-1-yl-phenylamino)-pyrido[2,3-d]pyrimidin-7-yl]-urea (compound 25);

(t) 1-[2-(3-Chloro-4-piperazin-1-yl-phenylamino)-pyrido[2,3-d]pyrimidin-7-yl]-3-ethyl-urea (compound 26);

(u) 1-Ethyl-3-[6-fluoro-2-(4-piperazin-1-yl-phenylamino)-pyrido[2,3-d]pyrimidin-7-yl]-urea (compound 27);

(v) 1-{2-[4-(4-Acetyl-piperazin-1-yl)-phenylamino]-pyrido[2,3-d]pyrimidin-7-yl}-3-ethyl-urea (compound 29);

(w) 1-{2-[4-(4-Acetyl-piperazin-1-yl)-3-chloro-phenylamino]-pyrido[2,3-d]pyrimidin-7-yl}-3-ethyl-urea (compound 30);

(x) 1-{2-[4-(4-Acetyl-piperazin-1-yl)-phenylamino]-6-fluoro-pyrido[2,3-d]pyrimidin-7-yl}-3-ethyl-urea (compound 31);

(y) 1-{2-[4-(4-Acetyl-piperazin-1-yl)-phenylamino]-5-methyl-pyrido[2,3-d]pyrimidin-7-yl}-3-ethyl-urea (compound 32);

(z) 1-tert-Butyl-3-[2-(pyridin-4-ylamino)-pyrido[2,3-d]pyrimidin-7-yl]-urea (compound 33);

(aa) 1-Cyclohexyl-3-[2-(pyridin-4-ylamino)-pyrido[2,3-d]pyrimidin-7-yl]-urea (compound 34);

(bb) 1-Ethyl-3-[2-(pyridin-4-ylamino)-pyrido[2,3-d]pyrimidin-7-yl]-urea (compound 35);

(cc) 1-(Hydroxy-ethyl)-3-[2-(pyridin-4-ylamino)-pyrido[2,3-d]pyrimidin-7-yl]-urea (compound 36);

(dd) 1-tert-Butyl-3-[6-fluoro-2-(pyridin-4-ylamino)-pyrido[2,3-d]pyrimidin-7-yl]-urea (compound 37);

(ee) 1-Cyclohexyl-3-[6-fluoro-2-(pyridin-4-ylamino)-pyrido[2,3-d]pyrimidin-7-yl]-urea (compound 38);

(ff) 1-Ethyl-3-[6-fluoro-2-(pyridin-4-ylamino)-pyrido[2,3-d]pyrimidin-7-yl]-urea (compound 39);

(gg) 1-[6-Fluoro-2-(pyridin-4-ylamino)-pyrido[2,3-d]pyrimidin-7-yl]-3-(2-hydroxy-ethyl)-urea (compound 40);

(hh) 1-tert-Butyl-3-[5-methyl-2-(pyridin-4-ylamino)-pyrido[2,3-d]pyrimidin-7-yl]-urea (compound 41);

(ii) 1-Cyclohexyl-3-[5-methyl-2-(pyridin-4-ylamino)-pyrido[2,3-d]pyrimidin-7-yl]-urea (compound 42);

(jj) 1-Ethyl-3-[5-methyl-2-(pyridin-4-ylamino)-pyrido[2,3-d]pyrimidin-7-yl]-urea (compound 43);

(kk) 1-(2-Hydroxy-ethyl)-3-[5-methyl-2-(pyridin-4-ylamino)-pyrido[2,3-d]pyrimidin-7-yl]-urea (compound 44);

(ll) 1-Cyclohexyl-3-[6-methyl-2-(4-piperazin-1-yl-phenylamino)-pyrido[2,3-d]pyrimidin-7-yl]-urea (compound 54);

(mm) 1-Cyclohexyl-3-[6-cyano-2-(4-piperazin-1-yl-phenylamino)-pyrido[2,3-d]pyrimidin-7-yl]-urea (compound 56);

(nn) 1-Cyclohexyl-3-[6-chloro-2-(4-piperazin-1-yl-phenylamino)-pyrido[2,3-d]pyrimidin-7-yl]-urea (compound 57);

(oo) 1-Cyclohexyl-3-[6-fluoro-5-methyl-2-(4-piperazin-1-yl-phenylamino)-pyrido[2,3-d]pyrimidin-7-yl]-urea (compound 58);

(pp) 1-Cyclohexyl-3-[6-bromo-5-methyl-2-(4-piperazin-1-yl-phenylamino)-pyrido[2,3-d]pyrimidin-7-yl]-urea (compound 59);

(qq) 1-Cyclohexyl-3-[6-chloro-5-methyl-2-(4-piperazin-1-yl-phenylamino)-pyrido[2,3-d]pyrimidin-7-yl]-urea (compound 60);

(rr) 1-Isopropyl-3-[5-methyl-2-(4-piperazin-1-yl-phenylamino)-pyrido[2,3-d]pyrimidin-7-yl]-urea (compound 61);

(ss) 1-[5-Methyl-2-(4-piperazin-1-yl-phenylamino)-pyrido[2,3-d]pyrimidin-7-yl]-urea (compound 63);

(tt) 1-(4-Hydroxy-cyclohexyl)-3-[2-(4-piperazin-1-yl-phenylamino)-pyrido[2,3-d]pyrimidin-7-yl]-urea (compound 66);

(uu) 1-(4-Amino-cyclohexyl)-3-[2-(4-piperazin-1-yl-phenylamino)-pyrido[2,3-d]pyrimidin-7-yl]-urea (compound 67);

(vv) 1-(2-Dimethylamino-ethyl)-3-[-(4-piperazin-1-yl-phenylamino)-pyrido[2,3-d]pyrimidin-7-yl]-urea (compound 68);

(ww) 1-(3-Morpholino-4-yl-propyl)-3-[2-(4-piperazin-1-yl-phenylamino)-pyrido[2,3-d]pyrimidin-7-yl]-urea (compound 69);

(xx) 1-Cyclohexyl-3-[5-methyl-2-(4-piperazin-1-yl-phenylamino)-pyrido[2,3-d]pyrimidin-7-yl]-thiourea (compound 72);

(yy) N-[2-(4-Piperazin-1-yl-phenylamino)-pyrido[2,3-d]pyrimidin-7-yl]-acetamide (compound 73);

(zz) 4-[7-(3-Cyclohexyl-ureido)-pyrido[2,3-d]pyrimidin-2-ylamino]-benzenesulfonamide (compound 74);

(aaa) 1-Cyclohexyl-3-{2-[4-(1-piperazin-1-yl-methanoyl)-phenylamino]-pyrido[2,3-d]pyrimidin-7-yl}-urea (compound 75);

(bbb) 1-Cyclohexyl-3-[2-(4-fluoro-phenylamino)-pyrido[2,3-d]pyrimidin-7-yl]-urea (compound 76);

(ccc) 1-(2-{4-[4-(2-Amino-4-methyl-pentanoyl)-piperazin-1-yl]-phenylamino}-pyrido[2,3-d]pyrimidin-7-yl)-3-cyclohexyl-urea (compound 77); and (ddd) 1-(2-{4-[4-(2-Amino-3-methyl-butanoyl)-piperazin-1-yl]-phenylamino}-pyrido[2,3-d]pyrimidin-7-yl)-3-cyclohexyl-urea (compound 78).

EXAMPLE 143

Biological Assay

As noted above, the compounds of this invention are potent inhibitors of cdks, and accordingly, are useful in treating and preventing atherosclerosis and other cell proliferative disorders like cancer that are mediated by such cdk enzymes. The compounds exhibit excellent inhibitor activity against a number of cdk enzymes, including cdkcdk1/cyclinB, cdk2/cyclinA, cdk2/cyclinE, and cdk4/cyclinD, when evaluated in standard assays routinely utilized by those skilled in the art to measure cdk inhibitors activities. Typical assays are carried out as follows.

Cyclin Dependent Kinase 4 (cdk-4) Assay

Enzyme assays for $IC_{50}$ determinations and kinetic evaluation are performed in 96-well filter plates (Millipore MADVN6550). The total volume is 0.1 mL containing a final concentration of 20 mM TRIS (tris[hydroxymethyl]aminomethane), at pH 7.4, 50 mM NaCl, 1 mM dithiothreitol, 10 mM $MgCl_2$, 25 µM ATP containing 0.25 µCi of [$^{32}$P]ATP, 20 ng of cdk4, 1 µg of retinoblastoma, and appropriate dilutions of a compound of the present invention. All components except the ATP are added to the wells, and the plate is placed on a plate mixer for 2 minutes. The reaction is started by adding [$^{32}$P]ATP, and the plate is incubated at 25° C. for 15 minutes. The reaction is terminated by addition of 0.1 mL of 20% trichloroacetic acid (TCA). The plate is kept at 4° C. for at least 1 hour to allow the substrate to precipitate. The wells are then washed 5 times with 0.2 mL of 10% TCA and $^{32}$P incorporation is determined with a beta plate counter (Wallac Inc., Gaithersburg, Md.).

Cyclin Dependent Kinase 1 and 2 Assays (cdk1/cyclinB, cdk2/cyclinA, cdk2/cyclinE)

Enzyme assays for $IC_{50}$ determinations and kinetic evaluation are performed in a 96-well filter plate (Millipore MADVN6550) in a total volume of 0.1 mL of 20 mM TRIS (tris[hydroxymethyl]aminomethane), at pH 7.4, 50 mM NaCl, 1 mM dithiothreitol, 10 mM $MgCl_2$, 12 mM ATP containing 0.25 µCi of [$^{32}$P]ATP, 20 ng of enzyme (either cdk1/B, cdk2/A, or cdk2/E), 1 µg retinoblastoma and appropriate dilutions of the particular invention compound. All components except the ATP are added to the wells, and the plate is placed on a plate mixer for 2 minutes. The reaction is begun by addition of [$^{32}$P]ATP, and the plate is incubated at 25° C. for 15 minutes. The reaction is terminated by addition of 0.1 mL of 20% TCA. The plate is kept at 4° C. for at least 1 hour to allow the substrate to precipitate. The wells are then washed 5 times with 0.2 mL of 10% TCA and $^{32}$P incorporation determined with a beta plate counter (Wallac Inc., Gaithersburg, Md.).

Cyclin Dependent Kinase 5/p25 Proline-directed Protein Kinase Assay

Source of enzyme: recombinant baculovirus-infected insect cell sf9-expressed recombinant cdk5-p25 complex.

Purpose: To evaluate the ability of test agents to inhibit cdk5/p25 phosphorylation of Histone H1.

Method: Baculovirus-insect cell His-tagged cdk5/Glu-tagged p25 (or GST-p25) enzyme complex is diluted to a concentration of 50 ng/20 µL in Enzyme Dilution Buffer (EDB—50 mM Tris-HCl [pH 8.0], 10 mM NaCl, 10 mM $MgCl_2$, and 1 mM DTT). A 20 µL sample of test agent (diluted in EDB) is then combined with 20 µL of the of the final cdk5/p25 enzyme preparation and allowed to stand for 5 minutes at room temperature. Twenty-five microliters of substrate solution containing 115 µL/mL Histone H1, 30 µM ATP (vanadate-free), and 30 µCi/mL γ-$^{33}$P ATP (Amersham) in EDB is then added to the test agent/enzyme preparation and shaken at 30° C. for 45 minutes. A 50 µL sample of the final preparation is added to 100 mL of 150 mM phosphoric acid on ice for 30 minutes to facilitate precipitation. The precipitate is then filtered through a 96-well phosphocellulose filter plate and subsequently rinsed 3 times with 75 mM phosphoric acid. Each well then receives 20 µL of scintillation cocktail, and the plates are counted for beta emissions using a Trilux Counter ($^{33}$P filter protocol). Test samples are compared to Control (no test agent present: as 0% inhibition) and Baseline level (no enzyme, no test agent: as 100% inhibition) beta emissions to determine the percent inhibition of Histone H1 phosphorylation.

The results of the foregoing assays for representative invention compounds are presented in Table 2 below. The invention compounds exhibit $IC_{50}$ values ranging from 0.027 µM to >5 µM against cdk1/B, from 0.010 µM to >5 µM against cdk2/A, from 0.020 to >5 µM against cdk2/E, and from 0.004 to >5 µM against cdk4/D. The most potent compound overall is compound 9, which exhibits $IC_{50}$ values of 0.027 µM, 0.010 µM, 0.020 µM 0.005 µM, against cdk1/B, cdk2A, cdk2E, and cdk4D, respectively.

TABLE 2

| | Inhibition of Cdks: $IC_{50}$ (µM) | | | |
| --- | --- | --- | --- | --- |
| Compound | Cdk1/B | Cdk2/A | Cdk2/E | Cdk4D |
| 1 | 0.219 | 0.060 | 0.130 | 0.006 |
| 4 | >5 | >5 | >5 | 1.5 |
| 5 | 0.463 | 0.130 | 0.130 | 0.037 |
| 9 | 0.027 | 0.010 | 0.020 | 0.005 |
| 11 | 0.159 | 0.092 | 0.125 | 0.011 |
| 12 | >5 | >5 | >5 | 2.100 |
| 28 | >5 | >5 | >5 | >5 |
| 45 | 0.552 | 0.054 | 0.110 | 0.045 |
| 46 | 0.075 | | 0.300 | >5 |
| 47 | >5 | >5 | >5 | >5 |
| 48 | 0.257 | 0.113 | 0.098 | 0.018 |
| 49 | 0.911 | 0.528 | 0.475 | 0.050 |
| 50 | 0.069 | 0.022 | 0.035 | 0.007 |
| 51 | 0.053 | 0.024 | 0.030 | 0.004 |
| 52 | 0.472 | 0.213 | 0.126 | 0.027 |
| 53 | >5 | >5 | >5 | >5 |

TABLE 2-continued

Inhibition of Cdks: IC$_{50}$ (µM)

| Compound | Cdk1/B | Cdk2/A | Cdk2/E | Cdk4D |
|---|---|---|---|---|
| 55 | >5 | >5 | >5 | 0.300 |
| 64 | >5 | >5 | >5 | >5 |
| 65 | >5 | >5 | >5 | >5 |
| 70 | 1.448 | 0.697 | 0.530 | 0.017 |
| 71 | >5 | >5 | >5 | >5 |
| 79 | >5 | 1.066 | >5 | >5 |
| 80 | 0.461 | 0.092 | 0.230 | 0.460 |
| 81 | 2.610 | 1.560 | 3.250 | 0.500 |
| 83 | 0.399 | 0.305 | 0.315 | 0.055 |
| 84 | >5 | >5 | >5 | >5 |
| 85 | >5 | >5 | >5 | >5 |
| 86 | >5 | >5 | >5 | >5 |
| 87 | >5 | >5 | >5 | >5 |
| 88 | 0.418 | 0.043 | 0.055 | 0.025 |
| 89 | >5 | >5 | >5 | >5 |
| 91 | >5 | >5 | >5 | 0.070 |
| 93 | >5 | >5 | >5 | >5 |
| 94 | | | >5 | 0.101 |
| 95 | | | >5 | 0.310 |
| 96 | 6.365 | 1.108 | 1.550 | >5 |
| 97 | 0.862 | 0.278 | 0.345 | >5 |
| 98 | 0.442 | 0.157 | 0.140 | 1.050 |
| 99 | 1.810 | 1.012 | 0.410 | >5 |
| 100 | 0.265 | 0.153 | 0.415 | 0.035 |
| 102 | 3.130 | 3.590 | 4.500 | 0.165 |
| 103 | >5 | >5 | >5 | >5 |
| 104 | >5 | >5 | >5 | 0.185 |
| 106 | | 0.350 | 0.440 | |
| 107 | 1.728 | 1.950 | 1.650 | 0.019 |
| 108 | 2.425 | 2.035 | 3.050 | 0.067 |
| 111 | >5 | >5 | >5 | >5 |
| 113 | >5 | >5 | >5 | 3.000 |
| 114 | >5 | >5 | >5 | >5 |
| 115 | 0.094 | 0.022 | 0.051 | 0.007 |
| 116 | >5 | >5 | 3.750 | 0.313 |
| 117 | >5 | >5 | 4.000 | 0.076 |
| 118 | >5 | >5 | 3.800 | 0.079 |
| 119 | >5 | >5 | >5 | 1.600 |
| 120 | >5 | >5 | >5 | 1.900 |
| 121 | >5 | >5 | >5 | 0.092 |

The compounds of this invention also are inhibitors of the growth factor receptor tyrosine kinase enzymes, FGFr and PDGFr, and of the nonreceptor tyrosine kinase enzyme, c-Src. Several of the invention compounds have been evaluated via standard assays that measure their ability to inhibit tyrosine kinase enzymes. These assays are carried out as follows:

PDGF and FGF Receptor Tyrosine Kinase Assays

Full-length cDNAs for the mouse PDGF-β and human FGF-1 (flg) receptor tyrosine kinases are obtained from J. Escobedo and prepared as described in *J. Biol. Chem.* 1991; 262:1482–1487. PCR primers are designed to amplify a fragment of DNA that codes for the intracellular tyrosine kinase domain. The fragment is inserted into a baculovirus vector, cotransfected with AcMNPV DNA, and the recombinant virus isolated. SF9 insect cells are infected with the virus to overexpress the protein, and the cell lysate is used for the assay. Assays are performed in 96-well plates (100 µL/incubation/well), and conditions are optimized to measure the incorporation of $^{32}$P from $\gamma^{32}$P-ATP into a glutamate-tyrosine co-polymer substrate. Briefly, to each well is added 82.5 µL of incubation buffer containing 25 mM Hepes (pH 7.0), 150 mM NaCl, 0.1% Triton X-100, 0.2 mM PMSF, 0.2 mM Na$_3$VO$_4$, 10 mM MnCl$_2$, and 750 µg/mL of Poly (4:1) glutamate-tyrosine followed by 2.5 µL of inhibitor and 5 µL of enzyme lysate (7.5 µg/µL FGF-TK or 6.0 µg/µL PDGF-TK) to initiate the reaction. Following a 10-minute incubation at 25° C. 10 mL of $\gamma^{32}$P-ATP (0.4 µCi plus 50 µM ATP) is added to each well, and samples are incubated for an additional 10 minutes at 25° C. The reaction is terminated by the addition of 100 µL of 30% trichloroacetic acid (TCA) containing 20 mM sodium pyrophosphate and precipitation of material onto glass fiber mats (Wallac). Filters are washed 3 times with 15% TCA containing 100 mM sodium pyrophosphate, and the radioactivity retained on the filters counted in a Wallac 1250 Betaplate reader. Nonspecific activity is defined as radioactivity retained on the filters following incubation of samples with buffer alone (no enzyme). Specific enzymatic activity (enzyme plus buffer) is defined as total activity minus nonspecific activity. The % inhibition at 50 µM is determined, and for the more potent compounds the concentration of the compound that inhibited specific activity be 50% (IC$_{50}$) is determined based on the inhibition curve.

C-Src Kinase Assay

C-Src kinase is purified from baculovirus infected insect cell lysates using an antipeptide monoclonal antibody directed against the N-terminal amino acids (amino acids 2–17) of c-Src. The antibody, covalently linked to 0.65 µm latex beads, is added to a suspension of insect cell lysis buffer comprised of 150 mM NaCl, 50 mM Tris pH 7.5, 1 mM DTT, 1% NP-40, 2 mM EGTA, 1 mM sodium vanadate, 1 mM PMSF, 1 µg/mL each of leupeptin, pepstatin, and aprotinin. Insect cell lysate containing c-Src protein is incubated with these beads for 3 to 4 hours at 4° C. with rotation. At the end of the lysate incubation, the beads are rinsed 3 times in lysis buffer, resuspended in lysis buffer containing 10% glycerol, and frozen. These latex beads are thawed, rinsed 3 times in assay buffer (40 mM Tris, pH 7.5, 5 mM MgCl$_2$), and suspended in the same buffer. In a Millipore 96-well plate with a 0.65 µm polyvinylidine membrane bottom are added the reaction components: 10 µL c-Src beads, 10 µL of 2.5 mg/mL poly GluTyr substrate, 5 µM ATP containing 0.2 µCi labeled $^{32}$P-ATP, 5 µL DMSO containing inhibitors or as a solvent control, and buffer to make the final volume 125 µL. The reaction is started at room temperature by addition of the ATP and quenched 10 minutes later by the addition of 125 µL of 30% TCA, 0.1 M sodium pyrophosphate for 5 minutes on ice. The plate is then filtered and the wells washed with two 250-mL aliquots of 15% TCA, 0.1 M pyrophosphate. The filters are then punched, counted in a liquid scintillation counter, and the data examined for inhibitory activity in comparison to a known inhibitor such as erbstatin. The method is also described in *J. Med. Chem.*, 1994; 37:598–609.

The tyrosine kinase inhibitors activity for representative invention compounds evaluated in the foregoing assays is given in Table 3.

TABLE 3

Inhibition of Tyrosine Kinases: % Inhibition at 50 µM (IC$_{50}$ [µM] in parenthesis if determined)

| Compound | PDGFr | FGFr |
|---|---|---|
| 1 | 94.4 (0.593) | 93.7 |
| 9 | | 89.8 |
| 11 | (0.131) | (0.284) |
| 45 | 21.9 | 67.4 |
| 46 | 17.5 | 19.5 |
| 47 | | 10.5 |
| 55 | (0.033) | (0.151) |
| 70 | (0.536) | (1.15) |
| 80 | | 18.6 |
| 117 | (0.081) | (0.061) |

As noted above, the invention also provides pharmaceutical compositions comprising an invention compound admixed with a carrier diluent, or excipient. The following examples illustrate typical compositions provided by this invention.

EXAMPLE 144

A pharmaceutical compositions in the form of hard gelatin capsules for oral administration is prepared using the following ingredients.

|  | Quantity (mg/capsule) |
| --- | --- |
| Active compound | 250 |
| Starch powder | 200 |
| Magnesium stearate | 10 |
| Total | 460 |

The above ingredients are mixed and filled into hard gelatin capsules in 460 mg quantities. A typical active ingredient is 1-isobutyl-3-[2-{(2-chloro-4-piperazin-1-yl)-phenylamino}-pyrido[2,3-d]pyrimidin-7-yl]-urea. The composition is administered from 2 to 4 times a day for treatment of postsurgical restenosis.

EXAMPLE 144a

| Compositions for Oral Suspension | |
| --- | --- |
| Ingredient | Amount |
| 1-Isopropyl-3-[5-methyl-6-bromo-2-(3-ethylpyridin-4-ylamino)-pyrido-[2.3-d]pyrimidin-7-yl]-urea | 500 mg |
| Sorbitol solution (70% NF) | 40 mL |
| Sodium benzoate | 150 mg |
| Saccharin | 10 mg |
| Cherry flavor | 50 mg |
| Distilled water q.s. ad | 100 mL |

The sorbitol solution is added to 40 mL of distilled water, and the pyridopyrimidine is suspended therein. The saccharin, sodium benzoate, and flavoring are added and dissolved. The volume is adjusted to 100 mL with distilled water. Each milliliter of syrup contains 5 mg of active ingredient.

EXAMPLE 144b

| Tablets Each Containing 60 mg of Active Ingredient | | |
| --- | --- | --- |
| Active ingredient | 60 | mg |
| Starch | 45 | mg |
| Microcrystalline cellulose | 35 | mg |
| Polyvinylpyrrolidone (as 10% solution in water) | 4 | mg |
| Sodium carboxymethyl starch | 4.5 | mg |
| Magnesium stearate | 0.5 | mg |
| Talc | 1.0 | mg |
| Total | 150 | mg |

The active ingredient, starch, and cellulose are passed through a No. 45 mesh US sieve and mixed thoroughly. The solution of polyvinylpyrrolidone is mixed with the resultant powders and then passed through a No. 14 mesh US sieve. The granules are dried at 50° C. to 60° C. and passed through a No. 18 mesh US sieve. The sodium carboxymethyl starch, magnesium stearate, and talc, previously passed through a No. 60 mesh US sieve, are then added to the granules which, after mixing, are compressed on a tablet machine to yield tablets each weighing 150 mg.

A typical active ingredient utilized in the above preparation is the compound of Example 40 (Compound 12). This composition is well-suited to treatment of diabetic retinopathy.

EXAMPLE 144c

A parenteral composition suitable for administration by injection is prepared by dissolving 100 mg of compound 77 in 250 mL of 0.9% aqueous sodium chloride solution and adjusting the pH of the solution to about 7.0. This formulation is well-suited for the treatment of breast cancer.

EXAMPLE 144d

Preparation for Suppositories

A mixture of 500 mg of 1-n-butyl-3-[2-(4-piperazin-1-yl-phenylamino)-pyrido[2,3-d]pyrimidin-7-yl]-urea and 1500 mg, of theobroma oil are blended to uniformity at 60° C. The mixture is cooled to 24° C. in tapered molds. Each suppository will weigh about 2 g and can be administered from 1 to 2 times each day for treatment of viral infections such as herpes and HIV.

EXAMPLE 144e

| Topical Preparation | |
| --- | --- |
| Ingredient | Amount (mg) |
| 1-Cyclohexyl-3-{[2-(4-morpholin-1-yl-phenylamino)]-5,6-difluoro-pyrido[2.3-d[pyrimidin-7-yl}-urea | 20 |
| Propylene glycol | 100 |
| White Petrolatum | 500 |
| Cetearyl alcohol | 50 |
| Glyceryl stearate | 100 |
| PEG 100 stearate | 100 |
| Ceteth-20 | 50 |
| Monobasic sodium phosphate | 80 |
| Total | 1000 |

The invention compound is blended to uniformity with the other ingredients to make a thick suspension. The suspension is applied evenly to an adhesive backed polymeric film and cut into a 2-inch square. The patch is applied to the skin of a patient suffering from psoriasis.

EXAMPLE 144f

Slow Release Preparation

Five hundred milligrams of 7-acetamido-6-bromo-2-[4-(2-diethylaminoethoxy)-phenylamino]pyrido[2,3-d]pyrimidine hydrochloride was placed in an osmotic pump tablet and administered orally to a subject for treatment and prevention of restenosis.

The invention and the manner and process of making and using it are now described in such full, clear, concise and exact terms as to enable any person skilled in the art to which it pertains to make and use the same. It is to be understood that the foregoing describes preferred embodiments of the present invention, and that modifications may be made therein without departing from the spirit or scope of the present invention as set forth in the claims. To particularly point out and distinctly claim the subject matter regarded as the invention, the following claims conclude this specification.

What is claimed is:

1. A compound of the Formula I

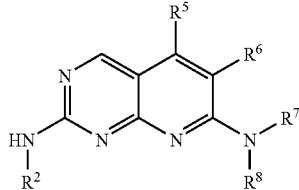

I and pharmaceutically acceptable salts, esters, amides, and prodrugs thereof, wherein:

$R^2$, $R^7$, $R^{13}$, $R^{14}$, and $R^{15}$ are independently hydrogen, or
lower alkyl, lower alkenyl, lower alkynyl, or —$(CH_2)_n$ $R^{12}$ each of which is optionally substituted with up to 5 groups independently selected from halogen, cyano, nitro, —$R^9$, —$NR^9R^{10}$, —$OR^9$, —$(CH_2)_n$ $CO_2R^9$, —$(CH_2)_nSO_2R^{11}$, —$(CH_2)_nR^{11}$, —$COR^9$, —$CONR^9R^{10}$, —$SO_3R^9$, —$SO_2NR^9R^{10}$, —$SO_2R^9$, —$SR^9$, —$PO_3R^9R^{10}$, —$POR^9R^{10}$, —$PO(NR^9R^{10})_2$, —$NR^9COR^{10}$, —$NR^9CO_2R^{10}$, —$NR^9CONR^9R^{10}$, —$NR^9SO_2R^{10}$, or
a heterocycle optionally substituted with up to 3 groups independently selected from —$R^9$, —$NR^9R^{10}$, —$OR^9$, —$NR^9COR^{10}$, —$COR^{10}$, —$(CH_2)_nSO_2R^{11}$, —$(CH_2)_nR^{11}$;

$R^5$ is halogen, cyano, nitro, —$R^9$, —$NR^9R^{10}$, or —$OR^9$;

$R^6$ is halogen, cyano, nitro, —$R^9$, —$NR^9R^{10}$, —$OR^9$, —$CO_2R^9$, —$COR^9$, —$CONR^9R^{10}$, —$NR^9COR^{10}$, —$SO_2NR^9R^{10}$, —$SO_2R^9$, —$SR^9$, —$PO_3R^9R^{10}$, —$POR^9R^{10}$, —$PO(NR^9R^{10})_2$, or
lower alkenyl or lower alkynyl optionally substituted with —$R^9$;

$R^8$ is H, —$CO_2R^{13}$, —$COR^{13}$, —$CONR^{13}R^{14}$, —$CSNR^{13}R^{14}$, —$C(NR^{13})NR^{14}R^{15}$, —$SO_3R^{13}$, —$SO_2R^{13}$, —$SO_2NR^{13}R^{14}$, —$PO_3R^{13}R^{14}$, —$POR^{13}R^{14}$, or —$PO(NR^{13}R^{14})_2$;

$R^9$ and $R^{10}$ are independently hydrogen, or
lower alkyl, optionally substituted with up to 3 groups selected from the group consisting of halogen, amino, mono- or dialkylamino, hydroxy, lower alkoxy, phenyl and substituted phenyl,
or when taken together with the nitrogen to which they are attached, $R^9$ and $R^{10}$ form a ring having from 3–7 members, up to four of which may be selected from the group consisting of

O, S, and $NR^{20}$, where $R^{20}$ is hydrogen, lower alkyl, or —CO lower alkyl;

$R^{11}$ is a heteroaryl or a heterocyclic group;

$R^{12}$ is a cycloalkyl, a heterocyclic, an aryl, or a heteroaryl group; and

Each n is independently 0, 1, 2, or 3.

2. A compound of the Formula II

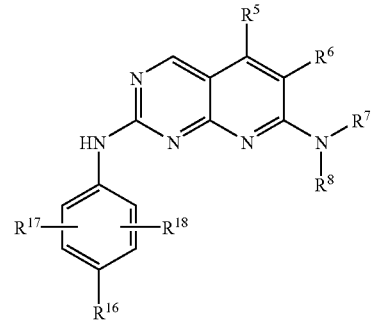

II and pharmaceutically acceptable salts, esters, amides, and prodrugs thereof, wherein:

$R^7$, $R^{13}$, $R^{14}$, and $R^{15}$ are independently hydrogen, or
lower alkyl, lower alkenyl, lower alkynyl, or —$(CH_2)_n$ $R^{12}$ each of which is optionally substituted with up to 5 groups independently selected from halogen, cyano, nitro, —$R^9$, —$NR^9R^{10}$, —$OR^9$, —$(CH_2)_n$ $CO_2R^9$, —$(CH_2)_nSO_2R^{11}$, —$(CH_2)_nR^{11}$, —$COR^9$, —$CONR^9R^{10}$, —$SO_3R^9$, —$SO_2NR^9R^{10}$, —$SO_2R^9$, —$SR^9$, —$PO_3R^9R^{10}$, —$POR^9R^{10}$, —$PO(NR^9R^{10})_2$, —$NR^9COR^{10}$, —$NR^9CO_2R^{10}$, —$NR^9CONR^9R^{10}$, —$NR^9SO_2R^{10}$, or
a heterocycle optionally substituted with up to 3 groups independently selected from —$R^9$, —$NR^9R^{10}$, —$OR^9$, —$(CH_2)_nSO_2R^{11}$, —$(CH_2)_n R^{11}$;

$R^5$ is halogen, cyano, nitro, —$R^9$, —$NR^9R^{10}$, or —$OR^9$;

$R^6$ is halogen, cyano, nitro, —$R^9$, —$NR^9R^{10}$, —$OR^9$, —$CO_2R^9$, —$COR^9$, —$CONR^9R^{10}$, —$NR^9COR^{10}$, or
lower alkenyl or lower alkynyl optionally substituted with —$R^9$;

$R^8$ is H, —$CO_2R^{13}$, —$COR^{13}$, —$CONR^{13}R^{14}$, —$CSNR^{13}R^{14}$, —$C(NR^{13})NR^{14}R^{15}$, —$SO_3R^{13}$, —$SO_2R^{13}$, —$SO_2NR^{13}R^{14}$, —$PO_3R^{13}R^{14}$, —$POR^{13}R^{14}$, or —$PO(NR^{13}R^{14})_2$;

$R^9$ and $R^{10}$ are independently hydrogen, or
lower alkyl, optionally substituted with up to 3 groups selected from the group consisting of halogen, amino, mono- or dialkylamino, hydroxy, lower alkoxy, phenyl and substituted phenyl,
or when taken together with the nitrogen to which they are attached, $R^9$ and $R^{10}$ form a ring having from 3–7 members, up to four of which may be selected from the group consisting of

O, S, and $NR^{20}$, where $R^{20}$ is hydrogen, lower alkyl, or —CO lower alkyl;

$R^{11}$ is a heteroaryl or a heterocyclic group;

$R^{12}$ is a cycloalkyl, a heterocyclic, an aryl, or a heteroaryl group;

each n is independently 0, 1, 2, or 3; and $R^{16}$, $R^{17}$, and $R^{18}$ are independently hydrogen, halogen, amino, mono- or dialkylamino, hydroxy, lower alkyl, lower alkoxy, cyano, nitro, carboxy, carboxyalkyl, aminocarbonyl, mono- or dialkylaminocarbonyl, alkylcarbonyl, —SO$_3$R$^9$, —SO$_2$NR$^9$R$^{10}$, —SO$_2$R$^9$, —SR$^9$, —PO$_3$R$^9$R$^{10}$, —POR$^9$R$^{10}$, —PO(NR$^9$R$^{10}$)$_2$, —NR$^9$COR$^{10}$, —NR$^9$CO$_2$R$^{10}$, —NR$^9$CONR$^9$R$^{10}$, or —NR$^9$SO$_2$R$^{10}$; or R$^{16}$ is a heterocyclic group containing from 3–7 members, up to 2 of which members are heteroatoms selected from oxygen and nitrogen, wherein the heterocyclic group is unsubstituted or substituted with 1, 2, or 3 groups independently selected from the group consisting of halogen, hydroxy, lower alkyl, trifluoromethyl, lower alkoxy, amino, mono- or dialkylamino, aryl, heteroaryl, arylalkyl, heteroarylalkyl, heteroarylsulfonyl, heteroarylsulfonylalkyl, heterocyclylalkyl, heterocyclylsulfonyl, and heterocyclylsulfonylalkyl.

3. A compound of the Formula III

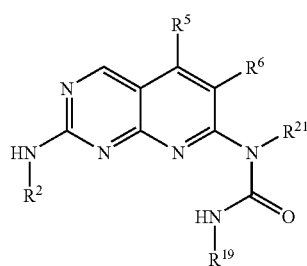

and pharmaceutically acceptable salts, esters, amides, and prodrugs thereof, wherein:

R$^2$ is hydrogen, or
lower alkyl, lower alkenyl, lower alkynyl, or —(CH$_2$)$_n$R$^{12}$, each of which is optionally substituted with up to 5 groups independently selected from halogen, cyano, nitro, —R$^9$, —NR$^9$R$^{10}$, —OR$^9$, —(CH$_2$)$_n$CO$_2$R$^9$, —(CH$_2$)$_n$SO$_2$R$^{11}$, —(CH$_2$)$_n$R$^{11}$, —COR$^9$, —CONR$^9$R$^{10}$, —SO$_3$R$^9$, —SO$_2$NR$^9$R$^{10}$, —SO$_2$R$^9$, —SR$^9$, —PO$_3$R$^9$R$^{10}$, —POR$^9$R$^{10}$, —PO(NR$^9$R$^{10}$)$_2$, —NR$^9$COR$^{10}$, —NR$^9$CO$_2$R$^{10}$, —NR$^9$CONR$^9$R$^{10}$, —NR$^9$SO$_2$R$^{10}$, or
a heterocycle optionally substituted with up to 3 groups independently selected from —R$^9$, —NR$^9$R$^{10}$, —OR$^9$, —(CH$_2$)$_n$SO$_2$R$^{11}$, —(CH$_2$)$_n$R$^{11}$;

R$^5$ is halogen, cyano, nitro, —R$^9$, —NR$^9$R$^{10}$, or —OR$^9$;

R$^6$ is halogen, cyano, nitro, —R$^9$, —NR$^9$R$^{10}$, —OR$^9$, —CO$_2$R$^9$, —COR$^9$, —CONR$^9$R$^{10}$, —NR$^9$COR$^{10}$, —SO$_2$NR$^9$R$^{10}$, —SO$_2$R$^9$, —SO$_3$R$^9$, SR$^9$, —PO$_3$R$^9$R$^{10}$, —POR$^9$R$^{10}$, —PO(NR$^9$R$^{10}$)$_2$, or
lower alkenyl or lower alkynyl optionally substituted with —R$^9$;

R$^9$ and R$^{10}$ are independently hydrogen, or
lower alkyl, optionally substituted with up to 3 groups selected from the group consisting of halogen, amino, mono- or dialkylamino, hydroxy, lower alkoxy, phenyl and substituted phenyl,
or when taken together with the nitrogen to which they are attached, R$^9$ and R$^{10}$ form a ring having from 3–7 members, up to four of which may be selected from the group consisting of

O, S, and NR$^{20}$, where R$^{20}$ is hydrogen, lower alkyl, or —CO lower alkyl;

R$^{11}$ is a heteroaryl or a heterocyclic group;

R$^{12}$ is a cycloalkyl, a heterocyclic, an aryl, or a heteroaryl group;

each n is independently 0, 1, 2, or 3;

R$^{19}$ is hydrogen, or
(i) lower alkyl, lower alkenyl, or lower alkynyl, each of which is optionally substituted with up to 5 groups independently selected from halogen, amino, mono- or dialkylamino, hydroxy, lower alkoxy, cyano, nitro, carboxy, carboxyalkyl, aminocarbonyl, mono- or dialkylaminocarbonyl, lower alkylcarbonyl, —SO$_3$R$^9$, —SO$_2$NR$^9$R$^{10}$, —SO$_2$R$^9$, —SR$^9$, —PO$_3$R$^9$R$^{10}$, —POR$^9$R$^{10}$, —PO(NR$^9$R$^{10}$)$_2$, —NR$^9$COR$^{10}$, —NR$^9$CO$_2$R$^{10}$, —NR$^9$CONR$^9$R$^{10}$, —NR$^9$SO$_2$R$^{10}$, or
(ii) aryl, heteroaryl, arylalkyl, heteroarylalkyl, cycloalkyl or cycloalkyl-alkyl, where each aryl, heteroaryl or cycloalkyl group is optionally substituted with up to 5 groups independently selected from halogen, amino, mono- or dialkylamino, hydroxy, lower alkoxy, cyano, nitro, carboxy, carboxyalkyl, aminocarbonyl, mono- or dialkylaminocarbonyl, alkylcarbonyl, —SO$_3$R$^9$, —SO$_2$R$^9$R$^{10}$, —SO$_2$NR$^9$R$^{10}$, —SO$_2$R$^9$, —SR$^9$, —PO$_3$R$^9$R$^{10}$, —POR$^9$R$^{10}$, —PO(NR$^9$R$^{10}$)$_2$, —NR$^9$COR$^{10}$, —NR$^9$CO$_2$R$^{10}$, —NR$^9$CONR$^9$R$^{10}$, —NR$^9$SO$_2$R$^{10}$, or
(iii) a (CH$_2$)$_n$— heterocyclic group containing from 3–7 members, up to 2 of which members are heteroatoms selected from oxygen and nitrogen, wherein the heterocyclic group is unsubstituted or substituted with 1, 2, or 3 groups independently selected from the group consisting of halogen, hydroxy, lower alkyl, trifluoromethyl, lower alkoxy, amino, mono- or dialkylamino, aryl, heteroaryl, arylalkyl, heteroarylalkyl, heteroarylsulfonyl, heteroarylsulfonylalkyl, heterocyclylalkyl, heterocyclylsulfonyl, and heterocyclylsulfonylalkyl; and R$^{21}$ is hydrogen, lower alkyl, or lower alkyl substituted with phenyl or substituted phenyl.

4. A compound of the Formula IV

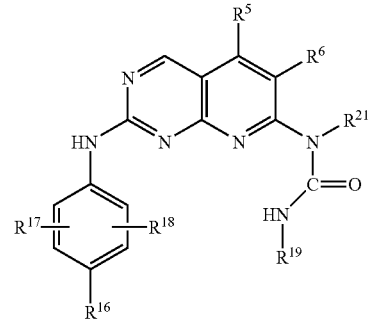

and pharmaceutically acceptable salts, esters, amides, and prodrugs thereof, wherein:

$R^5$ is halogen, cyano, nitro, —$R^9$, —$NR^9R^{10}$, or —$OR^9$;
$R^6$ is halogen, cyano, nitro, —$R^9$, —$NR^9R^{10}$, —$OR^9$, —$CO_2R^9$, —$COR^9$, —$CONR^9R^{10}$, —$NR^9COR^{10}$, —$SO_2NR^9R^{10}$, —$SO_2R^9$, —$SO_3R^9$, —$SR^9$, —$PO_3R^9R^{10}$, $POR^9R^{10}$, —$PO(NR^9R^{10})_2$, or
lower alkenyl or lower alkynyl optionally substituted with —$R^9$;
$R^9$ and $R^{10}$ are independently hydrogen, or lower alkyl optionally substituted with up to 3 groups selected from the group consisting of halogen, amino, mono- or dialkylamino, hydroxy, lower alkoxy, phenyl and substituted phenyl,
or when taken together with the nitrogen to which they are attached, $R^9$ and $R^{10}$ form a ring having from 3–7 members, up to four of which may be selected from

O, S, and $NR^{20}$, where $R^{20}$ is hydrogen, lower alkyl, or —CO lower alkyl;
$R^{11}$ is heteroaryl or a heterocyclic group;
$R^{16}$, $R^{17}$, and $R^{18}$ are independently selected from halogen, cyano, nitro, —$R^9$, —$NR^9R^{10}$, —$OR^9$, —$(CH_2)_n$ $CO_2R^9$, —$(CH_2)_nSO_2R^{11}$, —$(CH_2)_nR^{11}$, —$COR^9$, —$CONR^9R^{10}$, —$SO_3R^9$, —$SO_2NR^9R^{10}$, —$SO_2R^9$, —$SR^9$, —$PO_3R^9R^{10}$, —$POR^9R^{10}$, —PO$(NR^9R^{10})_2$, —$NR^9COR^{10}$, —$NR^9CO_2R^{10}$, —$NR^9CONR^9R^{10}$, —$NR^9SO_2R^{10}$, or
a heterocycle optionally substituted with up to 3 groups independently selected from —$R^9$, —$NR^9R^{10}$, —$OR^9$, —$NR^9COR^{10}$, —$COR^{10}$, —$(CH_2)_nSO_2R^{11}$, —$(CH_2)_nR^{11}$;
$R^{19}$ is hydrogen, or
(i) lower alkyl, lower alkenyl, or lower alkynyl, each of which is optionally substituted with up to 5 groups independently selected from halogen, amino, mono- or dialkylamino, hydroxy, lower alkoxy, cyano, nitro, carboxy, carboxyalkyl, aminocarbonyl, mono- or dialkylaminocarbonyl, lower alkylcarbonyl, —$SO_3R^9$, —$SO_2NR^9R^{10}$, —$SO_2R^9$, —$SR^9$, —$PO_3R^9R^{10}$, —$POR^9R^{10}$, —$PO(NR^9R^{10})_2$, —$NR^9COR^{10}$, —$NR^9CO_2R^{10}$, —$NR^9CONR^9R^{10}$, —$NR^9SO_2R^{10}$, or
(ii) aryl, heteroaryl, arylalkyl, heteroarylalkyl, cycloalkyl or cycloalkyl-alkyl, where each aryl, heteroaryl or cycloalkyl group is optionally substituted with up to 5 groups independently selected from halogen, amino, mono- or dialkylamino, hydroxy, lower alkoxy, cyano, nitro, carboxy, carboxyalkyl, aminocarbonyl, mono- or dialkylaminocarbonyl, alkylcarbonyl, —$SO_3R^9$, —$SO_2R^9R^{10}$, —$SO_2NR^9R^{10}$, —$SO_2R^9$, —$SR^9$, —$PO_3R^9R^{10}$, —$POR^9R^{10}$, —$PO(NR^9R^{10})_2$, —$NR^9COR^{10}$, —$NR^9CO_2R^{10}$, —$NR^9CONR^9R^{10}$, —$NR^9SO_2R^{10}$, or
(iii) a $(CH_2)_n$— heterocyclic group containing from 3–7 members, up to 2 of which members are heteroatoms selected from oxygen and nitrogen, wherein the heterocyclic group is unsubstituted or substituted with 1, 2, or 3 groups independently selected from the group consisting of halogen, hydroxy, lower alkyl, trifluoromethyl, lower alkoxy, amino, mono- or dialkylamino, aryl, heteroaryl, arylalkyl, heteroarylalkyl, heteroarylsulfonyl, heteroarylsulfonylalkyl, heterocyclylalkyl, heterocyclylsulfonyl, and heterocyclylsulfonylalkyl; and
$R^{21}$ is hydrogen, lower alkyl, or lower alkyl substituted with phenyl or substituted phenyl.
5. A compound of the Formula V

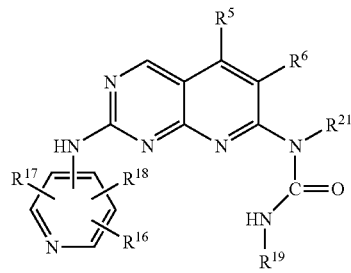

V and the pharmaceutically acceptable salts, esters, amides, and prodrugs thereof;
wherein:
$R^5$ is halogen, cyano, nitro, —$R^9$, —$NR^9R^{10}$, or —$OR^9$;
$R^6$ is halogen, cyano, nitro, —$R^9$, —$NR^9R^{10}$, —$OR^9$, —$CO_2R^9$, —$COR^9$, —$CONR^9R^{10}$, —$NR^9COR^{10}$, —$SO_2NR^9R^{10}$, —$SO_2R^9$, —$SO_3R^9$, $SR^9$, —$PO_3R^9R^{10}$, —$POR^9R^{10}$, —$PO(NR^9R^{10})_2$, or
lower alkenyl or lower alkynyl optionally substituted with —$R^9$;
$R^{16}$, $R^{17}$, and $R^{18}$ are independently selected from hydrogen, halogen, cyano, nitro, —$R^9$, —$NR^9R^{10}$, —$OR^9$, —$(CH_2)_nCO_2R^9$, —$(CH_2)_nSO_2R^{11}$, —$(CH_2)_n$ $R^{11}$, —$COR^9$, —$CONR^9R^{10}$, —$SO_3R^9$, —$SO_2NR^9R^{10}$, —$SO_2R^9$, —$SR^9$, —$PO_3R^9R^{10}$, —$POR^9R^{10}$, —$PO(NR^9R^{10})_2$, —$NR^9COR^{10}$, —$NR^9CO_2R^{10}$, —$NR^9CONR^9R^{10}$, —$NR^9SO_2R^{10}$, or
a heterocycle optionally substituted with up to 3 groups independently selected from —$R^9$, —$NR^9R^{10}$, —$OR^9$, —$NR^9COR^{10}$, —$COR^{10}$, —$(CH_2)_nSO_2R^{11}$, —$(CH_2)_nR^{11}$;
$R^9$ and $R^{10}$ are independently hydrogen, or lower alkyl optionally substituted with up to 3 groups selected from the group consisting of halogen, amino, mono- or dialkylamino, hydroxy, lower alkoxy, phenyl and substituted phenyl,
or when taken together with the nitrogen to which they are attached, $R^9$ and $R^{10}$ form a ring having from 3–7 members, up to four of which may be selected from the group consisting of

O, S, and $NR^{20}$, where $R^{20}$ is hydrogen, lower alkyl, or —CO lower alkyl;
$R^{11}$ is heteroaryl or a heterocyclic group;
$R^{19}$ is hydrogen, or
(i) tower alkyl, lower alkenyl, or tower alkynyl, each of which is optionally substituted with up to 5 groups independently selected from halogen, amino, mono- or dialkylamino, hydroxy, lower alkoxy, cyano, nitro, carboxy, carboxyalkyl, aminocarbonyl, mono- or dialkylaminocarbonyl, lower alkylcarbonyl, —$SO_3R^9$, —$SO_2NR^9R^{10}$, —$SO_2R^9$, —$SR^9$, —PO₃R⁹R¹⁰, —POR⁹R¹⁰, —PO(NR⁹R¹⁰)₂, —NR⁹COR¹⁰, —NR⁹CO₂R¹⁰, —NR⁹CONR⁹R¹⁰, —NR⁹SO₂R¹⁰, or (ii) aryl, heteroaryl, arylalkyl, heteroarylalkyl, cycloalkyl or cycloalkyl-alkyl, where each aryl, heteroaryl or cycloalkyl group is optionally substituted with up to 5 groups independently selected from halogen, amino, mono- or dialkylamino, hydroxy, lower alkoxy, cyano, nitro, carboxy, carboxyalkyl, aminocarbonyl, mono- or dialkylaminocarbonyl, alkylcarbonyl, —SO₃R⁹, —SO₂R⁹R¹⁰, —SO₂NR⁹R¹⁰, —SO₂R⁹, —SR⁹, —PO₃R⁹R¹⁰, —POR⁹R¹⁰, —PO(NR⁹R¹⁰)₂, —NR⁹COR¹⁰, —NR⁹CO₂R¹⁰, —NR⁹CONR⁹R¹⁰, —NR⁹SO₂R¹⁰, or (iii) a (CH₂)ₙ— heterocyclic group containing from 3–7 members, up to 2 of which members are heteroatoms selected from oxygen and nitrogen, wherein the heterocyclic group is unsubstituted or substituted with 1, 2, or 3 groups independently selected from the group consisting of halogen, hydroxy, lower alkyl, trifluoromethyl, lower alkoxy, amino, mono- or dialkylamino, aryl, heteroaryl, arylalkyl, heteroarylalkyl, heteroarylsulfonyl, heterocyclylalkyl, heterocyclylalkyl, heterocyclylsulfonyl, and heterocyclylsulfonylalkyl; and R²¹ is hydrogen, lower alkyl, or lower alkyl substituted with phenyl or substituted phenyl.

6. A compound of Formula VI

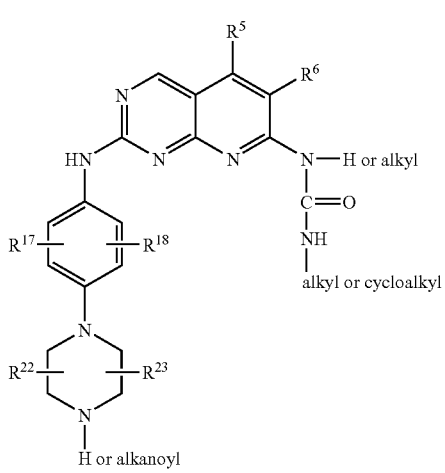

VI and the pharmaceutically acceptable salts, esters, amides, and prodrugs thereof; wherein:

R⁵ is halogen, cyano, nitro, —R⁹, —NR⁹R¹⁰, or —OR⁹;

R⁶ is halogen, cyano, nitro, —R⁹, —NR⁹R¹⁰, —OR⁹, —CO₂R⁹, —COR⁹, —CONR⁹R¹⁰, —NR⁹COR¹⁰, —SO₂NR⁹R¹⁰, —SO₂R⁹, —SO₃R⁹, SR⁹, —PO₃R⁹R¹⁰, —POR⁹R¹⁰, —PO(NR⁹R¹⁰)₂, or lower alkenyl or lower alkynyl optionally substituted with —R⁹;

R¹⁷ and R¹⁸ are independently selected from halogen, cyano, nitro, —R⁹, —NR⁹R¹⁰, —OR⁹, —(CH₂)ₙCO₂R⁹, —(CH₂)ₙSO₂R¹¹, —(CH₂)ₙR¹¹, —COR⁹, —CONR⁹R¹⁰, —SO₃R⁹, —SO₂NR⁹R¹⁰, —SO₂R⁹, —SR⁹, —PO₃R⁹R¹⁰, —POR⁹R¹⁰, —PO(NR⁹R¹⁰)₂, —NR⁹COR¹⁰, —NR⁹CO₂R¹⁰, —NR⁹CONR⁹R¹⁰, —NR⁹SO₂R¹⁰, or a heterocycle optionally substituted with up to 3 groups independently selected from —R⁹, —NR⁹R¹⁰, —OR⁹, —NR⁹COR¹⁰, —COR¹⁰, —(CH₂)ₙSO₂R¹¹, —(CH₂)ₙR¹¹; and R²² and R²³ independently are hydrogen or alkyl.

7. A compound selected from:

1-tert-Butyl-3-[2-(4-piperazin-1-yl-phenylamino)-pyrido[2,3-d]pyrimidin-7-yl]-urea;

1-tert-Butyl-3-[2-(3-chloro-4-piperazin-1-yl-phenylamino)-pyrido[2,3-d]pyrimidin-7-yl]-urea;

1-tert-Butyl-3-[6-fluoro-2-(4-piperazin-1-yl-phenylamino)-pyrido[2,3-d]pyrimidin-7-yl]-urea;

1-tert-Butyl-3-[5-methyl-2-(4-piperazin-1-yl-phenylamino)-pyrido[2,3-d]pyrimidin-7-yl]-urea;

1-{2-[4-(4-Acetyl-piperazin-1-yl)-phenylamino]-pyrido[2,3-d]pyrimidin-7-yl}-3-tert-butyl-urea;

1-{2-[4-(4-Acetyl-piperazin-1-yl)-3-chloro-phenylamino]-pyrido[2,3-d]pyrimidin-7-yl}-3-tert-butyl-urea;

1-{2-[4-(4-Acetyl-piperazin-1-yl)-phenylamino]-6-fluoro-pyrido[2,3-d]pyrimidin-7-yl}-3-tert-butyl-urea;

1-{2-[4-(4-Acetyl-piperazin-1-yl)-phenylamino]-5-methyl-pyrido[2,3-d]pyrimidin-7-yl}-3-tert-butyl-urea;

1-Cyclohexyl-3-[2-(4-piperazin-1-yl-phenylamino)-pyrido[2,3-d]pyrimidin-7-yl]-urea;

1-[2-(3-Chloro-4-piperazin-1-yl-phenylamino)-pyrido[2,3-d]pyrimidin-7-yl]-3-cyclohexyl-urea;

1-Cyclohexyl-3-[6-fluoro-2-(4-piperazin-1-yl-phenylamino)-pyrido[2,3-d]pyrimidin-7-yl]-urea;

1-Cyclohexyl-3-[5-methyl-2-(4-piperazin-1-yl-phenylamino)-pyrido[2,3-d]pyrimidin-7-yl]-urea;

1-{2-[4-(4-Acetyl-piperazin-1-yl)-phenylamino]-pyrido[2,3-d]pyrimidin-7-yl}-3-cyclohexyl-urea;

1-{2-[4-(4-Acetyl-piperazin-1-yl)-3-chloro-phenylamino]-pyrido[2,3-d]pyrimidin-7-yl}-3-cyclohexyl-urea;

1-{2-[4-(4-Acetyl-piperazin-1-yl)-phenylamino]-6-fluoro-pyrido[2,3-d]pyrimidin-7-yl}-3-cyclohexyl-urea;

1-{2-[4-(4-Acetyl-piperazin-1-yl)-phenylamino]-5-methyl-pyrido[2,3-d]pyrimidin-7-yl}-3-cyclohexyl-urea;

1-(2-Hydroxy-ethyl)-3-[2-(4-piperazin-1-yl-phenylamino)-pyrido[2,3-d]pyrimidin-7-yl]-urea;

1-[2-(3-Chloro-4-piperazin-1-yl-phenylamino)-pyrido[2,3-d]pyrimidin-7-yl]-3-(2-hydroxy-ethyl)-urea;

1-[6-Fluoro-2-(4-piperazin-1-yl-phenylamino)-pyrido[2,3-d]pyrimidin-7-yl]-3-(2-hydroxy-ethyl)-urea;

1-(2-Hydroxy-ethyl)-3-[5-methyl-2-(4-piperazin-1-yl-phenylamino)-pyrido[2,3-d]pyrimidin-7-yl]-urea;

1-{2-[4-(4-Acetyl-piperazin-1-yl)-phenylamino]-pyrido[2,3-d]pyrimidin-7-yl}-3-(2-hydroxy-ethyl)-urea;

1-{2-[4-(4-Acetyl-piperazin-1-yl)-3-chloro-phenylamino]-pyrido[2,3-d]pyrimidin-7-yl}-3-(2-hydroxy-ethyl)-urea;

1-{2-[4-(4-Acetyl-piperazin-1-yl)-phenylamino]-6-fluoro-pyrido[2,3-d]pyrimidin-7-yl}-3-(2-hydroxy-ethyl)-urea;

1-{2-[4-(4-Acetyl-piperazin-1-yl)-phenylamino]-5-methyl-pyrido[2,3-d]pyrimidin-7-yl}-3-(2-hydroxy-ethyl)-urea;

1-Ethyl-3-[2-(4-piperazin-1-yl-phenylamino)-pyrido[2,3-d]pyrimidin-7-yl]-urea;

1-[2-(3-Chloro-4-piperazin-1-yl-phenylamino)-pyrido[2,3-d]pyrimidin-7-yl]-3-ethyl-urea;

1-Ethyl-3-[6-fluoro-2-(4-piperazin-1-yl-phenylamino)-pyrido[2,3-d]pyrimidin-7-yl]-urea;

1-Ethyl-3-[5-methyl-2-(4-piperazin-1-yl-phenylamino)-pyrido[2,3-d]pyrimidin-7-yl]-urea;

1-{2-[4-(4-Acetyl-piperazin-1-yl)-phenylamino]-pyrido[2,3-d]pyrimidin-7-yl}-3-ethyl-urea;

1-{2-[4-(4-Acetyl-piperazin-1-yl)-3-chloro-phenylamino]-pyrido[2,3-d]pyrimidin-7-yl}-3-ethyl-urea;

1-{2-[4-(4-Acetyl-piperazin-1-yl)-phenylamino]-6-fluoro-pyrido[2,3-d]pyrimidin-7-yl}-3-ethyl-urea;

1-{2-[4-(4-Acetyl-piperazin-1-yl)-phenylamino]-5-methyl-pyrido[2,3-d]pyrimidin-7-yl}-3-ethyl-urea;

1-tert-Butyl-3-(2-phenylamino-pyrido[2,3-d]pyrimidin-7-yl)-urea;

1-tert-Butyl-3-[2-(4-fluoro-3-methyl-phenylamino)-pyrido[2,3-d]pyrimidin-7-yl]-urea;

1-(4-Chloro-phenyl)-3-[2-(4-fluoro-3-methyl-phenylamino)-pyrido[2,3-d]pyrimidin-7-yl]-urea;

1-Isopropyl-3-[2-(4-piperazin-1-yl-phenylamino)-pyrido[2,3-d]pyrimidin-7-yl]-urea;

1-tert-Butyl-3-{2-[4-(cis-3,5-dimethyl-piperazin-1-yl)-phenylamino]-pyrido[2,3-d]pyrimidin-7-yl}-urea;

1-Cyclohexyl-3-{2-[4-(cis-3,5-dimethyl-piperazin-1-yl)-phenylamino]-pyrido[2,3-d]pyrimidin-7-yl}-urea;

1-Cyclopentyl-3-[2-(4-piperazin-1-yl-phenylamino)-pyrido[2,3-d]pyrimidin-7-yl]-urea;

1-Cyclohexyl-3-{2-[4-(cis-3,5-dimethyl-piperazin-1-yl)-phenylamino]-6-fluoro-pyrido[2,3-d]pyrimidin-7-yl}-urea;

1-Cyclopentyl-3-[5-methyl-2-(4-piperazin-1-yl-phenylamino)-pyrido[2,3-d]pyrimidin-7-yl]-urea;

1-Cyclohexyl-3-[6-methyl-2-(4-piperazin-1-yl-phenylamino)-pyrido[2,3-d]pyrimidin-7-yl]-urea;

1-Cyclohexyl-3-[6-bromo-2-(4-piperazin-1-yl-phenylamino)-pyrido[2,3-d]pyrimidin-7-yl]-urea;

1-Cyclohexyl-3-[6-cyano-2-(4-piperazin-1-yl-phenylamino)-pyrido[2,3-d]pyrimidin-7-yl]-urea;

1-Cyclohexyl-3-[6-chloro-2-(4-piperazin-1-yl-phenylamino)-pyrido[2,3-d]pyrimidin-7-yl]-urea;

1-Cyclohexyl-3-[6-fluoro-5-methyl-2-(4-piperazin-1-yl-phenylamino)-pyrido[2,3-d]pyrimidin-7-yl]-urea;

1-Cyclohexyl-3-[6-bromo-5-methyl-2-(4-piperazin-1-yl-phenylamino)-pyrido[2,3-d]pyrimidin-7-yl]-urea;

1-Cyclohexyl-3-[6-chloro-5-methyl-2-(4-piperazin-1-yl-phenylamino)-pyrido[2,3-d]pyrimidin-7-yl]-urea;

1-Isopropyl-3-[5-methyl-2-(4-piperazin-1-yl-phenylamino)-pyrido[2,3-d]pyrimidin-7-yl]-urea;

1-Ethyl-3-[5-methyl-2-(4-piperazin-1-yl-phenylamino)-pyrido[2,3-d]pyrimidin-7-yl]-urea;

1-[5-Methyl-2-(4-piperazin-1-yl-phenylamino)-pyrido[2,3-d]pyrimidin-7-yl]-urea;

1-Methyl-3-[5-methyl-2-(4-piperazin-1-yl-phenylamino)-pyrido[2,3-d]pyrimidin-7-yl]-urea;

1-Cyclohexyl-1-methyl-3-[2-(4-piperazin-1-yl-phenylamino)-pyrido[2,3-d]pyrimidin-7-yl]-urea;

1-(4-Hydroxy-cyclohexyl)-3-[2-(4-piperazin-1-yl-phenylamino)-pyrido[2,3-d]pyrimidin-7-yl]-urea;

1-(4-Amino-cyclohexyl)-3-[2-(4-piperazin-1-yl-phenylamino)-pyrido[2,3-d]pyrimidin-7-yl]-urea;

1-(2-Dimethylamino-ethyl)-3-[2-(4-piperazin-1-yl-phenylamino)-pyrido[2,3-d]pyrimidin-7-yl]-urea;

1-(3-Morpholino-4-yl-propyl)-3-[2-(4-piperazin-1-yl-phenylamino)-pyrido[2,3-d]pyrimidin-7-yl]-urea;

3-Cyclohexyl-1-methyl-1-[2-(4-piperazin-1-yl-phenylamino)-pyrido[2,3-d]pyrimidin-7-yl]-urea;

N,N-Dimethyl-N□-[5-methyl-2-[[4-(1-piperazinyl)phenyl]-amino]-pyrido[2,3-d]pyrimidin-7-yl]-sulfamide;

1-Cyclohexyl-3-[5-methyl-2-(4-piperazin-1-yl-phenylamino)-pyrido[2,3-d]pyrimidin-7-yl]-thiourea;

N-[2-(4-Piperazin-1-yl-phenylamino)-pyrido[2,3-d]pyrimidin-7-yl]-acetamide;

4-[7-(3-Cyclohexyl-ureido)-pyrido[2,3-d]pyrimidin-2-ylamino]-benzenesulfonamide;

1-Cyclohexyl-3-{2-[4-(1-piperazin-1-yl-methanoyl)-phenylamino]-pyrido[2,3-d]pyrimidin-7-yl}-urea;

1-Cyclohexyl-3-[2-(4-fluoro-phenylamino)-pyrido[2,3-d]pyrimidin-7-yl]-urea;

1-(2-{4-[4-(2-Amino-4-methyl-pentanoyl)-piperazin-1-yl]-phenylamino}-pyrido[2,3-d]pyrimidin-7-yl)-3-cyclohexyl-urea; and 1-(2-{4-[4-(2-Amino-3-methyl-butanoyl)-piperazin-1-yl]-phenylamino}-pyrido[2,3-d]pyrimidin-7-yl)-3-cyclohexyl-urea.

8. A compound selected from:
1-tert-Butyl-3-[2-(pyridin-4-ylamino)-pyrido[2,3-d]pyrimidin-7-yl]-urea;

1-Cyclohexyl-3-[2-(pyridin-4-ylamino)-pyrido[2,3-d]pyrimidin-7-yl]-urea;

1-Ethyl-3-[2-(pyridin-4-ylamino)-pyrido[2,3-d]pyrimidin-7-yl]-urea;

1-(Hydroxy-ethyl)-3-[2-(pyridin-4-ylamino)-pyrido[2,3-d]pyrimidin-7-yl]-urea;

1-tert-Butyl-3-[6-fluoro-2-(pyridin-4-ylamino)-pyrido[2,3-d]pyrimidin-7-yl]-urea;

1-Cyclohexyl-3-[6-fluoro-2-(pyridin-4-ylamino)-pyrido[2,3-d]pyrimidin-7-yl]-urea;

1-Ethyl-3-[6-fluoro-2-(pyridin-4-ylamino)-pyrido[2,3-d]pyrimidin-7-yl]-urea;

1-[6-Fluoro-2-(pyridin-4-ylamino)-pyrido[2,3-d]pyrimidin-7-yl]-3-(2-hydroxy-ethyl)-urea;

1-tert-Butyl-3-[5-methyl-2-(pyridin-4-ylamino)-pyrido[2,3-d]pyrimidin-7-yl]-urea;

1-Cyclohexyl-3-[5-methyl-2-(pyridin-4-ylamino)-pyrido[2,3-d]pyrimidin-7-yl]-urea;

1-Ethyl-3-[5-methyl-2-(pyridin-4-ylamino)-pyrido[2,3-d]pyrimidin-7-yl]-urea; and 1-(2-Hydroxy-ethyl)-3-[5-methyl-2-(pyridin-4-ylamino)-pyrido[2,3-d]pyrimidin-7-yl]-urea.

9. A compound selected from:
4-{4-[7-(3-tert-Butyl-ureido)-pyrido[2,3-d]pyrimidin-2-ylamino]-phenyl}-piperazine-1-carboxylic acid tert-butyl ester;

4-{4-[7-(3-Cyclohexyl-ureido)-pyrido[2,3-d]pyrimidin-2-ylamino]-phenyl}-piperazine-1-carboxylic acid tert-butyl ester;

1-(3-Hydroxy-propyl)-3-[2-(4-piperazin-1-yl-phenylamino)-pyrido[2,3-d]pyrimidin-7-yl]-urea;

1-((S)-1-Hydroxymethyl-3-methyl-butyl)-3-[2-(4-piperazin-1-yl-phenylamino)-pyrido[2,3-d]pyrimidin-7-yl]-urea;

4-Methyl-piperazine-1-carboxylic acid [2-(4-piperazin-1-yl-phenylamino)-pyrido[2,3-d]pyrimidin-7-yl]-amide;
Piperazine-1-carboxylic acid [2-(4-piperazin-1-yl-phenylamino)-pyrido[2,3-d]pyrimidin-7-yl]-amide;
1-((R)-1-Hydroxymethyl-2-methyl-propyl)-3-[2-(4-piperazin-1-yl-phenylamino)-pyrido[2,3-d]pyrimidin-7-yl]-urea;
1-[6-Bromo-2-(4-piperazin-1-yl-phenylamino)-pyrido[2,3-d]pyrimidin-7-yl]-3-tert-butyl-urea;
1-{6-Bromo-2-[4-(cis-3,5-dimethyl-piperazin-1-yl)-phenylamino]-pyrido[2,3-d]pyrimidin-7-yl}-3-cyclohexyl-urea;
1-[2-(4-Fluoro-phenylamino)-pyrido[2,3-d]pyrimidin-7-yl]-3-(3-morpholin-4-yl-propyl)-urea;
1-[2-(4-Fluoro-phenylamino)-pyrido[2,3-d]pyrimidin-7-yl]-3-(2-hydroxy-ethyl)-urea;
1-(2-Amino-ethyl)-3-[2-(4-fluoro-phenylamino)-pyrido[2,3-d]pyrimidin-7-yl]-urea;
1-Cyclohexyl-3-{2-[4-(3,3-dimethyl-piperazin-1-yl)-phenylamino]-6-fluoro-pyrido[2,3-d]pyrimidin-7-yl}-urea;
1-tert-Butyl-3-{2-[4-(cis-3,5-dimethyl-piperazin-1-yl)-phenylamino]-6-fluoro-pyrido[2,3-d]pyrimidin-7-yl}-urea;
1-tert-Butyl-3-{6-chloro-2-[4-(cis-3,5-dimethyl-piperazin-1-yl)-phenylamino]-pyrido[2,3-d]pyrimidin-7-yl}-urea;
3-Cyclohexyl-1-{2-[4-(cis-3,5-dimethyl-piperazin-1-yl)-phenylamino]-pyrido[2,3-d]pyrimidin-7-yl}-1-methyl-urea;
3-Cyclohexyl-1-ethyl-1-[2-(4-piperazin-1-yl-phenylamino)-pyrido[2,3-d]pyrimidin-7-yl]-urea;
3-tert-Butyl-1-{2-[4-(cis-3,5-dimethyl-piperazin-1-yl)-phenylamino]-pyrido[2,3-d]pyrimidin-7-yl}-1-ethyl-urea;
7-(3-tert-Butyl-ureido)-2-(4-piperazin-1-yl-phenylamino)-pyrido[2,3-d]pyrimidine-6-carboxylic acid ethyl ester;
1-Cyclohexyl-3-{2-[4-(3,3-dimethyl-piperazin-1-yl)-phenylamino]-pyrido[2,3-d]pyrimidin-7-yl}-urea;
1-Cyclohexyl-3-{2-[4-(cis-3,5-dimethyl-piperazin-1-yl)-phenylamino]-6-methyl-pyrido[2,3-d]pyrimidin-7-yl}-urea;
1-tert-Butyl-3-{2-[4-(cis-3,5-dimethyl-piperazin-1-yl)-phenylamino]-6-methyl-pyrido[2,3-d]pyrimidin-7-yl}-urea;
1-tert-Butyl-3-[6-methyl-2-(4-piperazin-1-yl)-phenylamino)-pyrido[2,3-d]pyrimidin-7-yl]-urea;
1-{2-[4-(cis-3,5-Dimethyl-piperazin-1-yl)-phenylamino]-6-methyl-pyrido[2,3-d]pyrimidin-7-yl}-3-isopropyl-urea;
1-Cyclopropyl-3-{2-[4-(cis-3,5-dimethyl-piperazin-1-yl)-phenylamino]-6-methyl-pyrido[2,3-d]pyrimidin-7-yl}-urea; and
1-tert-Butyl-3-{2-[4-(cis-3,5-dimethyl-piperazin-1-yl)-phenylamino]-6-ethyl-pyrido[2,3-d]pyrimidin-7-yl}-urea.

10. A pharmaceutical composition comprising a compound selected from claim 1 admixed with a pharmaceutically acceptable carrier, diluent, or excipient.

11. A method of inhibiting a cdk enzyme comprising contacting the cdk enzyme with a compound selected from claim 1.

12. A method of claim 11 wherein said cdk is cdk1.

13. A method of claim 11 wherein said cdk is cdk2.

14. A method of claim 11 wherein said cdk is cdk4.

15. A method of inhibiting a growth factor-mediated tyrosine kinase comprising contacting said growth factor-mediated kinase with a compound selected from claim 1.

16. A method of claim 15 wherein said growth factor-mediated tyrosine kinase is platelet derived growth factor (PDGF).

17. A method of claim 15 wherein said growth factor-mediated tyrosine kinase is fibroblast growth factor (FGF).

18. A method of treating a subject suffering from diseases caused by vascular smooth muscle cell proliferation comprising administering to said subject a therapeutically effective amount of a compound selected from claim 1.

* * * * *